US008258145B2

(12) United States Patent
Cai et al.

(10) Patent No.: US 8,258,145 B2
(45) Date of Patent: Sep. 4, 2012

(54) METHOD OF TREATING BRAIN CANCER

(75) Inventors: Sui Xiong Cai, San Diego, CA (US);
Mark B. Anderson, Salt Lake City, UT (US); Adam Willardsen, Sandy, UT (US); Nilantha Sudath Sirisoma, San Diego, CA (US)

(73) Assignee: Myrexis, Inc., Salt Lake, City, UT (US)

( * ) Notice: Subject to any disclaimer, the term of this patent is extended or adjusted under 35 U.S.C. 154(b) by 1461 days.

(21) Appl. No.: 11/773,285

(22) Filed: Jul. 3, 2007

(65) Prior Publication Data

US 2008/0051398 A1 Feb. 28, 2008

Related U.S. Application Data

(63) Continuation of application No. PCT/US2006/000122, filed on Jan. 3, 2006.

(60) Provisional application No. 60/641,263, filed on Jan. 3, 2005.

(51) Int. Cl.
*A61K 31/517* (2006.01)
*A61K 31/535* (2006.01)
*A61K 31/47* (2006.01)

(52) U.S. Cl. ........... 514/266.21; 514/234.5; 514/266.24; 514/266.4; 514/313

(58) Field of Classification Search ............. 514/266.21, 514/234.5, 266.24, 266.4, 313
See application file for complete search history.

(56) References Cited

U.S. PATENT DOCUMENTS

| | | |
|---|---|---|
| 2,883,382 A | 4/1959 | Eisiager et al. |
| 3,031,450 A | 4/1962 | Fischer et al. |
| 3,213,090 A | 10/1965 | Roch et al. |
| 3,502,681 A | 3/1970 | Allais et al. |
| 3,632,761 A | 1/1972 | Graham et al. |
| 3,769,410 A | 10/1973 | Bertrand |
| 3,971,783 A | 7/1976 | Barnish et al. |
| 4,025,629 A | 5/1977 | Coverdale |
| 4,322,420 A | 3/1982 | Kobayashi et al. |
| 4,421,920 A | 12/1983 | Baudouin et al. |
| 4,435,003 A | 3/1984 | Fletcher |
| 4,464,375 A | 8/1984 | Kobayashi et al. |
| 4,478,833 A | 10/1984 | Roch et al. |
| 4,480,096 A | 10/1984 | Fletcher |
| 4,510,307 A | 4/1985 | Hidaka et al. |
| 4,675,047 A | 6/1987 | Serban et al. |
| 4,714,698 A | 12/1987 | Roch et al. |
| 5,064,833 A | 11/1991 | Ife et al. |
| 5,114,939 A | 5/1992 | Dreikorn et al. |
| 5,145,843 A | 9/1992 | Arnold et al. |
| 5,187,168 A | 2/1993 | Primeau et al. |
| 5,223,505 A | 6/1993 | Hargreaves et al. |
| 5,236,925 A | 8/1993 | Primeau et al. |
| 5,240,940 A | 8/1993 | Arnold et al. |
| 5,256,781 A | 10/1993 | Primeau et al. |
| 5,270,466 A | 12/1993 | Haley |
| 5,276,148 A | 1/1994 | Siegel et al. |
| 5,294,622 A | 3/1994 | Dreikorn et al. |
| 5,330,989 A | 7/1994 | Soll et al. |
| 5,373,011 A | 12/1994 | Haley |
| 5,409,930 A | 4/1995 | Spada et al. |
| 5,436,233 A | 7/1995 | Lee et al. |
| 5,464,781 A | 11/1995 | Armitage et al. |
| 5,478,845 A | 12/1995 | Hansen et al. |
| 5,480,883 A | 1/1996 | Spada et al. |
| 5,565,472 A | 10/1996 | Hamanaka |
| 5,604,251 A | 2/1997 | Heitsch et al. |
| 5,618,814 A | 4/1997 | Heckel et al. |
| 5,618,829 A | 4/1997 | Takayanagi et al. |
| 5,646,153 A | 7/1997 | Spada et al. |
| 5,654,298 A | 8/1997 | Mills et al. |
| 5,654,307 A | 8/1997 | Bridges et al. |
| 5,656,643 A | 8/1997 | Spada et al. |
| 5,707,989 A | 1/1998 | Himmelsbach et al. |
| 5,710,158 A | 1/1998 | Myers et al. |
| 5,714,493 A | 2/1998 | Myers et al. |
| 5,721,237 A | 2/1998 | Myers et al. |
| 5,739,127 A | 4/1998 | Schohe-Loop et al. |
| 5,747,486 A | 5/1998 | Sohda et al. |
| 5,747,498 A | 5/1998 | Schnur et al. |
| 5,760,230 A | 6/1998 | Schohe-Loop et al. |
| 5,795,889 A | 8/1998 | Spada et al. |
| 5,874,438 A | 2/1999 | Schohe-Loop et al. |

(Continued)

FOREIGN PATENT DOCUMENTS

AU  2004253967 B2  2/2010

(Continued)

OTHER PUBLICATIONS

Cecil Textbook of Medicine, 21st Edition (2000), Goldman & Bennett (Editors), W.B. Saunders Company (Publisher), Chapter 198, pp. 1060-1074. Dass et al., Journal of Scientific & Industrial Research, 1952, 11B:461-463.
Dorwarld, Side Reactions in Organic Synthesis, 2005, Wiley: VCH, Weinheim p. IX of Preface.
Internal Medicine, 4th Editor-in-Chief Jay Stein, Chapters 71-72, pp. 699-715.
Vippagunta et al., Advanced Drug Delivery Reviews, 2001, 48:3-26.
Curd, F. H. S., et al., "Synthetic Antimalarials. Part XIV. Some 2-Arylamino-4-aminoalkylaminoquinazolines", Journal of the Chemical Society, 1947, pp. 775-783.
Elslager, et al., "Synthesis and antimalarial effects of N2-aryl-N4-[(dialkylamino)alkyl]- and N4-aryl-N2-[(dialkylamino)alkyl]-2,4-quinazolinediamines", J. Med. Chem., 1981, 24 (2), Feb. 1981, pp. 127-140.
"Burger's Medicinal Chemistry and Drug Discovery,", 5th Edition, Part 1, 1995, pp. 975-977.
"Database Beilstein", XP002314667, Database accession No. 636504 (CNR), J.SCI.IND.RES., vol. 11B, 1952, 7 pages.
"Database Caplus Chemical Abstracts Service", XP002314666, Database accession No. 1960:131417 (AN) & Cancer Research, Columbus, Ohio, US, vol. 20, No. 7-2, 1960, pp. 471-684.

(Continued)

*Primary Examiner* — Blessing Fubara
(74) *Attorney, Agent, or Firm* — Kelly A. Echols; Herbert L. Ley, III; Myrexis, Inc. IP Group

(57) ABSTRACT

Disclosed are 4-arylamino-quinazolines and analogs thereof effective as activators of caspases and inducers of apoptosis. The compounds of this invention are useful in the treatment of a variety of clinical conditions in which uncontrolled growth and spread of abnormal cells occurs, and in particular to the use of these compounds in treating brain cancer.

41 Claims, No Drawings

U.S. PATENT DOCUMENTS

| | | | |
|---|---|---|---|
| RE36,256 E | 7/1999 | Spada et al. | |
| 5,948,819 A | 9/1999 | Ohtsuka et al. | |
| 5,952,346 A | 9/1999 | Heitsch et al. | |
| 5,965,740 A | 10/1999 | Kai et al. | |
| 6,002,008 A | 12/1999 | Wissner et al. | |
| 6,057,320 A | 5/2000 | Spada et al. | |
| 6,080,747 A | 6/2000 | Uckun et al. | |
| 6,080,748 A | 6/2000 | Uckun et al. | |
| 6,084,095 A | 7/2000 | Bridges et al. | |
| 6,124,330 A | 9/2000 | Venet et al. | |
| 6,127,374 A | 10/2000 | Bridges | |
| 6,136,837 A | 10/2000 | Kai et al. | |
| 6,177,433 B1 | 1/2001 | Uckun et al. | |
| 6,184,226 B1 | 2/2001 | Chakravarty et al. | |
| 6,204,267 B1 | 3/2001 | Tang et al. | |
| 6,232,312 B1 | 5/2001 | Pamukcu et al. | |
| 6,242,196 B1 | 6/2001 | Spiegelman et al. | |
| 6,251,912 B1 | 6/2001 | Wissner et al. | |
| 6,265,410 B1 | 7/2001 | Bridges et al. | |
| 6,265,425 B1 | 7/2001 | De Porre et al. | |
| 6,277,989 B1 | 8/2001 | Chakravarty et al. | |
| 6,284,764 B1 | 9/2001 | Kath et al. | |
| 6,297,258 B1 | 10/2001 | Wissner et al. | |
| 6,313,129 B1 | 11/2001 | Uckun et al. | |
| 6,313,130 B1 | 11/2001 | Uckun et al. | |
| 6,313,150 B1 | 11/2001 | Ohtsuka et al. | |
| 6,316,454 B1 | 11/2001 | Uckun et al. | |
| 6,326,373 B1 | 12/2001 | Uckun et al. | |
| 6,329,371 B1 | 12/2001 | Kai et al. | |
| 6,344,459 B1 | 2/2002 | Bridges et al. | |
| RE37,650 E | 4/2002 | Myers et al. | |
| 6,384,051 B1 | 5/2002 | Frost et al. | |
| 6,391,874 B1 | 5/2002 | Cockerill et al. | |
| 6,432,941 B1* | 8/2002 | Uckun et al. | 514/185 |
| 6,432,979 B1 | 8/2002 | Frost et al. | |
| 6,452,005 B1 | 9/2002 | Uckun et al. | |
| 6,455,534 B2 | 9/2002 | Bridges et al. | |
| 6,469,013 B2 | 10/2002 | Uckun et al. | |
| 6,476,031 B1 | 11/2002 | Chakravarty et al. | |
| 6,476,040 B1 | 11/2002 | Norris et al. | |
| 6,486,187 B1 | 11/2002 | Venet et al. | |
| 6,492,520 B1 | 12/2002 | Chen | |
| 6,495,556 B2 | 12/2002 | Uckun et al. | |
| 6,518,283 B1 | 2/2003 | Langham et al. | |
| 6,521,620 B1 | 2/2003 | Bridges et al. | |
| 6,541,481 B2 | 4/2003 | Kath et al. | |
| 6,552,027 B2 | 4/2003 | Uckun et al. | |
| 6,552,055 B1 | 4/2003 | Spiegelman et al. | |
| 6,562,319 B2 | 5/2003 | Mishani et al. | |
| 6,562,818 B1 | 5/2003 | Bridges | |
| 6,602,863 B1 | 8/2003 | Bridges et al. | |
| 6,617,329 B2 | 9/2003 | Himmelsbach et al. | |
| 6,627,634 B2 | 9/2003 | Himmelsbach et al. | |
| 6,635,651 B2 | 10/2003 | Uckun | |
| 6,635,655 B1 | 10/2003 | Jayyosi et al. | |
| 6,645,969 B1 | 11/2003 | Myers et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,664,247 B2 | 12/2003 | Bebbington et al. | |
| 6,713,484 B2 | 3/2004 | Bridges et al. | |
| 6,727,251 B2 | 4/2004 | Bebbington et al. | |
| 6,740,651 B2 | 5/2004 | Himmelsbach et al. | |
| 6,794,389 B2 | 9/2004 | Okana et al. | |
| 6,828,320 B2 | 12/2004 | Cockerill et al. | |
| 6,833,375 B2 | 12/2004 | Venet et al. | |
| 6,864,255 B2 | 3/2005 | Geuns-Meyer et al. | |
| 6,890,924 B2 | 5/2005 | Kath et al. | |
| 7,087,613 B2 | 8/2006 | Norris et al. | |
| 7,618,975 B2* | 11/2009 | Cai et al. | 514/262.1 |
| 7,989,462 B2 | 8/2011 | Cai et al. | |
| 2001/0014679 A1 | 8/2001 | Tang et al. | |
| 2002/0025968 A1 | 2/2002 | Pamukcu et al. | |
| 2002/0048271 A1 | 4/2002 | Rastinejad et al. | |
| 2002/0082270 A1 | 6/2002 | Himmelsbach et al. | |
| 2002/0147198 A1 | 10/2002 | Chen et al. | |
| 2002/0161010 A1 | 10/2002 | Chakravarty et al. | |
| 2002/0165243 A1 | 11/2002 | Uckun et al. | |
| 2002/0169180 A1 | 11/2002 | Himmelsbach et al. | |
| 2002/0177601 A1 | 11/2002 | Himmelsbach et al. | |
| 2003/0055068 A1 | 3/2003 | Bebbington et al. | |
| 2003/0069248 A1 | 4/2003 | Chakravarty et al. | |
| 2003/0087908 A1 | 5/2003 | Geuns-Meyer et al. | |
| 2003/0087931 A1 | 5/2003 | Mailliet et al. | |
| 2003/0105090 A1 | 6/2003 | Bebbington et al. | |
| 2003/0134836 A1 | 7/2003 | Elbaum et al. | |
| 2003/0144178 A1 | 7/2003 | Uckun | |
| 2003/0144330 A1 | 7/2003 | Spiegelman et al. | |
| 2003/0144506 A1 | 7/2003 | Brown | |
| 2003/0149045 A1 | 8/2003 | Fatih | |
| 2003/0149062 A1 | 8/2003 | Jung et al. | |
| 2003/0162799 A1 | 8/2003 | Langham et al. | |
| 2003/0165873 A1 | 9/2003 | Come et al. | |
| 2003/0186995 A1 | 10/2003 | Kath et al. | |
| 2003/0195230 A1 | 10/2003 | Chen et al. | |
| 2003/0203922 A1 | 10/2003 | Patel et al. | |
| 2003/0220336 A1 | 11/2003 | Jung | |
| 2003/0225089 A1 | 12/2003 | Jung et al. | |
| 2003/0229051 A1 | 12/2003 | Bridges et al. | |
| 2004/0014774 A1 | 1/2004 | Myers et al. | |
| 2004/0034044 A1 | 2/2004 | Okano et al. | |
| 2004/0034045 A1 | 2/2004 | Uckun | |
| 2004/0038856 A1 | 2/2004 | Chakravarty et al. | |
| 2004/0043388 A1 | 3/2004 | Come et al. | |
| 2005/0137213 A1* | 6/2005 | Cai et al. | 514/262.1 |
| 2005/0227992 A1 | 10/2005 | Hurley et al. | |
| 2007/0208044 A1 | 9/2007 | Cai et al. | |
| 2007/0244113 A1 | 10/2007 | Cai et al. | |
| 2007/0249601 A1 | 10/2007 | Cai et al. | |
| 2008/0004297 A1 | 1/2008 | Cai et al. | |
| 2008/0039479 A1 | 2/2008 | Cai et al. | |
| 2010/0069383 A1 | 3/2010 | Anderson et al. | |

FOREIGN PATENT DOCUMENTS

| | | | |
|---|---|---|---|
| DE | 1151806 B | | 7/1963 |
| DE | 4132763 A1 | | 4/1993 |
| DE | 19801438 A1 | | 7/1999 |
| DE | 10040527 A1 | | 2/2002 |
| DE | 20204129 U1 | | 7/2002 |
| EP | 0 404 322 A1 | | 12/1990 |
| FR | 1543405 A | | 10/1968 |
| FR | 1543448 A | | 10/1968 |
| FR | 1557928 A | | 2/1969 |
| FR | 2047882 A1 | | 3/1971 |
| FR | 2229413 A1 | | 12/1974 |
| GB | 807826 A | | 1/1959 |
| GB | 971166 A | | 9/1964 |
| GB | 1195491 A | | 6/1970 |
| GB | 2 033 894 A | * | 5/1980 |
| GB | 2033894 A | | 5/1980 |
| GB | 2052481 A | | 1/1981 |
| GB | 2230527 A | | 10/1990 |
| GB | 2295387 A | | 5/1996 |
| IN | 239781 | | 3/2010 |
| JP | 37-7238 A | | 7/1962 |
| JP | 56-20577 A | | 2/1981 |
| JP | 57-144266 A | | 9/1982 |
| JP | 02-502462 A | | 8/1990 |
| JP | 03-17068 A | | 1/1991 |
| JP | 3-505741 A | | 12/1991 |
| JP | 06-500117 A | | 1/1994 |
| JP | 08-003144 A | | 1/1996 |
| JP | 09-301933 A | | 11/1997 |
| JP | 11-507355 A | | 6/1999 |
| JP | 2003-012631 A | | 1/2003 |
| NZ | 544472 | | 8/2009 |
| WO | 89/05297 A1 | | 6/1989 |
| WO | WO 89/05297 | | 6/1989 |
| WO | WO 89/05297 | | 6/1989 |
| WO | 90/12790 A1 | | 11/1990 |
| WO | 92/05158 A1 | | 4/1992 |
| WO | 92/14714 A1 | | 9/1992 |
| WO | 92/14716 A1 | | 9/1992 |
| WO | 92/20642 A1 | | 11/1992 |
| WO | 93/04048 A1 | | 3/1993 |
| WO | 93/08170 A1 | | 4/1993 |
| WO | 93/13097 A1 | | 7/1993 |

| | | |
|---|---|---|
| WO | 93/13776 A1 | 7/1993 |
| WO | 93/15058 A1 | 8/1993 |
| WO | 93/17682 A1 | 9/1993 |
| WO | 94/08975 A1 | 4/1994 |
| WO | 94/14763 A1 | 7/1994 |
| WO | 94/27994 A1 | 12/1994 |
| WO | 95/15758 A1 | 6/1995 |
| WO | WO 95/15758 * | 6/1995 |
| WO | 95/19774 A1 | 7/1995 |
| WO | 95/27693 A1 | 10/1995 |
| WO | 96/07657 A1 | 3/1996 |
| WO | 96/09294 A1 | 3/1996 |
| WO | 96/14319 A1 | 5/1996 |
| WO | 96/30347 A1 | 10/1996 |
| WO | 96/39145 A1 | 12/1996 |
| WO | 97/20820 A1 | 6/1997 |
| WO | 97/20821 A1 | 6/1997 |
| WO | 97/20822 A1 | 6/1997 |
| WO | 97/20823 A2 | 6/1997 |
| WO | 97/24328 A1 | 7/1997 |
| WO | 97/28133 A1 | 8/1997 |
| WO | 97/12863 A1 | 10/1997 |
| WO | 97/38983 A1 | 10/1997 |
| WO | 97/49704 A1 | 12/1997 |
| WO | 98/02434 A1 | 1/1998 |
| WO | 98/05661 A1 | 2/1998 |
| WO | WO 98/10767 | 3/1998 |
| WO | 98/25598 A2 | 6/1998 |
| WO | 98/43960 A1 | 10/1998 |
| WO | 98/50370 A1 | 11/1998 |
| WO | 99/06378 A1 | 2/1999 |
| WO | 99/09016 A1 | 2/1999 |
| WO | 99/09986 A1 | 3/1999 |
| WO | 99/32098 A2 | 7/1999 |
| WO | 99/61428 A1 | 12/1999 |
| WO | 00/10981 A1 | 3/2000 |
| WO | 00/12497 A2 | 3/2000 |
| WO | 00/18740 A1 | 4/2000 |
| WO | 00/27819 A2 | 5/2000 |
| WO | 00/00202 A1 | 6/2000 |
| WO | 00/32175 A2 | 6/2000 |
| WO | 00/44728 A1 | 8/2000 |
| WO | 00/51587 A2 | 9/2000 |
| WO | 00/51991 A1 | 9/2000 |
| WO | 00/55141 A1 | 9/2000 |
| WO | 00/64888 A1 | 11/2000 |
| WO | 00/73260 A1 | 12/2000 |
| WO | 00/78735 A1 | 12/2000 |
| WO | 01/12227 A1 | 2/2001 |
| WO | 01/21594 A1 | 3/2001 |
| WO | 01/21595 A1 | 3/2001 |
| WO | 01/21596 A1 | 3/2001 |
| WO | 01/25218 A1 | 4/2001 |
| WO | 01/72710 A1 | 4/2001 |
| WO | 01/45641 A2 | 6/2001 |
| WO | 01/68186 A2 | 9/2001 |
| WO | 01/77104 A1 | 10/2001 |
| WO | 01/94341 A1 | 12/2001 |
| WO | 01/98277 A2 | 12/2001 |
| WO | 02/18370 A1 | 3/2002 |
| WO | 02/18372 A1 | 3/2002 |
| WO | 02/18376 A1 | 3/2002 |
| WO | 02/24666 A2 | 3/2002 |
| WO | 02/24667 A1 | 3/2002 |
| WO | 02/30927 A1 | 4/2002 |
| WO | 02/32872 A1 | 4/2002 |
| WO | 02/36577 A1 | 5/2002 |
| WO | 02/43735 A1 | 6/2002 |
| WO | 02/47690 A1 | 6/2002 |
| WO | 02/055501 A2 | 7/2002 |
| WO | 02/059112 A2 | 8/2002 |
| WO | 02/066461 A1 | 8/2002 |
| WO | 02/068406 A2 | 9/2002 |
| WO | 02/068415 A1 | 9/2002 |
| WO | 02/073235 A2 | 9/2002 |
| WO | 02/074341 A1 | 9/2002 |
| WO | 02/076975 A1 | 10/2002 |
| WO | 02/083654 A1 | 10/2002 |
| WO | 03/005026 A2 | 1/2003 |
| WO | 03/028641 A2 | 4/2003 |
| WO | 03/040108 A1 | 5/2003 |
| WO | 03/040109 A2 | 5/2003 |
| WO | 03/045395 A1 | 6/2003 |
| WO | 03/045939 A1 | 6/2003 |
| WO | 03/062209 A2 | 7/2003 |
| WO | 03/066060 A2 | 8/2003 |
| WO | 03/066602 A1 | 8/2003 |
| WO | 03/082290 A1 | 10/2003 |
| WO | 03/084503 A2 | 10/2003 |
| WO | 03/084539 A2 | 10/2003 |
| WO | 03/089439 A1 | 10/2003 |
| WO | 03/091224 A1 | 11/2003 |
| WO | 03/097615 A1 | 11/2003 |
| WO | 2004/007457 A2 | 1/2004 |
| WO | 2004/007481 A1 | 1/2004 |
| WO | 2004/035543 A1 | 4/2004 |
| WO | 2004/078114 A2 | 9/2004 |
| WO | 2005/003100 A2 | 1/2005 |
| WO | 2006/014420 A1 | 2/2006 |
| WO | 2006/074147 A2 | 7/2006 |

OTHER PUBLICATIONS

Ife et al.. "Reversible Inhibitors of the Gastric (H+/K+)-ATPase. 5. Substituted 2,4-Diaminoquinazolines and Thienopyrimidines."Journal of Medical Chemistry, vol. 38, 1995, pp. 2763-2773.
Final Office Action received for U.S. Appl. No. 11/680,843, mailed on Apr. 30, 2009, 11 pages.
Examiner Interview Summary received for U.S. Appl. No. 11/680,843, mailed on Jan. 29, 2009, 4 pages.
Non-Final Office Action received for U.S. Appl. No. 11/680,843, mailed on Oct. 16, 2008, 9 pages.
Non-Final Office Action received for U.S. Appl. No. 11/680,843, mailed on Apr. 9, 2008, 17 pages.
Abramovitch, et al., "Direct acylamination of quinoline, isoquinoline, benzimidazole, pyridazine, and pyrimidine 1-oxides. Novel 1, 5-sigmatropic shift", Journal of Organic Chemistry, vol. 40, No. 1, 1975, pp. 41-50.
Allais, et al., "Analgesic compounds with no narcotic activity. Study of new 4- (2'-alkoxycarbonyl phenylamino) quinolines and related molecules", Chimica Therapeutica, vol. 8, No. 2, 1973, pp. 154-168.
Almog, et al., "Mesomerism in N, N-dialkyl-N-(heteroaryl) amines", Tetrahedron, vol. 30, No. 4, 1974, pp. 549-552.
Anwar, et al., "Some reactions of 4-cholorquinazoline, 6-nitro- and 6-amino-4 (3H)—quinazolones", Revue Roumaine de Chimie, vol. 26, No. 11-12, 1981, pp. 1469-1478.
Apelt, et al., "Development of a New Class of Nonimidazole Histmine H3 Receptor Ligands with Combined Inhibitory Histamine N-Methyltransferase Activity", Journal of Medicinal Chemistry, vol. 45, No. 05, 2002, pp. 1128-1141.
Assefa, et al., "3D-QSAR and docking studies on 4-anilinoquinazoline and 4-anilinoquinoline epidermal growth factor receptor (EGFR) tyrosine kinase inhibitors", Journal of Computer-Aided Molecular Design, vol. 17, No. 8, 2003, pp. 475-493.
Bala, et al., "Studies on the structure of 2-phenylquinoline-3-carboxylic acid derivatives", Zeszyty Naukowe Uniwersytetu Jagiellonskiego, Prace Chemiczne, vol. 21, 1976, pp. 179-189.
Banker, et al., "Modern Pharmaceuticals", Third Edition, Revised and Expanded, India's Leading Pharmaceutical Magazine, Ringer, 1996, 596 pages.
Barluenga, J., et al., "Reaction of 3-Amino-2-alkenimines with Alkali Metals: Unexpected Synthesis of Substituted 4-(Arylamino) quinolines", Journal of Organic Chemistry, vol. 54, No. 11, XP002314665, 1989, pp. 2596-2598.
Berlot, et al., "Aminoquinolines. XI. Decomposition of tertiary 4-aminoquinolines and of related amities by hydrobromic acid in aqueous solution. Influence of the nature of the ring and of the hydrocarbon chain", Bulletin de la Societe Chimique de France, vol. 11, No. 2, 1973, pp. 3175-3178.
Bethegnies, et al., "7-Chloro (phenylthio)-4-phenylaminoquinolines. Study on the anti-inflammatory and analgesic activities", Farmaco, Edizione Scientifica, vol. 41, No. 6, 1986, pp. 471-477.
Borisy, et al., "Systematic discovery of multicomponent therapeutics", PNAS—Proceedings of the National Academy of Sciences of the United States of America, vol. 100, No. 13, Jun. 24, 2003, pp. 7977-7982.

Boschelli, et al., "Synthesis and Src kinase inhibitory activity of a series of 4-phenylamino-3-quinolinecarbonitriles", Journal of Medicinal Chemistry, vol. 44, No. 5, 2001, pp. 822-833.

Bouey-Bencteux, et al., "Synthesis and antiproliferative properties of 4-aminoquinazoline derivatives as inhibitors of EGF receptor-associated tyrosine kinase activity", Anti-Cancer Drug Design, vol. 13, No. 08, 1998, pp. 893-922.

Bridges, et al., "Tyrosine kinase inhibitors: unusually steep structure-activity relationship for analogs of 4-(3-bromoanilino)-6, 7-dimethoxyquinazoline (PD 153035), a potent inhibitor of the epidermal growth factor receptor", Journal of Medicinal Chemistry, vol. 39, No. 01, 1996, pp. 267-276.

Denny, et al., "The 4-anilinoquinazoline class of inhibitors of the erbB family of receptor tyrosine kinases", Farmaco, vol. 56, No. 1-2, 2001, pp. 51-56.

Desai, et al., "Quinoline derivatives as antitubercular/antibacterial agents", Indian Journal of Chemistry, Section B: Organic Chemistry Including Medicinal Chemistry, vol. 35B, No. 08, 1996, pp. 871-873.

Doleschall, et al., "4H-3, 1-Benzoxazin-4-ones. VII. Water elimination reactions of N-(2-ureidobenzoyl) anthranilic acids", Tetrahedron, vol. 24, No. 16, 1968, pp. 5529-5545.

Dymek, et al., "Additional syntheses and transformations of compounds of the 2, 4-diarylaminoquinazoline type. III", Ann. Univ. Mariae Curie-Sklodowska, Lublin-Polonia Sect. AA, vol. 9, 1954, pp. 45-52.

Dymek, et al., "Reactions of acetamide with aniline and phenyl isothiocyanate", Ann. Univ. Mariae Curie-Sklodowska, Lublin-Poloina Sect. AA, vol. 9, 1954, pp. 35-43.

Elslager, et al., "Amodiaquine N-oxides and other 7-chloro-4-aminoquinoline N-oxides", Journal of Heterocyclic Chemistry, vol. 1, No. 1, 1964, pp. 6-12.

Elslager, et al., "Antifilarial agents. I. Effects of 4-[(7-chloro-4-quinolyl)amino)-a-(mono-and dialkylamino)-o-cresols and related compounds against *Litomosoides carnii* in gerbils", Journal of Medicinal Chemistry, vol. 12, No. 5, 1969, pp. 965-969.

Fischer, et al., "Zur Kenntnis substituierter γ-Aminochinoline", Journal fuer Praktische Chemie (Leipzig), 1925, pp. 59-68.

Fusco, et al., "Reactions of a-arylazo-a-cholroacetic acid esters with cyclic tertiary bases", Gazzetta Chimica Italiana, vol. 98, No. 5, 1968, pp. 511-534.

Galanakis, et al., "Synthesis and Quantitative Structure-Activity Relationship of Dequalinim Analogs as K+ Channel Blockers: Investigations on the Role of the Substituent at Position 4 of the Quinoline Ring", Journal of Medicinal Chemistry, vol. 38, No. 18, 1995, pp. 3536-3546.

Gee-Chen, Chang et al., "Molecular mechanisms of ZD1839-induced GI-cell cycle arrest and apoptosis in human lung adenocarcinoma A549 cells", Biochemical Pharmacology vol. 68, 2004, 1453-1464.

Gershuns, et al., "Interaction of 2-(2'-benzimidazolyl) quinoline derivatives with Cu+ ions", Ukrainskii Khimicheskii Zhurnal (Russian Edition), vol. 37, No. 3, 1971, pp. 263-265.

Gfesser, et al., "Synthesis and structure-activity relationships of 5-heteroatom-substituted pyridopyrimidines as adenosine kinase inhibitors", European Journal of Medicinal Chemistry, vol. 38, No. 3, 2003, pp. 245-252.

Gineinah, et al., "Study on the synthesis of some new 1, 4-dihydro-4-oxoquinazoline derivatives", Zhonghua Yaoxue Zazhi, vol. 45, No. 1, 1993, pp. 7-14.

Girgis, et al., "Phosphorus pentoxide in organic synthesis 25. New one-step synthesis of 4-aminoquinazolines. Comparison between mass spectra of 4-aminoquinazolines and 6-aminopurines", Chemica Scripta, vol. 26, No. 04, 1986, pp. 617-621.

Goossens, et al., "DNA Interaction of the Tyrosine Protein Kinase Inhibitor PD153035 and Its N-Methyl Analogue", Biochemistry, vol. 40, No. 15, 2001, pp. 4663-4671.

Hamana, et al., "Preparation of 2- and 4-substituted quinolines from 1-(2-quinolyl)—and 1-(4-quinolyl) pyridinium salts", Yakugaku Zasshi, vol. 84, 1964, pp. 42-47.

Hassan, et al., "Determination of glafenine in dosage forms and serum by thin-layer densitometry and high performance liquid chromatography", Journal of Pharmaceutical and Biomedical Analysis, vol. 16, No. 02, 1997, pp. 215-221.

Hidaka, et al., "Selective inhibitors of three forms of cyclic nucleotide phosphodiesterase—basic and potential clinical applications", Advances in Cyclic Nucleotide and Protein Phosphorylation Research, vol. 16, 1984, pp. 245-259.

Himbert, et al., "Aminoethynyl metalation. Part 3. 3-aminopropiolimidic acid derivatives -(aminoethynyl) stannylation of isocyanates, isothiocyanates, and carbodiimides", Tetrahedron Letters, No. 22, 1978, pp. 1951-1954.

Himbert, et al., "Aminoethynyl metalations. 11. Reaction of silylated and stannylated ynamines with carbodiimides", Liebigs Annalen der Chemie, No. 7, 1983, pp. 1185-1193.

Himbert, et al., "Aminoethynyl metalations. 13. Synthesis and reactions of 3-aminopropiolamidines", Liebigs Annalen der Chemie, No. 01, 1984, pp. 85-97.

Hutchings, et al., "Unusually high probability of second harmonic generation by some crystalline organic aldehydes", MCLC Section B: Nonlinear Optics, vol. 7, No. 1-2, 1994, pp. 157-166.

Ife, et al., "Reversible Inhibitors of the Gastric (H+/K+)-ATPase. 5. Substituted 2, 4-Diaminoquinazolines and Thienopyrimidines", Journal of Medicinal Chemistry, vol. 38, No. 14, 1995, pp. 2763-2773.

Iida, et al., "Fluorescence of 2, 4, 6, 8-substituted pyrimido [5, 4d] pyrimidines", Kogyo Kagaku Zasshi, vol. 70, No. 12, 1967, pp. 2308-2312.

Johannsen, et al., "Reaction of 4-quinazolinamines with organolithium reagents", Chemica Scripta, vol. 27, No. 2, 1987, pp. 277-281.

Kappe, et al., "Rearrangements of heterocycles. VIII. Mesoionic six-membered-ring heterocycles. XII. Ketenoid rearrangements of mesoionic pyrimidines", Chemische Berichte, vol. 112, No. 10, 1979, pp. 3424-3431.

Kasibhatla, et al., "MPC-6827: A Small-Molecule Inhibitor of Microtubule Formation That Is Not a Substrate for Multidrug Resistance Pumps", Research Article, Cancer Research, vol. 67, No. 12, Jun. 15, 2007, pp. 5865-5871.

Lee, et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities", Journal of Medicinal Chemistry, vol. 38, No. 18, 1995, pp. 3547-3557.

Leiter, "Cancer chemotherapy screening data. VII", Cancer Research, vol. 20, No. 7, Pt. 2, 1960, pp. 471-684.

Lin, et al., "Some physicochemical parameters of 11H-indolo [3,2-c] quinoline", Heterocycles, vol. 29, No. 12, 1989, pp. 2353-2359.

McDonald, et al., "Conversion of (2-chlorallyl) amines into heterocyclic compounds. I. 2-Methylindoles, 1,5,6,7-tetrahydro-3-methylindol-4-ones, and related heterocycles", Journal of the Chemical Society, Perkin Transactions, 1: Organic and Bio-Organic Chemistry (1972-1999), No. 15, 1975, pp. 1446-1450.

Moreau, et al., "Autocorrelation of molecular structures. Application to SAR studies", Nouveau Journal de Chimie, vol. 4, No. 12, 1980, pp. 757-764.

Myers, et al., "The preparation and SAR of 4-(anilino), 4-(phenoxy), and 4-(thiophenoxy)-quinazolines: inhibitors of p56Ick and EGF-R tyrosine kinase activity", Bioorganic Medicinal Chemistry Letters, vol. 7, No. 4, 1997, pp. 417-420.

Myers, et al., "The synthesis and SAR of new 4-(N-alkyl-N-phenyl) amino-6, 7-dimethoxyquinazolines and 4-(N-alkyl-N-phenyl) aminopyrazolo [3,4,d] pyrimdnes, inhibitors of CSF-1R tyrosine kinase activity", Bioorganic Medicinal Chemistry Letters, vol. 7, No. 4, 1997, pp. 421-424.

International Search Report received for International Patent Application No. PCT/US2004/021631, Mailed on Jul. 6, 2004, 7 pages.

Rewcastle, et al., "Tyrosine kinase inhibitors", Chapter 5, Synthesis and structure-activity relationships for 4-[(phenylmethyl)amino]— and 4-(phenylamino)quinazolines as potent adenosine 5'—triphosphate binding site inhibitors of the tyrosine kinase domain of the epidermal growth factor receptor, Journal of Med., Chem., vol. 38, 1995, pp. 3482-3487.

Rigby, J. H., et al., "Organic Letters", vol. 5, No. 7, XP002314664, 2003, pp. 1151-1153.

Roy, Dolly, et al., "Synthesis of 2-Amino-4-(Chloroanilino)-Pteridines and the Mode of Their Inhibitory Action on the Growth of Micro-Organisms", Journal of the Indian Chemical Society, vol. 36, No. 09, 1959, pp. 651-658.

Schaumann, et al., "New synthesis and reaction behavior of aminoethynyl sulfides", Chemische Berichte, vol. 116, No. 2, 1983, pp. 509-513.

Stein, Jay, "Internal Medicine", Editor-in-Chief, 4th Edition, Chapters 71-72, 1998, pp. 699-715.

Tronchet, et al., "C-Glycosyl derivatives. XLII. Synthesis of novel types of C-glycosyl derivatives from acetylenic sugars or their partial synthetic equivalents. Preliminary Communication", Helvetica Chimica Acta, vol. 64, No. 7, 1981, pp. 2322-2327.

Warhurst, et al., "The chemotherapy of rodent malaria. XXXIII. The activity of chloroquine and related blood schizonticides and of some analogs in drug-induced pigment clumping", Annals of Tropical Medicine Parasitology, vol. 76, No. 3, 1982, pp. 257-264.

Wright, et al., "Anilinoquinazoline Inhibitors of Fructose 1, 6-Bisphosphatase Bind at a Novel Allbsteric Site: Synthesis, In Vitro Characterization, and X-ray Crystallography", Journal of Medicinal Chemistry, vol. 45, No. 18, 2002, pp. 3865-3877.

Yum, et al., "Synthesis and pharmacological profile of 1-aryl-3-substituted pyrrolo [3,2-c] quinolines", Bioorganic Medicinal Chemistry Letters, vol. 9, No. 19, 1999, pp. 2819-2822.

Zakaria, Rachid, et al., The 1-45 Combi-Targeting Concept: Chemical Dissection of the Dual Targeting Properties of a Series of "Combi-Triazenes", Journal of Medicinal Chemistry, Coden: JMCMAR, ISSN: 0022-2623, XP002613544, compound 8, vol. 46, No. 20, 2003, pp. 4313-4321.

Zankowska-Jasinska, et al., "2-Benzhydrylmethyl-4-phenylaminoquinoline salts with dicarboxylic acids", Zeszyty Naukowe Uniwersytetu Jagiellonskiego, Prace Chemiczne, vol. 21, 1976, pp. 127-132.

Zieba, et al., "Azinyl sufides, part LXIII. 1-Alkyl-4-(arylamino) quinolinium-3-thiolates and 7-alkyl-12H-quino [3,4-b]-1,4-benzothiazinium salts", European Journal of Organic Chemistry, vol. 16, 2000, pp. 2947-2953.

"Database Beilstein", XP002314668, Database accession No. 329732, Jun. 27, 1988, 2 pages.

* cited by examiner

METHOD OF TREATING BRAIN CANCER

CROSS REFERENCE TO RELATED U.S. APPLICATION

This application is a continuation of international patent application no. PCT/US06/000122, filed Jan. 3, 2006, which claims the benefit of U.S. Provisional Application Ser. No. 60/641,263, filed on Jan. 3, 2005, each of which are incorporated herein by reference in their entirety.

FIELD OF THE INVENTION

This invention is in the field of medicinal chemistry. In particular, the invention relates to compounds that are activators of caspases and inducers of apoptosis. The invention also relates to the use of these compounds as therapeutically effective anti-cancer agents, and in particular to the use of these compounds in treating cancer of the brain and central nervous system (CNS).

BACKGROUND OF THE INVENTION

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al, *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. M phase specific antineoplastic drugs, such as vinblastine and paclitaxel, are known to affect tubulin polymerization. The ability of cells to appropriately polymerize and depolymerize tubulin is thought to be an important activity for M phase cell division.

Many slow growing tumors, e.g. colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

However, current use of apoptosis inducers and other antineoplastic drugs as chemotherapy for brain tumors has been limited. Surgical removal is the primary therapy for most patients with brain tumors rather than chemotherapy (see Karim et al., *Int. J. Radiat. Oncol. Biol. Phys.* 52:316-324 (2002); Patchell R A, *Cancer Treat Rev* 29:533-540 (2003)). Radiation therapy is also a part of treatment for many brain tumors as it has been shown to lengthen disease-free survival in patients with low grade glioma (Karim et al., Int. J. Radiat. Oncol. Biol. Phys. 52:316-324 (2002)). One limitation in the use of chemotherapy for brain tumors is due to the difficulty in achieving adequate exposure of the drug to the tumor. Carmustine has been incorporated into biodegradable polymers to achieve prolonged exposure of an antineoplastic agent to the tumor (Brem et al., *Lancet* 345:1008-1012

(1995). However, administration of the drug-impregnated biodegradable polymers is administered by implantation at the tumor site during surgery. Administering chemotherapy during surgery or by direct infusion of an agent to the site of the brain tumors is difficult and uncomfortable for the patient. Thus, a need exists for chemotherapeutic agents able to achieve adequate exposure to tumors of the brain and CNS without the need for direct infusion at the tumor site.

SUMMARY OF THE INVENTION 4-arylamino-quinazoline compounds and analogs, as represented in Formulae I-III below, are potent tubulin inhibitors. They are activators of the caspase cascade leading to the activation of caspase-3 and inducers or promoters of apoptosis. Thus, they are useful in treating or delaying the onset of diseases and disorders that are responsive to the inhibition of tubulin or to the induction of apoptosis.

It has now been surprisingly discovered that compounds having Formulae I-III are able to achieve adequate concentration in the brain and CNS to be effective as treatment and/or prophylaxis for diseases and disorders of the brain and CNS, such as brain and spinal cord tumors.

Accordingly, one aspect of the present invention is directed to the use of compounds of the present invention in inhibiting tubulin, in inducing caspase activities, particularly caspase-3 activities, and inducing or promoting apoptosis, by administering the compounds to cells in vitro or in vivo in warm-blood animals, particularly mammals.

Another aspect of the present invention is directed to the use of compounds of the present invention as therapy or prophylaxis for diseases and disorders of the brain and CNS. In particular, the invention provides a method for treating cancers of the brain and CNS. The invention also provides a method for reducing the size or slowing the growth of brain neoplasms, or improving the survival of patients with tumors of the brain or CNS. The methods comprise administering to a subject mammal in need of the treatment a therapeutically effective amount of a compound of the present invention.

Yet, another aspect of the present invention is to provide a method for treating or delaying the onset of diseases and disorders that are responsive to inhibition of tubulin, including but not limited to neoplastic diseases (such as cancer), psoriasis, autoimmune diseases, and fungi infection. The method comprises administering to a subject mammal in need of the treatment a therapeutically effective amount of a compound of the present invention.

Yet another aspect of the present invention is to provide a pharmaceutical composition useful for treating disorders responsive to the inhibition of tubulin and the induction of apoptosis, containing an effective amount of a compound of the present invention, preferably in admixture with one or more pharmaceutically acceptable carriers or diluents.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

Compounds of the present invention are potent inhibitors of tubulin and can also inhibit topoisomerase activities, such as topoisomerase II-dependent conversion of supercoiled DNA to topoisomers. The compounds are potent and highly efficacious activators of the caspase cascade particularly caspase-3, and inducers of apoptosis. Therefore, the compounds are useful for treating diseases and disorders responsive to induction of apoptosis, inhibition of tubulin and/or inhibition of topoisomerase II.

It has now been surprisingly discovered that compounds having Formulae I-III are able to achieve adequate concentration in the brain and CNS to be effective as treatment and/or prophylaxis for diseases and disorders of the brain and CNS. In particular, compounds having Formulae I-III are able to treat diseases of the brain and CNS that are responsive to therapy by inducing apoptosis, activating caspases, inhibiting tubulin and/or topoisomerase in the brain. Such diseases include, for example, brain and spinal cord tumors.

Thus, the present invention provides a method of inhibiting tubulin in cells in vitro or in warm-blood animals, particularly mammals, more particularly humans. As used herein, the term "inhibiting tubulin" means inhibiting the polymerization (or assembly) of tubulin monomers or promoting depolymerization of microtubles (i.e., tubulin disassembly). Inhibition of tubulin can be assayed by methods known in the art.

The present invention also provides a method for inhibiting topoisomerase II in cells in vitro or in warm-blood animals, particularly mammals, more particularly humans. As used herein, the term "inhibiting topoisomerase II" means inhibiting the activities of the enzyme topoisomerase II in topoisomerase II-dependent conversion of supercoiled DNA to topoisomers. Inhibition of topoisomerase II activities can be assayed by methods known in the art.

In addition, the present invention also provides a method of activating caspase, particularly caspase-3 and inducing apoptosis in cells in vitro or in warm-blood animals, particularly mammals, more particularly humans. The term "activating caspase" as used herein means activating or enhancing the enzymatic (protease) activity of a caspase (e.g., caspase-3), which, if occurring inside cells, results in promoted apoptosis or cell death. The ability of a compound in activating caspase, particularly caspase-3, can be assayed in a method as provided in Example 61 below. The term "inducing apoptosis" as used herein means inducing apoptosis in cells so as to cause cell death. The ability of a compound to induce apoptosis can be tested by methods known in the art. Also provided are methods for treating or delaying the onset of diseases and disorders responsive to inhibiting tubulin, inhibiting topoisomerase II, activating caspase-3, or inducing apoptosis. Specific examples of such diseases and disorders are provided in details below.

The above various methods of the present invention can be practiced by or comprise treating cells in vitro or a warm-blood animal, particularly mammal, more particularly a human with an effective amount of a compound according to the present invention. As used herein, the phrase "treating . . . with . . . a compound" means either administering the compound to cells or an animal, or administering to cells or an animal the compound or another agent to cause the presence or formation of the compound inside the cells or the animal. Preferably, the methods of the present invention comprise administering to cells in vitro or to a warm-blood animal, particularly mammal, more particularly a human, a pharmaceutical composition comprising an effective amount of a compound according to the present invention.

Specifically, the methods of the present invention comprise treating cells in vitro or a warm-blood animal, particularly mammal, more particularly a human with an effective amount of a compound according to Formula I:

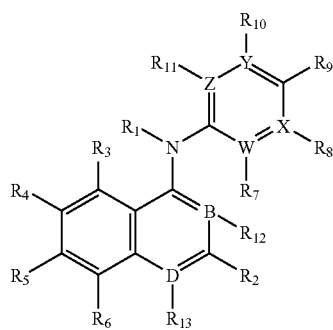

or pharmaceutically acceptable salts or solvates thereof, wherein:

$R_1$ is $C_{1-3}$ alkyl;

$R_2$ is halo, $R_{14}$, $OR_{14}$, $SR_{14}$, $NR_{15}R_{14}$, or $NR_{14}(C=O)C_{1-6}$ alkyl wherein $R_{15}$ is $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl and $R_{14}$ is H, $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl;

$R_3$, $R_4$, $R_6$-$R_8$, $R_{10}$-$R_{13}$ are independently halo, $R_{16}$, $NR_{16}R_{17}$, $OR_{16}$, or $SR_{16}$ wherein $R_{16}$ and $R_{17}$ are independently H, $C_{1-6}$ alkyl, $C_{2-6}$ alkenyl, $C_{2-6}$ alkynyl, or $C_{1-6}$ haloalkyl provided that $R_{16}$ and $R_{17}$ are not both H;

$R_5$ is H or $C_{1-3}$ alkyl;

$R_9$ is H, halo, $R_{18}$, $OR_{18}$, $SR_{18}$, $NR_{18}R_{19}$, or optionally $R_9$ and one of $R_8$ and $R_{10}$ together form a heterocycle, wherein $R_{18}$ and $R_{19}$ are independently H, $C_{1-6}$ alkyl, $C_{2-6}$ alkenyl, $C_{2-6}$ alkynyl, or $C_{1-6}$ haloalkyl provided that $R_{18}$ and $R_{19}$ are not both H; and B, D, W, X, Y and Z are independently C or N, provided that at least one of B and D is N, no more than one of W, X, Y and Z are N, and when B, D, W, X, Y or Z is N then there is no substituent at the N.

In specific embodiments of the compounds of Formula I, B is C and D is N. In specific embodiments of the compounds of Formula I, B is N and D is C. In specific embodiments of the compounds of Formula I, X or Y is N. In specific embodiments of the compounds of Formula I, W or Z is N.

In specific embodiments of the compounds of Formula I, $R_2$ is $C_{1-3}$ alkyl, halo, $C_{1-3}$ haloalkyl, $-OC_{1-3}$ alkyl, $-SC_{1-3}$ alkyl, $C_{3-8}$ heterocycle (preferably morpholino), $NR_{2a}C_{1-3}$ alkyl, $NR_{2a}(C=O)C_{1-3}$ alkyl, or $NR_{2a}$(arylalkyl) wherein $R_{2a}$ is H or $C_{1-3}$ alkyl.

In additional specific embodiments of the compounds of Formula I, $R_1$ is $CH_3$. In specific embodiments of the compounds of Formula I, $R_5$ is H. In specific embodiments of the compounds of Formula I, $R_3$, $R_4$, $R_6$-$R_8$, $R_{10}$-$R_{13}$ are independently H, $C_{1-3}$ alkyl, halo, $NH(C_{1-3}$ alkyl), $N(C_{1-3}$ alkyl$)_2$, or $-OC_{1-3}$ alkyl.

In additional specific embodiments of the compounds of Formula I, $R_9$ is H, OH, $C_{1-3}$ alkyl, halo, $C_{1-3}$ haloalkyl, $-OC_{1-3}$ alkyl, $-SC_{1-3}$ alkyl, $-OC_{1-3}$ haloalkyl, $NR_{9a}R_{9b}$ wherein $R_{9a}$ and $R_{9b}$ are independently H or $C_{1-3}$ alkyl provided that $R_{9a}$ and $R_{9b}$ are not both H, or optionally $R_9$ and one of $R_8$ and $R_{10}$ together form a $C_{3-8}$ heterocycle (preferably 1,3-dioxolane).

In a specific embodiment of the compounds of Formula I, $R_1$ is $CH_2CH_3$, or $CH_3$, preferably $CH_3$;

$R_2$ is $CH_2CH_3$, $CH_3$, Cl, $CH_2F$, $OCH_3$, $SCH_3$, morpholino, $NHCH_3$, $NCH_3(C=O)CH_3$, or $NHCH_2C_6H_5$;

$R_3$, $R_4$, $R_6$, $R_{12}$, and $R_{13}$ are independently H, $CH_3$, Cl, $NHCH_3$, $N(CH_3)_2$, or $OCH_3$;

$R_5$ is H;

$R_7$, $R_8$, $R_{10}$ and $R_{11}$ are independently H, F, or $OCH_3$; and $R_9$ is H, OH, Cl, $CH_3$, $CH_2CH_3$, $OCH_3$, $OCH_2CH_3$, $OCH_2CH_2CH_3$, $SCH_3$, $OCF_3$, $OCHF_2$, $OCH(CH_3)_2$, $N(CH_3)_2$, $NHCH_3$; or optionally $R_9$ and one of $R_8$ and $R_{10}$ together form 1,3-dioxolane.

Compounds of Formula I include compounds according to Formula II:

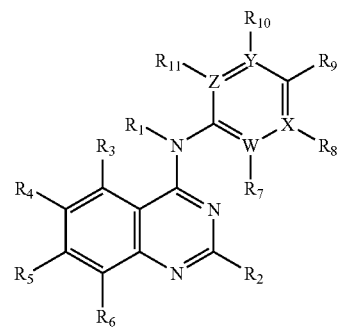

or pharmaceutically acceptable salts or solvates thereof, wherein:

$R_1$ is $C_{1-3}$ alkyl;

$R_2$ is halo, $R_{14}$, $OR_{14}$, $SR_{14}$, $NR_{15}R_{14}$, or $NR_{14}(C=O)C_{1-6}$ alkyl wherein $R_{15}$ is $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl and $R_{14}$ is H, $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl;

$R_3$, $R_4$, $R_6$-$R_8$, $R_{10}$ and $R_{11}$ are independently halo, $R_{16}$, $NR_{16}R_{17}$, $OR_{16}$, or $SR_{16}$ wherein $R_{16}$ and $R_{17}$ are independently H, $C_{1-6}$ alkyl, $C_{2-6}$ alkenyl, $C_{2-6}$ alkynyl, or $C_{1-6}$ haloalkyl provided that $R_{16}$ and $R_{17}$ are not both H;

$R_5$ is H or $C_{1-3}$ alkyl;

$R_9$ is H, halo, $R_{18}$, $OR_{18}$, $SR_{18}$, $NR_{18}R_{19}$, or optionally $R_9$ and one of $R_8$ and $R_{10}$ together form a heterocycle, wherein $R_{18}$ and $R_{19}$ are independently H, $C_{1-6}$ alkyl, $C_{2-6}$ alkenyl, $C_{2-6}$ alkynyl, or $C_{1-6}$ haloalkyl provided that $R_{18}$ and $R_{19}$ are not both H; and W, X, Y and Z are independently C or N, provided that no more than one of W, X, Y and Z are N, and when W, X, Y or Z is N, then there is no substituent at the N.

In specific embodiments of the compounds of Formula II, X or Y is N. In specific embodiments of the compounds of Formula II, W or Z is N.

In specific embodiments of the compounds of Formula II, $R_2$ is $C_{1-3}$ alkyl, halo, $C_{1-3}$ haloalkyl, $-OC_{1-3}$ alkyl, $-SC_{1-3}$ alkyl, $C_{3-8}$ heterocycle (preferably morpholino), $NR_{2a}C_{1-3}$ alkyl, $NR_{2a}(C=O)C_{1-3}$ alkyl, or $NR_{2a}$(arylalkyl) wherein $R_{2a}$ is H or $C_{1-3}$ alkyl.

In additional specific embodiments of the compounds of Formula II, $R_1$ is $CH_3$. In specific embodiments of the compounds of Formula II, $R_5$ is H. In specific embodiments of the compounds of Formula II, $R_3$, $R_4$, $R_6$-$R_8$, $R_{10}$ and $R_{11}$ are independently H, $C_{1-3}$ alkyl, halo, $NH(C_{1-3}$ alkyl), $N(C_{1-3}$ alkyl$)_2$, or $-OC_{1-3}$ alkyl.

In additional specific embodiments of the compounds of Formula II, $R_9$ is H, OH, $C_{1-3}$ alkyl, halo, $C_{1-3}$ haloalkyl, —$OC_{1-3}$ alkyl, —$SC_{1-3}$ alkyl, —$OC_{1-3}$ haloalkyl, $NR_{9a}R_{9b}$ wherein $R_{9a}$ and $R_{9b}$ are independently H or $C_{1-3}$ alkyl provided that $R_{9a}$ and $R_{9b}$ are not both H, or optionally $R_9$ and one of $R_8$ and $R_{10}$ together form a $C_{3-8}$ heterocycle (preferably 1,3-dioxolane).

In a specific embodiment of the compounds of Formula II,
$R_1$ is $CH_2CH_3$, or $CH_3$, preferably $CH_3$;
$R_2$ is $CH_2CH_3$, $CH_3$, Cl, $CH_2F$, $OCH_3$, $SCH_3$, morpholino, $NHCH_3$, $NCH_3(C=O)CH_3$, or $NHCH_2C_6H_5$;
$R_3$, $R_4$, and $R_6$ are independently H, $CH_3$, Cl, $NHCH_3$, $N(CH_3)_2$, or $OCH_3$;
$R_5$ is H;
$R_7$, $R_8$, $R_{10}$ and $R_{11}$ are independently H, F, or $OCH_3$; and
$R_9$ is H, OH, Cl, $CH_3$, $CH_2CH_3$, $OCH_3$, $OCH_2CH_3$, $OCH_2CH_2CH_3$, $SCH_3$, $OCF_3$, $OCHF_2$, $OCH(CH_3)_2$, $N(CH_3)_2$, $NHCH_3$; or optionally $R_9$ and one of $R_8$ and $R_{10}$ together form 1,3-dioxolane.

Another group of compounds of Formula I include compounds according to Formula III:

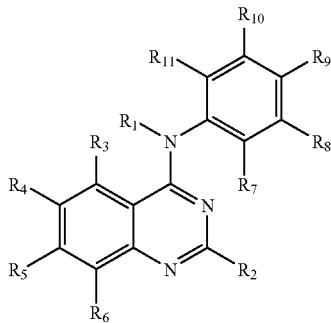

(III)

or pharmaceutically acceptable salts, or solvates thereof, wherein:
$R_1$ is $C_{1-3}$ alkyl;
$R_2$ is halo, $R_{15}$, $OR_{14}$, $SR_{14}$, $NR_{15}R_{14}$, or $NR_{14}(C=O)C_{1-6}$ alkyl wherein $R_{15}$ is $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl and $R_{14}$ is H, $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl;
$R_3$, $R_4$, $R_6$-$R_8$, $R_{10}$ and $R_{11}$ are independently halo, $R_{16}$, $NR_{16}R_{17}$, $OR_{16}$, or $SR_{16}$ wherein $R_{16}$ and $R_{17}$ are independently H, $C_{1-6}$ alkyl, $C_{2-6}$ alkenyl, $C_{2-6}$ alkynyl, or $C_{1-6}$ haloalkyl provided that $R_{16}$ and $R_{17}$ are not both H;
$R_5$ is H or $C_{1-3}$ alkyl; and
$R_9$ is H, halo, $R_{18}$, $OR_{18}$, $SR_{18}$, $NR_{18}R_{19}$, or optionally $R_9$ and one of $R_8$ and $R_{10}$ together form a heterocycle, wherein $R_{18}$ and $R_{19}$ are independently H, $C_{1-6}$ alkyl, $C_{2-6}$ alkenyl, $C_{2-6}$ alkynyl, or $C_{1-6}$ haloalkyl provided that $R_{18}$ and $R_{19}$ are not both H.

In specific embodiments of the compounds of Formula III, $R_2$ is $C_{1-3}$ alkyl, halo, $C_{1-3}$ haloalkyl, —$OC_{1-3}$ alkyl, —$SC_{1-3}$ alkyl, $C_{3-8}$ heterocycle (preferably morpholino), $NR_{2a}C_{1-3}$ alkyl, $NR_{2a}(C=O)C_{1-3}$ alkyl, or $NR_{2a}$(arylalkyl) wherein $R_{2a}$ is H or $C_{1-3}$ alkyl.

In additional specific embodiments of the compounds of Formula III, $R_1$ is $CH_3$. In specific embodiments of the compounds of Formula III, $R_5$ is H. In specific embodiments of the compounds of Formula III, $R_3$, $R_4$, $R_6$-$R_8$, $R_{10}$ and $R_{11}$ are independently H, $C_{1-3}$ alkyl, halo, $NH(C_{1-3}$ alkyl), $N(C_{1-3}$ alkyl)$_2$, or —$OC_{1-3}$ alkyl.

In additional specific embodiments of the compounds of Formula III, $R_9$ is H, OH, $C_{1-3}$ alkyl, halo, $C_{1-3}$ haloalkyl, —$OC_{1-3}$ alkyl, —$SC_{1-3}$ alkyl, —$OC_{1-3}$ haloalkyl, $NR_{9a}R_{9b}$ wherein $R_{9a}$ and $R_{9b}$ are independently H or $C_{1-3}$ alkyl provided that $R_{9a}$ and $R_{9b}$ are not both H, or optionally $R_9$ and one of $R_8$ and $R_{10}$ together form a $C_{3-8}$ heterocycle (preferably 1,3-dioxolane).

In a specific embodiment of the compounds of Formula III,
$R_1$ is $CH_2CH_3$, or $CH_3$, preferably $CH_3$;
$R_2$ is $CH_2CH_3$, $CH_3$, Cl, $CH_2F$, $OCH_3$, $SCH_3$, morpholino, $NHCH_3$, $NCH_3(C=O)CH_3$, or $NHCH_2C_6H_5$;
$R_3$, $R_4$, and $R_6$ are independently H, $CH_3$, Cl, $NHCH_3$, $N(CH_3)_2$, or $OCH_3$;
$R_5$ is H;
$R_7$, $R_8$, $R_{10}$ and $R_{11}$ are independently H, F, or $OCH_3$; and
$R_9$ is H, OH, Cl, $CH_3$, $CH_2CH_3$, $OCH_3$, $OCH_2CH_3$, $OCH_2CH_2CH_3$, $SCH_3$, $OCF_3$, $OCHF_2$, $OCH(CH_3)_2$, $N(CH_3)_2$, $NHCH_3$; or optionally $R_9$ and one of $R_8$ and $R_{10}$ together form 1,3-dioxolane.

In another specific embodiment of the compounds of Formula III,
$R_1$ is $CH_3$;
$R_2$ is $CH_3$, Cl, $OCH_3$, $NHCH_3$, or $NCH_3(C=O)CH_3$;
$R_3$-$R_6$, $R_7$, $R_8$, $R_{10}$ and $R_{11}$ are H; and
$R_9$ is $OCH_3$, $N(CH_3)_2$, or $NHCH_3$.

In the various embodiments of the above methods, preferably when $R_9$ is H then $R_8$ and $R_{10}$ are not both H or one H and the other halo. Also, in the various embodiments above, preferably when $R_9$ is H then $R_8$ and $R_{10}$ are not both H or one H and the other halo or alkyl or haloalkyl. In the various embodiments above, preferably when $R_9$ is $C_{1-6}$ alkyl, halo, or $C_{1-6}$ haloalkyl, $R_2$ is not H. Also in the various embodiments above, preferably when $R_9$ is H then $R_8$ and $R_{10}$ are not both H or one H and the other halo, and $R_2$ is not H.

In the various embodiments of the above methods of the present invention, preferably the compounds administered in the methods of the invention are able to induce caspase activation as determined by the method and under conditions (measurement at 24 hours) described in Example 61, preferably at an $EC_{50}$ no greater than 1,000 nM, more preferably at an $EC_{50}$ no greater than about 500 nM, more preferably at an $EC_{50}$ no greater than about 200 nM, more preferably at an $EC_{50}$ no greater than about 100 nM, even more preferably at an $EC_{50}$ no greater than about 50 nM, and most preferably at an $EC_{50}$ no greater than about 10 nM. Also preferred in the above methods of the invention are compounds of Formulae I-III, and pharmaceutically acceptable salts or solvates thereof, that are able to inhibit tubulin at an $IC_{50}$ of no greater than about 2,000 nM, more preferably no greater than about 1,000 nM, most preferably less than about 500 nM, as determined by methods known in the art.

In a specific embodiment of the above methods of the invention are compounds of Formulae I-III, and pharmaceutically acceptable salts or solvates thereof, that have a brain/plasma AUC ratio, as determined by the method and under conditions described in Example 62, of greater than about 5, preferably greater than about 10, and more preferably greater than about 15.

Exemplary compounds useful in the methods of the present invention are compounds provided in Examples 1-60, and pharmaceutically acceptable salts or prodrugs thereof. Specific exemplary compounds include but are not limited to:
(2-Chloro-quinazolin-4-yl)-(4-methoxy-phenyl)-methylamine;
(2-Chloro-quinazolin-4-yl)-(4-methyl-phenyl)-methylamine;

(2-Chloro-quinazolin-4-yl)-(4-chloro-phenyl)-methyl-amine;
(2-Chloro-quinazolin-4-yl)-(4-trifluoromethoxy-phenyl)-methyl-amine;
(4-Methoxy-phenyl)-methyl-(2-morpholin-4-yl-quinazolin-4-yl)-amine;
(2-Chloro-quinazolin-4-yl)-ethyl-(4-methoxy-phenyl)-amine;
(2-Chloro-quinazolin-4-yl)-(2,4-dimethoxy-phenyl)-methyl-amine;
(2-Chloro-quinazolin-4-yl)-(3-methoxy-phenyl)-methyl-amine;
(2-Methoxy-quinazolin-4-yl)-(4-methoxyphenyl)-methylamine;
(2-Fluoromethyl-quinazolin-4-yl)-(4-methoxy-phenyl)-methyl-amine;
(2-Chloro-6-methyl-quinazolin-4-yl)-(4-methoxy-phenyl)-methyl-amine;
(2-Chloro-5-methyl-quinazolin-4-yl)-(4-methoxy-phenyl)-methyl-amine;
(2-Chloro-8-methyl-quinazolin-4-yl)-(4-methoxy-phenyl)-methyl-amine;
(2,6-Dichloro-quinazolin-4-yl)-(4-methoxy-phenyl)-methyl-amine;
(4-Methoxy-phenyl)-methyl-(quinolin-4-yl)-amine;
(2-Chloro-quinazolin-4-yl)-(3,4-methylenedioxyphenyl)-methyl-amine;
(2-Chloro-quinazolin-4-yl)-(3,4-dimethoxy-phenyl)-methyl-amine;
(2-Chloro-quinazolin-4-yl)-(4-propoxy-phenyl)-methyl-amine;
(4-Methoxy-phenyl)-methyl-(2-methyl-quinazolin-4-yl)-amine hydrochloride;
(2-Ethyl-quinazolin-4-yl)-(4-methoxy-phenyl)-methyl-amine;
(2-Chloro-quinazolin-4-yl)-(2,3-dimethoxy-phenyl)-methyl-amine;
(4-Difluoromethoxy-phenyl)-(2-methyl-quinazolin-4-yl)-methyl-amine;
(3-Fluoro-4-methoxy-phenyl)-(2-methyl-quinazolin-4-yl)-methyl-amine;
(4-Isopropoxy-phenyl)-(2-methyl-quinazolin-4-yl)-methyl-amine;
(4-Ethyl-phenyl)-(2-methyl-quinazolin-4-yl)-methyl-amine;
(2,8-Dichloro-quinazolin-4-yl)-(4-methoxy-phenyl)-methyl-amine;
(2,5-Dichloro-quinazolin-4-yl)-(4-methoxy-phenyl)-methyl-amine;
(5-Methoxy-2-methyl-quinazolin-4-yl)-(4-methoxy-phenyl)-methyl-amine;
(2-Chloro-quinazolin-4-yl)-(4-ethoxy-phenyl)-methylamine;
(2-Methyl-quinazolin-4-yl)-(6-methoxy-pyridin-3-yl)-methyl-amine;
(2-Fluoro-4-methoxy-phenyl)-(2-methyl-quinazolin-4-yl)-methyl-amine;
(4-Dimethylamino-phenyl)-(2-methyl-quinazolin-4-yl)-methyl-amine;
(4-Ethoxy-phenyl)-(2-methyl-quinazolin-4-yl)-methyl-amine;
(2-Methylthio-quinazolin-4-yl)-(4-methoxy-phenyl)-methyl-amine;
(2-Methylamino-quinazolin-4-yl)-(4-methoxy-phenyl)-methyl-amine;
(2-Methylamino-quinazolin-4-yl)-(6-methoxy-pyridin-3-yl)-methyl-amine;
(5-Methoxy-pyridin-2-yl)-(2-methyl-quinazolin-4-yl)-methyl-amine;
(2-Benzylamino-quinazolin-4-yl)-(4-methoxyphenyl)-methylamine;
(2-Methyl-quinazolin-4-yl)-(4-methylamino-phenyl)-methylamine;
(2-Chloro-quinazolin-4-yl)-(4-dimethylaminophenyl)-methylamine;
(2-Methylamino-quinazolin-4-yl)-(4-dimethylaminophenyl)-methylamine;
[2-(N-Methyl-acetamido)-quinazolin-4-yl]-(4-dimethylaminophenyl)-methylamine;
(4-Methylthio-phenyl)-(2-methyl-quinazolin-4-yl)-methylamine;
(2-Dimethylamino-pyridine-5-yl)-(2-methyl-quinazolin-4-yl)-methylamine;
(4-Methoxy-phenyl)-(2-N-methylacetamido-quinazolin-4-yl)-methylamine;
(6-Dimethylamino-2-methyl-quinazolin-4-yl)-(4-methoxy-phenyl)-methylamine;
(2-Chloro-quinazolin-4-yl)-phenyl-methyl-amine;
(2-Chloro-quinazolin-4-yl)-phenyl-methyl-amine;
(2-Chloro-quinazolin-4-yl)-(2,5-dimethoxy-phenyl)-methyl-amine;
(2-Chloro-quinazolin-4-yl)-(2-methoxy-phenyl)-methyl-amine;
(2-Chloro-quinazolin-4-yl)-(4-hydroxyphenyl)-methylamine;
(2,7-Dichloro-quinazolin-4-yl)-(4-methoxy-phenyl)-methyl-amine;
(2-Chloro-7-methyl-quinazolin-4-yl)-(4-methoxy-phenyl)-methyl-amine;
and pharmaceutically acceptable salts or solvates thereof.

Unless specifically stated otherwise or indicated by a bond symbol (dash or double dash), the connecting point to a recited group will be on the right-most stated group. Thus, for example, a hydroxyalkyl group is connected to the main structure through the alkyl and the hydroxyl is a substituent on the alkyl.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$ alkyl groups mentioned above, which may be optionally substituted. Alkoxy substituents include, without limitation, halo, morpholino, amino including alkylamino and dialkylamino, and carboxy including esters thereof.

Useful alkylthio groups include sulfur substituted by one of the $C_{1-10}$ alkyl groups mentioned above, which may be optionally substituted. Also included are the sulfoxides and sulfones of such alkylthio groups.

Useful amino groups include —$NH_2$, —$NHR_x$ and —$NR_xR_y$, wherein $R_x$ and $R_y$ are $C_{1-10}$ alkyl or cycloalkyl groups, or $R_x$ and $R_y$ are combined with the N to form a ring structure, such as a piperidine, or $R_x$ and $R_y$ are combined with the N and other group to form a ring, such as a piperazine. The alkyl group may be optionally substituted.

Optional substituents on the alkyl, alkenyl, alkynyl, cycloalkyl, carbocyclic and heterocyclic groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl.

Optional substituents on the aryl, arylalkyl, arylalkenyl, arylalkynyl and heteroaryl and heteroarylalkyl groups include one or more halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy, carboxy or $C_{1-2}$ alkylenedioxy (e.g., methylenedioxy).

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon or on a nitrogen atom if the resulting compound is stable, including an oxo substituent ("=O") wherein two hydrogen atoms are replaced.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms.

Useful heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

The present invention also provides novel compounds, which are potent tubulin inhibitors, topoisomerase II inhibitors, caspase-3 activators and/or apoptosis inducers/promoters. Specifically, the novel compounds of the present invention are represented by Formulae I-III and pharmaceutically acceptable salts or solvates thereof.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts for the compounds of the present invention, include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et. al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I-III can be prepared as illustrated by the exemplary reaction in Scheme 1. Reaction of optionally substituted quinazoline-2,4-dione with phosphorylchloride produces the corresponding 2,4-dichloroquinazoline, which is reacted with an optionally substituted aniline, such as N-methyl-4-methoxy-aniline, to produce the substituted 2-chloro-4-anilino-quinazoline.

Scheme 1

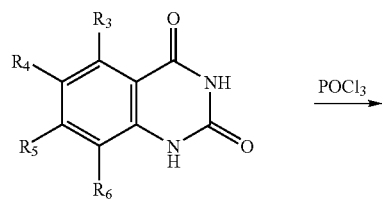

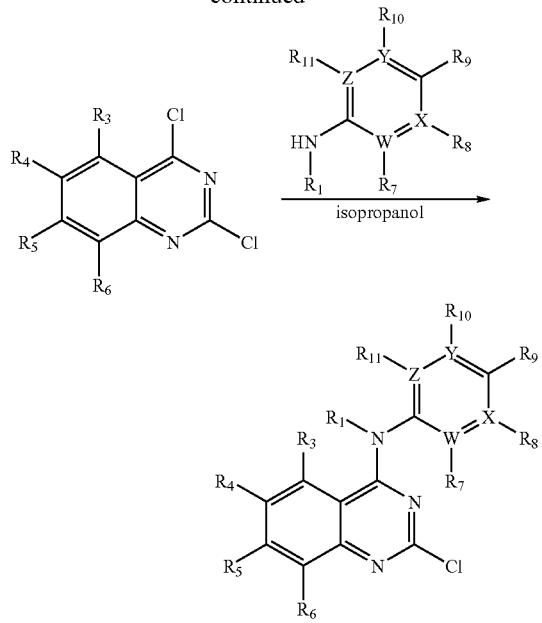

Compounds of this invention with Formulae I-III also could be prepared as illustrated by the exemplary reaction in Scheme 2. Reaction of the substituted 2-chloro-4-anilino-quinazoline with a nucleophile ($R_2$), such as hydroxylamine, in isopropanol heated by microwave produces the 2-nucleophile substituted-4-anilino-quinazoline, such as substituted hydroxylamino. Other nucleophiles that can be used in the reaction include NaOMe, $NaN_3$, NaSMe, $NH_3$, $NH_2Me$, or $NHMe_2$, and the reaction can be run at room temperature or elevated temperature.

Scheme 2

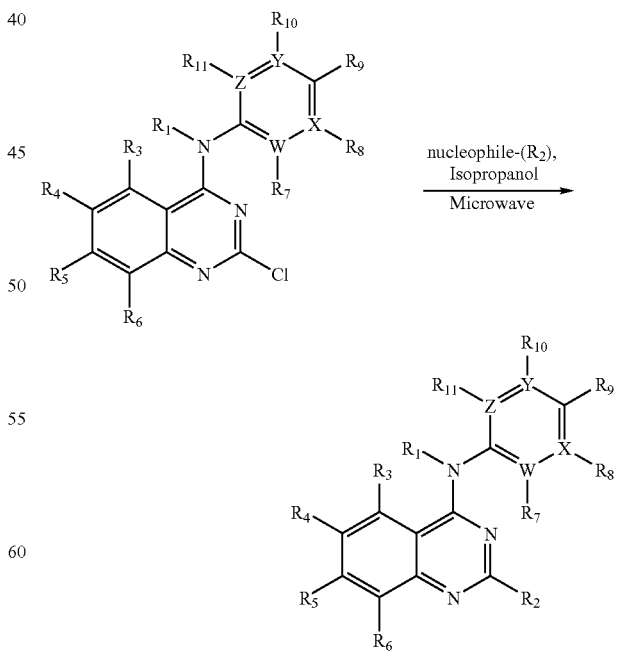

Compounds of this invention with Formulae I-III, could be prepared as illustrated by the exemplary reaction in Scheme 3. Reaction of 2,4-dichloroquinazoline with a substituted arylamine or heteroarylamine, such as a substituted pyridin-3-ylamine, produces the corresponding 4-aryl/heteroarylamino substituted 2-chloro-quinazoline, which is alkylated with a haloalkyl, such as methylated by reaction with methyl iodide in the presence of a base such as NaH, to produce the corresponding 4-N-methyl-aryl/heteroaryl-amino substituted 2-chloro-quinazoline.

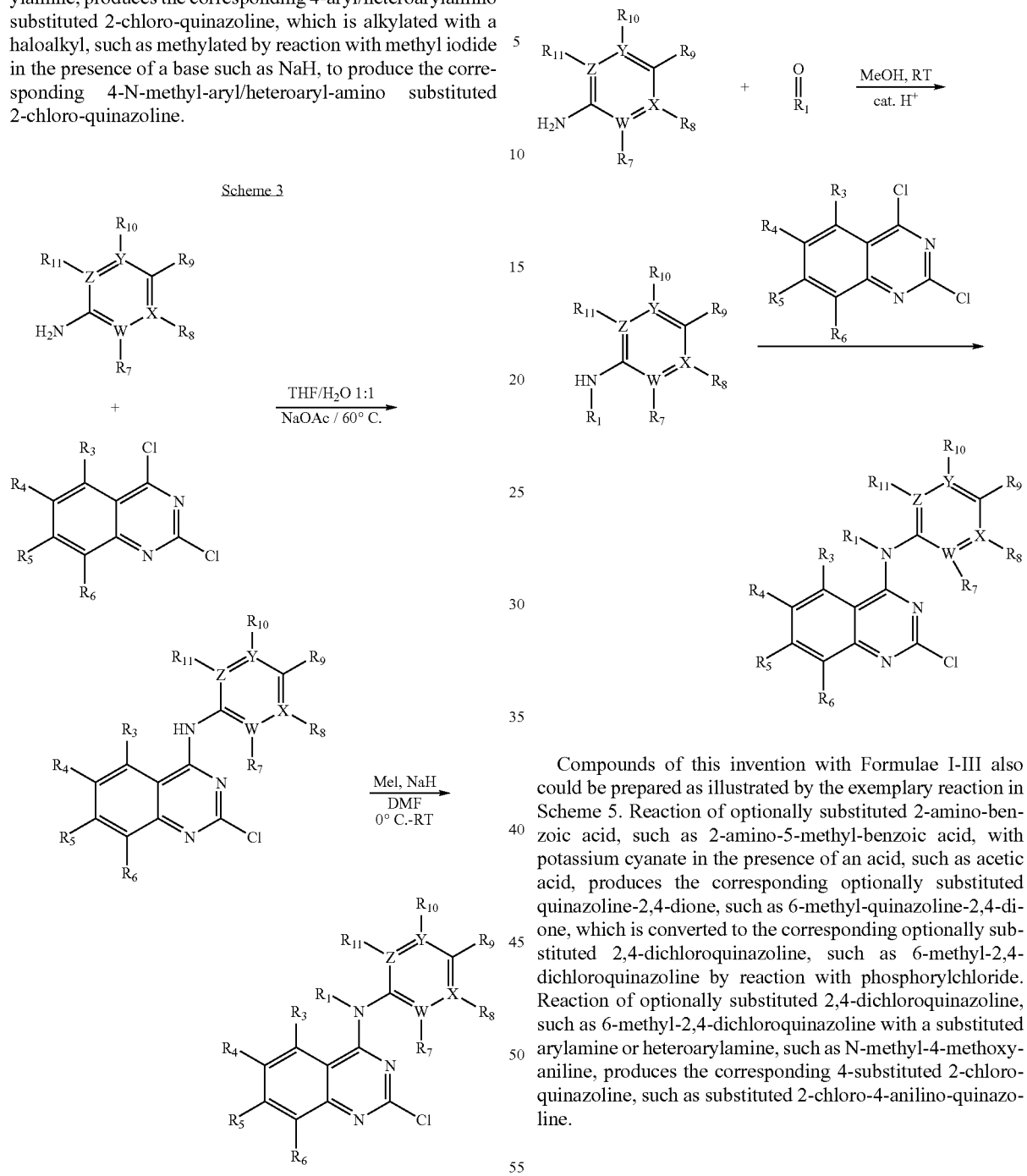

Alternatively, compounds of this invention with Formulae I-III also could be prepared as illustrated by the exemplary reaction in Scheme 4. The N-alkyl-arylamine or N-alkyl-heteroarylamine could be prepared by reaction of the arylamine or heteroarylamine with a ketone or aldehyde, such as acetone, in the presence of a reducing agent, such as NaCNBH$_3$. The N-alkyl-arylamine or N-alkyl-heteroarylamine is then reacted with optionally substituted 2,4-dichloroquinazoline to produce the corresponding 4-substituted 2-chloro-quinazoline.

Compounds of this invention with Formulae I-III also could be prepared as illustrated by the exemplary reaction in Scheme 5. Reaction of optionally substituted 2-amino-benzoic acid, such as 2-amino-5-methyl-benzoic acid, with potassium cyanate in the presence of an acid, such as acetic acid, produces the corresponding optionally substituted quinazoline-2,4-dione, such as 6-methyl-quinazoline-2,4-dione, which is converted to the corresponding optionally substituted 2,4-dichloroquinazoline, such as 6-methyl-2,4-dichloroquinazoline by reaction with phosphorylchloride. Reaction of optionally substituted 2,4-dichloroquinazoline, such as 6-methyl-2,4-dichloroquinazoline with a substituted arylamine or heteroarylamine, such as N-methyl-4-methoxy-aniline, produces the corresponding 4-substituted 2-chloro-quinazoline, such as substituted 2-chloro-4-anilino-quinazoline.

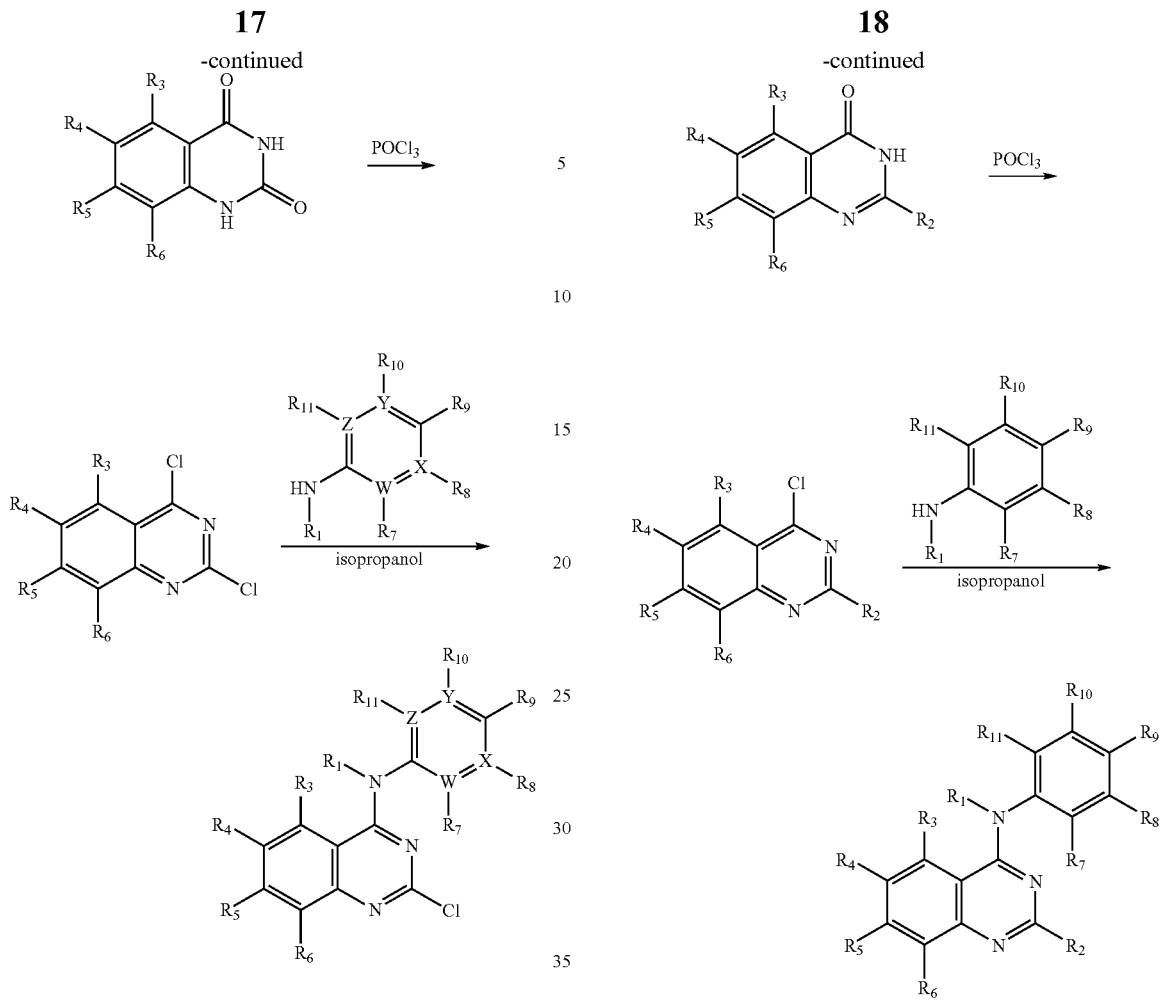

Compounds of this invention with Formulae I-III, wherein $R_2$ is an optionally substituted alkyl group, could be prepared as illustrated by the exemplary reaction in Scheme 6. Reaction of 2-amino-benzoic acid methyl ester with an optionally substituted acetonitrile, such as fluoro-acetonitrile, in the presence of HCl produces the corresponding 2-substituted quinazoline-4(3H)-one, such as 2-fluoromethyl-quinazoline-4(3H)-one, which is converted to 2-substituted 4-chloro-quinazoline, such as 4-chloro-2-fluoromethyl-quinazoline by reaction with phosphorylchloride. Reaction of 2-substituted 4-chloro-quinazoline, such as 4-chloro-2-fluoromethyl-quinazoline with a substituted aniline, such as N-methyl-4-methoxy-aniline, produces the corresponding 2-substituted 4-anilino-quinazoline, such as 2-fluoromethyl-4-anilino-quinazoline. Other substituted acetonitriles that can be used for the reaction include chloro-acetonitrile and bromo-acetonitrile, as well as acetonitrile and propionitrile.

Compounds of this invention with Formulae I-III, wherein $R_2$ is a substituted alkyl group, could also be prepared as illustrated by the exemplary reaction in Scheme 7. Reaction of a substituted 2-chloroalkyl-4-(N-alkyl-arylamine or N-alkyl-heteroarylamine)-quinazoline, such as N-methyl-2-chloromethyl-4-anilino-quinazoline, with a nucleophile, such as $NHMe_2$, produces the substituted 2-dimethylaminomethyl-4-anilino-quinazoline. Other nucleophiles that can be used in the reaction include NaOMe, $NaN_3$, NaSMe, $NH_3$, $NH_2Me$, or $NHMe_2$, and the reaction can be run at room temperature and elevated temperature.

Scheme 6

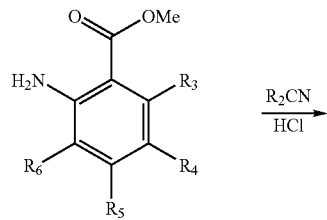

Scheme 7

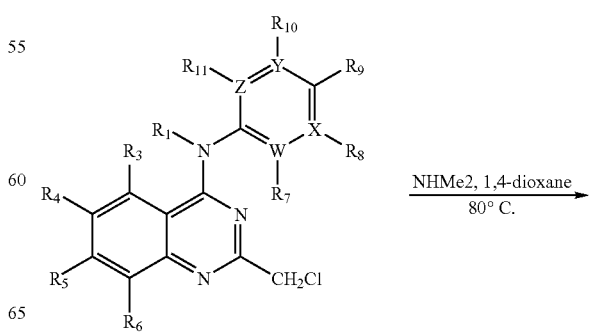

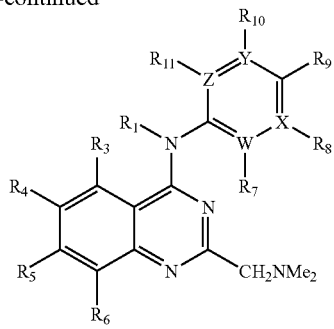

Compounds of this invention with Formulae I-III, wherein $R_1$ is a substituted alkyl, could be prepared as illustrated by the exemplary reaction in Scheme 8. For example, reaction of an optionally substituted 4-(arylamine or heteroarylamine)-quinazoline, such as 2-methyl-4-(6-methoxy-pyridin-3-ylamino)-quinazoline, with a substituted haloalkyl, such as difluoromethyl chloride, in the presence of a base such as NaH, produces the corresponding 4-(N-alkyl-arylamine or N-alkyl-heteroarylamine)-quinazoline, such as 2-methyl-$N^4$-difluoromethyl-4-(4-methoxy-pyridin-3-ylamino)-quinazoline.

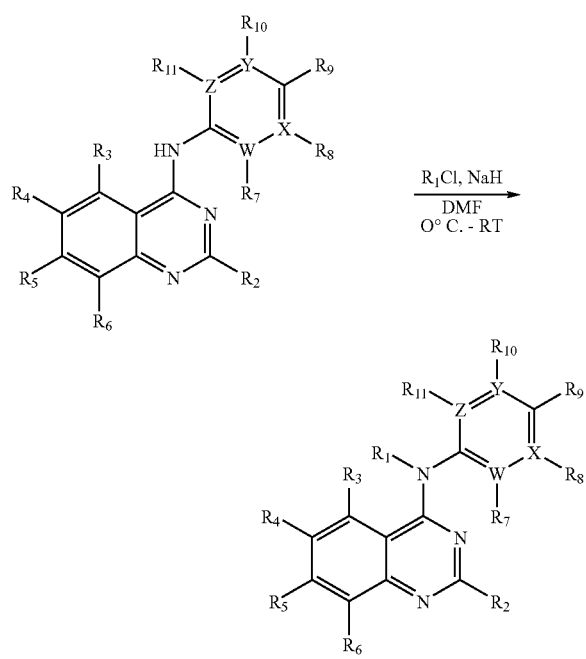

Compounds of this invention with Formula I-III, wherein $R_2$ is an alkyl group, could be prepared as illustrated by the exemplary reaction in Scheme 9. Reaction of a substituted 2-amino-benzoic acid, such as 2-amino-5-nitro-benzoic acid, with acetic anhydride, produces the corresponding substituted 2-methyl-4H-benzo[d][1,3]oxazine-4-one, such as 2-methyl-6-nitro-4H-benzo[d][1,3]oxazine-4-one, which is converted to the corresponding quinazoline-4(3H)-one, such as 2-methyl-6-nitro-quinazoline-4(3H)-one, by treatment with ammonia in dioxane. The compound is then converted to the corresponding 4-chloro-quinazoline, such as 4-chloro-2-methyl-6-nitro-quinazoline by reaction with phosphorylchloride. Reaction of the 4-chloro-quinazoline, such as 4-chloro-2-methyl-6-nitro-quinazoline with a substituted arylamine or heteroarylamine, such as N-methyl-4-methoxy-aniline, produces the corresponding 4-(arylamino or heteroarylamino)-quinazoline, such as substituted 2-methyl-6-nitro-4-anilino-quinazoline. Other substituted 2-amino-benzoic acid that can be used for the reaction include 2-amino-4-nitro-benzoic acid, 2-amino-5-chloro-benzoic acid.

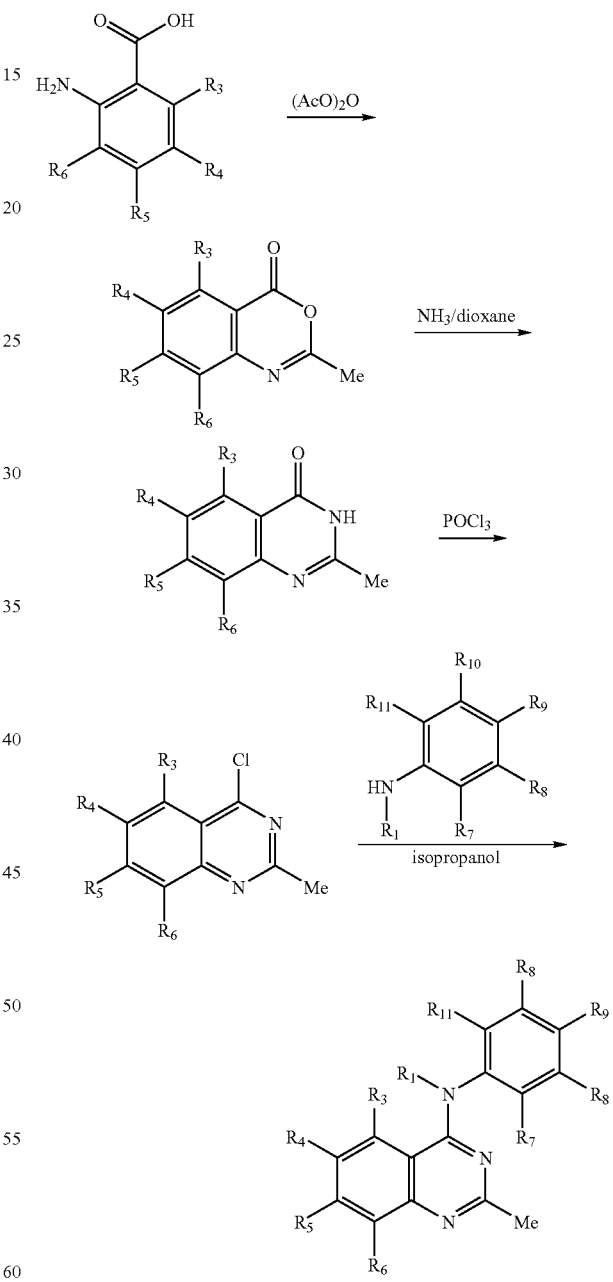

Compounds substituted with a nitro group can be reduced by hydrogenation under $H_2$ with Pd to produce the amino compound, which can be converted to the azido compounds by diazotization followed by treatment with $NaN_3$.

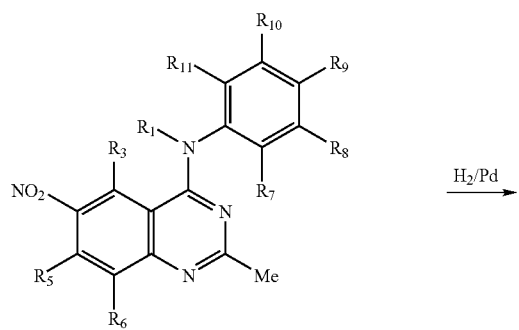
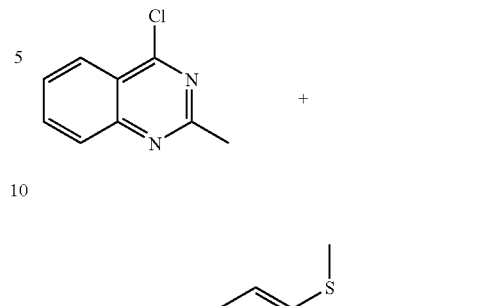
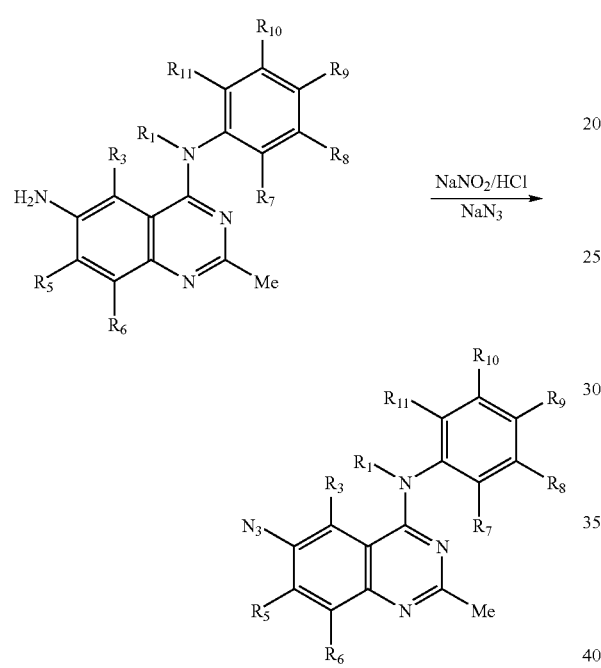
Additional exemplary compounds may be synthesized according to the synthesis schemes below:
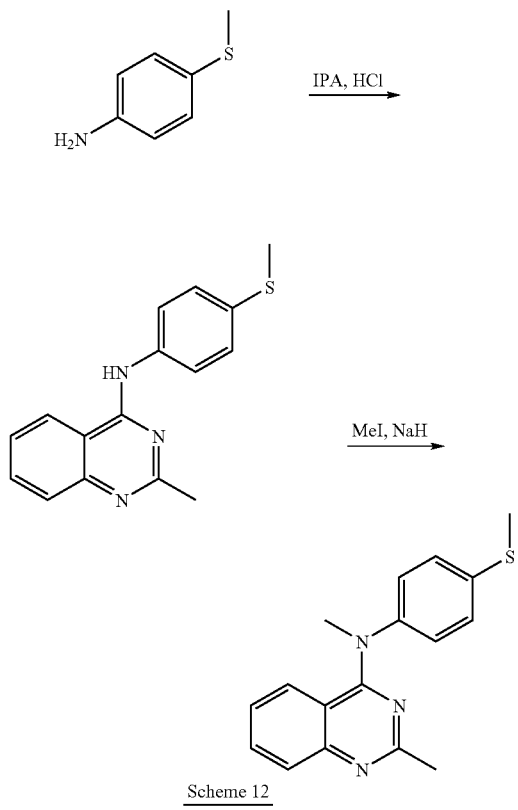
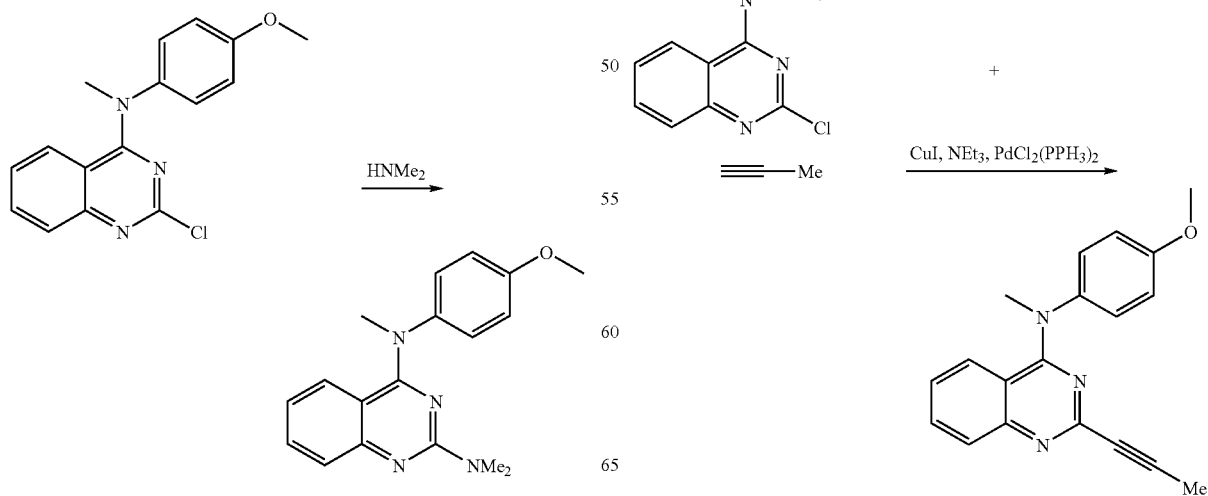

-continued
Scheme 13

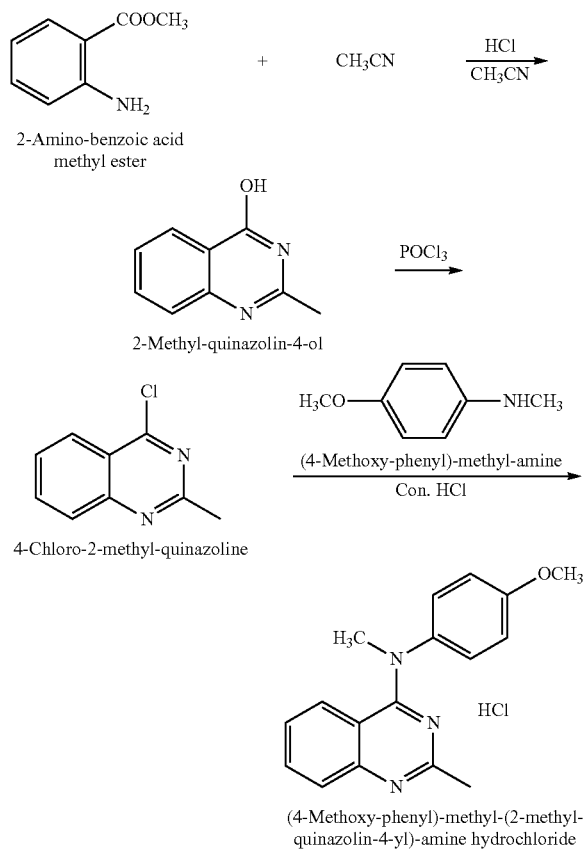

Compounds having Formulae I-III are activators of caspases and inducers of apoptosis. Compounds having Formulae I-III are also inhibitors of tubulin polymerization. Therefore, these compounds are useful in treating diseases that are responsive to activating caspases, inducing apoptosis, or inhibiting tubulin. For example, these compounds are useful in a variety of clinical conditions in which there is uncontrolled cell growth and spread of abnormal cells, such as in the case of cancer.

Another important aspect of the present invention is the surprising discovery that compounds having Formulae I-III are able to achieve adequate exposure to the brain and CNS to be effective as treatment and/or prophylaxis for diseases and disorders of the brain and CNS. In particular, the invention includes a method of treating diseases of the brain and CNS that are responsive to therapy by inducing apoptosis, activating caspases, inhibiting tubulin and/or topoisomerase in the brain. Such diseases include, for example, brain and spinal cord tumors.

Brain tumors can be generally classified as either primary brain tumors or metastatic brain tumors. Brain tumors are often further classified by cell type, morphology, cytogenetics, molecular genetics, immunologic markers, and/or a combination thereof. For example, brain tumors may be classified as neuroepithelial tumors (e.g. glial tumors, neuronal and mixed neuronal-glial tumors, and nonglial tumors), meningeal tumors, germ cell tumors, tumors of the sellar region, primary CNS lymphoma, tumors of peripheral nerves that affect the CNS, tumors of uncertain histogenesis, and metastatic tumors. A classification of brain tumors by The World Health Organization categorizes CNS tumors according to a malignancy scale based on histological features of the tumor (see Kleihues et al., *Brain Pathol* 3:255-268 (1993).

The most common types of primary brain tumors are anaplastic astrocytomas and glioblastomas, which account for approximately 38% of primary brain tumors; and meningiomas and other mesenchymal tumors, which account for approximately 27% of primary brain tumors. (see, Levin et al., *Neoplasms of the central nervous system*. In DeVita, et al., eds., *Cancer: Principles and Practice of Oncology*, Sixth Edition, Lippincott Williams & Wilkins, Philadelphia (2001), pp. 2100-2160). Other common primary brain tumors include pituitary tumors, schwannomas, CNS lymphoma, oligodendrogliomas, ependymomas, low-grade astrocytomas, and medulloblastomas. Additional specific primary brain tumors include, astocytic tumors, pilocytic astrocytomas, diffuse astrocytomas, pleomorphic xanthoastrocytomas, subependymal giant cell astrocytomas, oligodendroglial tumors, olodendrogliomas, anaplastic oligodendrogliomas, oligoastrocytomas, anaplastic oligoastrocytomas, myxopapillary ependymomas, subependymomas, ependymomas, anaplastic ependymomas, astroblastomas, chordoid gliomas of the third ventricle, gliomatosis cerebris, gangliocytomas, desmoplastic infantile astrocytomas, desmoplastic infantile gangliogliomas, dysembryoplastic neuroepithelial tumors, central neurocytomas, cerebellar liponeurocytomas, paragangliomas, ependymoblastomas, medulloblastomas, supratentorial primitive neuroectodermal tumors, choroids plexus papilloma, pineocytomas, pineoblastomas, pineal parenchymal tumors of intermediate differentiation, hemangiopericytomas, melanocytic lesions, germ cell tumors, tumors of the sellar region, craniopharyngioma, capillary hemangioblastoma, and primary CNS lymphoma.

Metastatic brain tumors outnumber primary brain tumors by at least 10 to 1 and typically occur as a result of primary lung, breast, melanoma, or colon cancers metastasizing to the brain (Patchell R A, *Cancer Treat. Rev.* 29:533-540 (2003)). Cancers metastasizing to the brain result in multiple brain metastases in over 70% of cases (Patchell R A, *Cancer Treat. Rev.* 29:533-540 (2003)). And thus are not typically treated by surgery. However, chemotherapy is indicated to play a role in the treatment of patients with brain metastases from chemosensitive tumors (Patchell R A, *Cancer Treat. Rev.* 29:533-540 (2003). Thus, the present invention includes a therapeutic method of treating brain cancer, including primary brain neoplasms and brain metasases, comprising administering to an animal an effective amount of a compound of Formulae I-III, or a pharmaceutically acceptable salt or prodrug thereof.

In one embodiment, the invention provides a method of reducing the size or slowing the growth of brain neoplasms. Reductions in size and/or growth of neoplasms may be measured by the Response Evaluation Criteria in Solid Tumors (RECIST) Guidelines (see Therasse et al. *J. Nat. Cancer Institute* 92:205-216 (2000), herein incorporated by reference in its entirety). For example, the method may reduce the average size of lesions in patients by about 30% or more as measured at four weeks post-treatment by identifying up to 5 lesions per organ and 10 lesions in total, and determining the reduction in length at the longest diameter of the lesion. In yet another embodiment, the invention provides a method for improving the survival of patients with or at risk of forming brain tumors. The methods comprise administering to a subject mammal in need of the treatment a therapeutically effective amount of a compound of the present invention.

The present invention also includes a therapeutic method comprising administering to an animal an effective amount of a compound, or a pharmaceutically acceptable salt or prodrug of said compound of Formulae I-III, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

In certain embodiments of the therapeutic methods of the present invention, the compounds of Formulae I-III have a calculated polar surface area of less than about 100 or less then about 80 square Angstroms. As used herein, "calculated polar surface area" is determined using the Fast Polar Surface Area two-dimensional polar surface area predictor software, available from Accelerys® (San Diego, Calif.).

Another aspect of the present invention is to provide a pharmaceutical composition, containing an effective amount of a compound of Formulae I-III, or a pharmaceutically acceptable salt of said compound, in admixture with one or more pharmaceutically acceptable carriers or diluents.

In one embodiment, a pharmaceutical composition comprising a compound of Formulae I-III disclosed herein, or a pharmaceutically acceptable salt of said compound, in combination with a pharmaceutically acceptable vehicle is provided.

Preferred pharmaceutical compositions comprise compounds of Formulae I-III, and pharmaceutically acceptable salts, esters, or prodrugs thereof, that are able to induce caspase activation as determined by the method described in Example 61, preferably at an $EC_{50}$ no greater than 1,000 nM, more preferably at an $EC_{50}$ no greater than 500 nM, more preferably at an $EC_{50}$ no greater than 200 nM, more preferably at an $EC_{50}$ no greater than 100, and most preferably at an $EC_{50}$ no greater than 10 nM.

Another embodiment of the present invention is directed to a composition effective to inhibit neoplasia comprising a compound, or a pharmaceutically acceptable salt or prodrug of said compound of Formulae I-III, which functions as a caspase cascade activator and inducer of apoptosis or inhibitor of tubulin polymerization, in combination with at least one known cancer chemotherapeutic agent, or a pharmaceutically acceptable salt of said agent. Examples of known cancer chemotherapeutic agents which may be used for combination therapy include, but not are limited to alkylating agents, such as busulfan, cisplatin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; EGFR inhibitors, such as Iressa® (gefitinib) and Tarceva® (erlotinib); proteosome inhibitors; antibodies, such as campath, Herceptin® (trastuzumab), Avastin® (bevacizumab), or Rituxan® (rituximab). Other known cancer chemotherapeutic agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

It has been reported that alpha-1-adrenoceptor antagonists, such as doxazosin, terazosin, and tamsulosin can inhibit the growth of prostate cancer cell via induction of apoptosis (Kyprianou, N., et al., Cancer Res 60:4550-4555, (2000)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known alpha-1-adrenoceptor antagonist, or a pharmaceutically acceptable salt of said agent. Examples of known alpha-1-adrenoceptor antagonists, which can be used for combination therapy include, but are not limited to, doxazosin, terazosin, and tamsulosin.

It has been reported that sigma-2 receptors are expressed in high densities in a variety of tumor cell types (Vilner, B. J., et al., Cancer Res. 55: 408-413 (1995)) and that sigma-2 receptor agonists, such as CB-64D, CB-184 and haloperidol activate a novel apoptotic pathway and potentiate antineoplastic drugs in breast tumor cell lines. (Kyprianou, N., et al., Cancer Res. 62:313-322 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known sigma-2 receptor agonist, or a pharmaceutically acceptable salt of said agonist. Examples of known sigma-2 receptor agonists which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., *Int. J. Cancer* 97:746-750 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known HMG-CoA reductase inhibitor, or a pharmaceutically acceptable salt of said agent. Examples of known HMG-CoA reductase inhibitors, which can be used for combination therapy include, but are not limited to, lovastatin, simvastatin, pravastatin, fluvastatin, atorvastatin and cerivastatin.

It has been reported that HIV protease inhibitors, such as indinavir or saquinavir, have potent anti-angiogenic activities and promote regression of Kaposi sarcoma (Sgadari, C., et al., *Nat. Med.* 8:225-232 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known HIV protease inhibitor, or a pharmaceutically acceptable salt of said agent. Examples of known HIV protease inhibitors, which can be used for combination therapy include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., *Cancer Chemother. Pharmacol.* 43:145-150 (1999)). 4HPR also was reported to have good activity in combination with gamma-radiation on bladder cancer cell lines (Zou, C., et al., *Int. J. Oncol.* 13:1037-1041 (1998)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known retinoid and synthetic retinoid, or a pharmaceutically acceptable salt of said agent. Examples of known retinoids and synthetic retinoids, which can be used for combination therapy include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., *Leukemia* 16:433-443 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known proteasome inhibitor, or a pharmaceutically acceptable salt of said agent. Examples of known proteasome inhibitors, which can be used for combination therapy include, but are not limited to, lactacystin, MG-132, and PS-341.

It has been reported that tyrosine kinase inhibitors, such as STI571 (Gleevec® (imatinib mesylate)), have potent synergetic effect in combination with other anti-leukemic agents, such as etoposide (Liu, W. M., et al. *Br. J. Cancer* 86:1472-1478 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known tyrosine kinase inhibitor, or a pharmaceutically acceptable salt of said agent. Examples of known tyrosine kinase inhibitors, which can be used for combination therapy include, but are not limited to, Gleevec® (imatinib mesylate), ZD1839 Iressa® (gefitinib), SH268, genistein, CEP2563, SU6668, SU11248, and EMD121974.

It has been reported that prenyl-protein transferase inhibitors, such as farnesyl protein transferase inhibitor R115777, possess preclinical antitumor activity against human breast cancer (Kelland, L. R., et. al., *Clin. Cancer Res.* 7:3544-3550 (2001)). Synergy of the protein farnesyltransferase inhibitor SCH66336 and cisplatin in human cancer cell lines also has been reported (Adjei, A. A., et al., *Clin. Cancer. Res.* 7:1438-1445 (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of said agent. Examples of known prenyl-protein transferase inhibitors, which can be used for combination therapy include, but are not limited to, R115777, SCH66336, L-778, 123, BAL9611 and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., *Clin. Cancer Res.* 7:4209-4219, (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known cyclin-dependent kinase inhibitor, or a pharmaceutically acceptable salt of said agent. Examples of known cyclin-dependent kinase inhibitors, which can be used for combination therapy include, but are not limited to, flavopiridol, UCN-01, roscovitine and olomoucine.

It has been reported that in preclinical studies COX-2 inhibitors were found to block angiogenesis, suppress solid tumor metastases, and slow the growth of implanted gastrointestinal cancer cells (Blanke, C. D., *Oncology (Huntingt)* 16(No. 4 Suppl. 3):17-21 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known COX-2 inhibitor, or a pharmaceutically acceptable salt of said inhibitor. Examples of known COX-2 inhibitors which can be used for combination therapy include, but are not limited to, celecoxib, valecoxib, and rofecoxib.

Another embodiment of the present invention is directed to a composition effective to inhibit neoplasia comprising a bioconjugate of a compound described herein, which functions as a caspase cascade activator and inducer of apoptosis or inhibitor of tubulin polymerization, in bioconjugation with at least one known therapeutically useful antibody, such as Herceptin® (trastuzumab) or Rituxan® (rituximab), growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® (trastuzumab) or Rituxan® (rituximab).

Similarly, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of a compound described herein, which functions as a caspase cascade activator and inducer of apoptosis or inhibitor of tubulin polymerization. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I-III, which functions as a caspase cascade activator and inducer of apoptosis, is an effective treatment for autoimmune diseases.

Psoriasis is a chronic skin disease that is characterized by scaly red patches. Psoralen plus ultraviolet A (PUVA) is a widely used and effective treatment for psoriasis vulgarism Coven, et al., *Photodermatol. Photoimmunol. Photomed.* 15:22-27 (1999), reported that lymphocytes treated with psoralen 8-MOP or TMP and UVA, displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I-III, which functions as a caspase cascade activator and inducer of apoptosis, is an effective treatment for hyperproliferative skin diseases, such as psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114:119-128 (1998), found that although RA synovial cells could die via apoptosis through a Fas/FasL pathway, apoptosis of synovial cells was inhibited by proinflammatory cytokines present within the synovium. Wakisaka, et al. also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-III, which functions as a caspase cascade activator and inducer of apoptosis, is an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-III, which functions as a caspase cascade activator and inducer of apoptosis, is an effective treatment for inflammation.

Caspase cascade activators and inducers of apoptosis may also be a desirable therapy in the elimination of pathogens, such as HIV, Hepatitis C and other viral pathogens. The long lasting quiecence, followed by disease progression, may be explained by an anti-apoptotic mechanism of these pathogens leading to persistent cellular reservoirs of the virions. It has been reported that HIV-1 infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1-infected asymptomatic individuals (Chinnaiyan, A., et al., *Nat. Med.* 3:333 (1997)). Therefore, apoptosis serves as a beneficial host mechanism to limit the spread of HIV and new therapeutics using caspase/apoptosis activators are useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al. *Hepatology* 3:656-64 (2000)). Therefore, apoptosis inducers are useful as therapeutics for HIV, HCV, HBV, and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with anti-proliferative properties are currently under clinical investigation, including actinomycin D, rapamycin or paclitaxel coated stents (Regar E., et al., *Br. Med. Bull.* 59:227-248 (2001)). Therefore, apoptosis inducers, which are antiproliferative, are useful as therapeutics for the prevention or reduction of in-stent restenosis.

Compounds of the present invention are potent and highly efficacious activators of caspase-3, inhibitors of tubulin polymerization, and inhibitors of topoisomerase even in drug resistant cancer cells, which enables these compounds to inhibit the growth and proliferation of drug resistant cancer cells, and to cause apoptosis and cell death in the drug resistant cancer cells. Specifically, the compounds of the present invention are not substrates for the MDR transporters such as Pgp-1 (MDR-1), MRP-1 and BCRP. This is particularly surprising in view of the fact that almost all of the commercially available tubulin-interacting chemotherapeutics are substrates for multidrug resistance transporters (MDRs).

Multidrug resistance is the major cause of chemotherapy failure. Drug resistance is typically caused by ATP-dependent efflux of drug from cells by ATP-binding cassette (ABC) transporters. In particular, the ABC transporters ABCB1 (MDR-1, P glycoprotein); ABCC1 (MRP1); and ABCG2 (BCRP, MXR) are typically over-expressed in drug resistant tumors and thus are implicated in drug resistance. In comparison to most standard anti-cancer drugs, which are not effective in killing drug resistant cancer cells, the compounds of the present invention are effective in killing drug resistant cancer cells. Therefore, compounds of this invention are useful for the treatment of drug resistant cancer.

Thus, another aspect of the present invention is the application of the methods and compounds of the present invention as described above to tumors that have acquired resistance to other anticancer drugs. In one embodiment, a compound of the present invention is administered to a cancer patient who has been treated with another anti-cancer drug. In another embodiment, a compound of the present invention is administered to a patient who has been treated with and is not responsive to another anti-cancer drug or developed resistance to such other anti-cancer compound. In another embodiment, a compound of the present invention is administered to a patient who has been treated with another anti-cancer drug and is refractory to said other anti-cancer drug. The compounds of the present invention can be used in treating cancer in a patient who is not responsive or is resistant to any other anti-cancer agent. Examples of such other anti-cancer agent may include alkylating agents, antimitotic agents, topo I inhibitors, topo II inhibitors, RNA/DNA antimetabolites, EGFR inhibitors, angiogenesis inhibitors, tubulin inhibitors (e.g., vinblastine, Taxol® (paclitaxel), and analogues thereof), proteosome inhibitors, etc., some of the exemplary compounds of which are provided above and are general known in the art, e.g., melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine. The compounds can be used in treating patients having any type of diseases responsive to the inhibition of tubulin or inhibition of topoisomerase (including but not limited to the types of cancer described above) who are not responsive or become resistant to another therapeutic agent, e.g., another anti-cancer agent.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated. Preferably, approximately 0.01 to approximately 10 mg/kg of body weight is orally administered. For intramuscular injection, the dose is generally approximately one-half of the oral dose. For example, a suitable intramuscular dose would be approximately 0.0025 to approximately 25 mg/kg of body weight, and most preferably, from approximately 0.01 to approximately 5 mg/kg of body weight. If a known cancer chemotherapeutic agent is also administered, it is administered in an amount that is effective to achieve its intended purpose. The amounts of such known cancer chemotherapeutic agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 10 mg, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, and also preparations that may be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the compounds of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which may be used orally include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which may be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

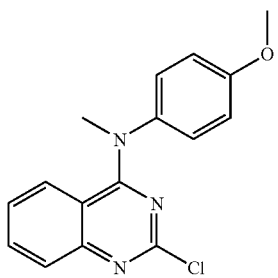

(2-Chloro-quinazolin-4-yl)-(4-methoxy-phenyl)-methyl-amine a) 2,4-Dichloroquinazoline: A suspension of 2,4-quinazolinedione (5.0 g, 30.8 mmol) in neat phosphorylchloride (50 mL) was heated under reflux for 18 h. The reaction mixture was concentrated under vacuum. The crude product was purified by chromatography (Silica gel) using ethyl acetate and hexane (1:4) to give 2,4-dichloroquinazoline as white solid (4.8 g, 96%). $^1$H NMR (CDCl$_3$): 8.29 (ddd, J=8.4, 2.1 and 0.9 Hz, 1H), 8.04-8.00 (m, 2H), 7.75 (ddd, J=8.1, 4.8 and 3.0 Hz, 1H).

b) (2-Chloro-quinazolin-4-yl)-(4-methoxy-phenyl)-methyl-amine: A solution of 2,4-dichloroquinazoline (300 mg, 1.51 mmol) and 4-methoxy-N-methylaniline (248 mg, 1.81 mmol) in 5 ml isopropanol with a drop of concentrated HCl was stirred at room temperature for 8 h. White precipitates were observed in the reaction mixture. The reaction was filtered, and the solid was washed with isopropanol, and dried under vacuum to give white powder (260 mg, 87%). $^1$H NMR (CDCl$_3$): 8.66 (dd, J=8.4 and 0.9 Hz, 1H), 7.75 (ddd, J=8.1, 7.5 and 0.9 Hz, 1H), 7.26-7.19 (m, 3H), 7.14 (ddd, J=8.1, 7.5, 0.9 Hz, 1H), 7.06 (dd, J=6.9 and 2.4 Hz, 2H), 6.75 (d, J=8.7 Hz, 1H), 3.91 (s, 3H), 3.81 (s, 3H).

EXAMPLE 2

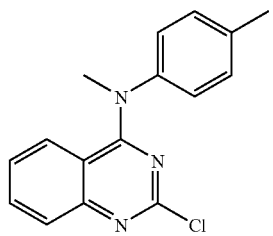

(2-Chloro-quinazolin-4-yl)-(4-methyl-phenyl)-methyl-amine

The title compound was prepared from 2,4-dichloroquinazoline (250 mg, 1.25 mmol) and 4-methyl-N-methylaniline (196 mg, 1.43 mmol) by a procedure similar to example 1b and was isolated as white powder (210 mg, 84%). $^1$H NMR (CDCl$_3$): 8.69 (d, J=8.4 Hz, 1H), 7.75 (dd, J=8.1 and 7.5 Hz, 1H), 7.39 (d, J=7.8 Hz, 2H), 7.25 (d, J=7.8 Hz, 2H), 7.13 (d, J=8.2 Hz, 1H), 6.74 (d, J=8.7 Hz, 1H), 3.81 (s, 3H), 2.49 (s, 3H).

EXAMPLE 3

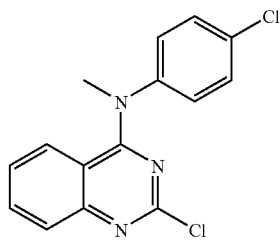

(2-Chloro-quinazolin-4-yl)-(4-chloro-phenyl)-methyl-amine

The title compound was prepared from 2,4-dichloroquinazoline (60 mg, 0.302 mmol) and 4-chloro-N-methylaniline (50 mg, 0.332 mmol) by a procedure similar to example 1b and was isolated as white powder (30 mg, 50%). $^1$H NMR (CDCl$_3$): 8.66 (d, J=8.4 Hz, 1H), 7.78 (ddd, J=8.1, 7.5 and 2.4 Hz, 1H), 7.57 (d, J=8.7 Hz, 2H), 7.28 (d, J=8.7 Hz, 2H), 7.19 (ddd, J=8.1, 7.5 and 2.4 Hz, 1H), 6.79 (d, J=8.4 Hz, 1H), 3.83 (s, 3H).

EXAMPLE 4

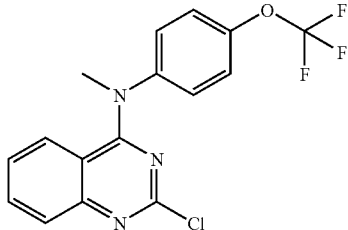

(2-Chloro-quinazolin-4-yl)-(4-trifluoromethoxy-phenyl)-methyl-amine

The title compound was prepared from 2,4-dichloroquinazoline (50 mg, 0.251 mmol) and 4-trifluoromethoxy-N-methylaniline (20 μL, 0.302 mmol) by a procedure similar to example 1b and was isolated as white powder (22 mg, 44%). $^1$H NMR (CDCl$_3$): 7.93 (dd, J=8.4, and 0.6 Hz, 1H), 7.61 (ddd, J=8.4, 4.5 and 1.2 Hz, 1H), 7.29-7.22 (m, 4H), 7.06 (ddd, J=8.4, 4.5 and 1.2 Hz, 1H), 6.91 (d, J=8.7 Hz, 1H), 3.65 (s, 3H).

EXAMPLE 5

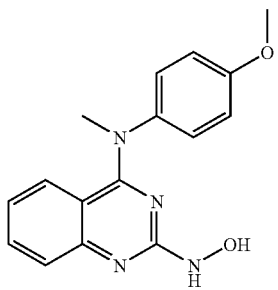

N$^2$-Hydroxyl-N$^4$-(4-methoxy-phenyl)-N$^4$-methyl-quinazoline-2,4-diamine

A mixture of (2-chloro-quinazolin-4-yl)-(4-methoxy-phenyl)-methyl-amine (15 mg, 0.050 mmol) and hydroxylamine hydrochloride (6.7 mg, 0.10 mmol) in isopropanol was heated by microwave at 130° C. for 20 min. The solvent was evaporated under reduced pressure. The product was isolated by preparative TLC as white solid (6 mg, 40%) using acetone:hexane (1:1) as eluent. $^1$H NMR (CDCl$_3$): 7.65 (d, J=8.4 Hz, 1H), 7.47 (ddd, J=8.4, 6.9 and 1.8 Hz, 1H), 7.08 (d, J=8.7 Hz, 2H), 6.94 (d, J=8.7 Hz, 2H), 6.88-6.75 (m, 2H), 3.86 (s, 3H), 3.48 (s, 3H).

EXAMPLE 6

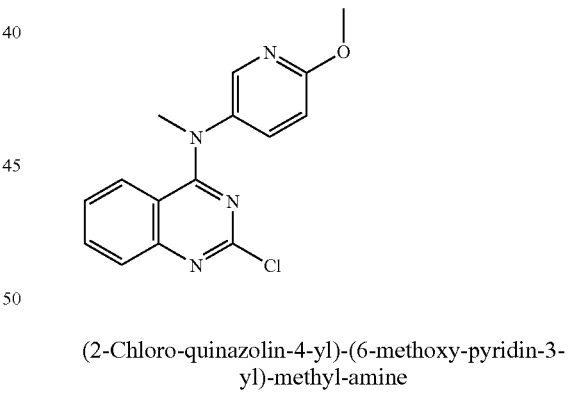

(4-Methoxy-phenyl)-methyl-(2-morpholin-4-yl-quinazolin-4-yl)-amine

The title compound was prepared from (2-chloro-quinazolin-4-yl)-(4-methoxy-phenyl)-methyl-amine (15 mg, 0.050 mmol) and morpholine (30 μL) by a procedure similar to example 5 and was isolated as white powder (10 mg, 66%). $^1$H NMR (CDCl$_3$): 7.46 (d, J=8.4 Hz, 1H), 7.35 (ddd, J=8.4, 6.6 and 1.5 Hz, 1H), 7.13-7.07 (m, 2H), 6.91-6.85 (m, 3H), 6.67 (ddd, J=8.4, 6.6 and 1.5 Hz, 1H), 3.94-3.90 (m, 4H), 3.85-3.81 (m, 7H), 3.52 (s, 3H).

EXAMPLE 7

(2-Chloro-quinazolin-4-yl)-(6-methoxy-pyridin-3-yl)-methyl-amine

To a solution of (2-chloro-quinazolin-4-yl)-(6-methoxy-pyridin-3-yl)-amine (19.4 mg, 0.068 mmol) in 1 mL of DMF cooled at 0° C. was added methyl iodide (100 uL, 1.61 mmol), followed by sodium hydride (60% oil suspension, 5 mg, 0.13 mmol). The mixture was stirred at 0° C. for 1 h, then allowed to warm to room temperature and stirred for 1 h. The reaction mixture was quenched by adding 50 uL of water, diluted with 25 mL of ethyl acetate, washed with water (25 mL×3), saturated NaCl, dried over anhydrous MgSO$_4$, filtered and concentrated. The residue was purified by chromatography (20% ethyl acetate/hexanes) to give the title compound (14.3 mg, 0.048 mmol, 70%). $^1$H NMR (CDCl$_3$) 8.06 (d, J=2.7 Hz, 1H), 7.57-7.79 (m, 1H), 7.60 (ddd, J=8.1, 6.6 and 1.2 Hz, 1H), 7.44

(dd, J=8.7 and 2.7 Hz, 1H), 7.09 (ddd, J=8.1, 6.6 and 1.2 Hz, 1H), 6.99-7.02 (m, 1H), 6.82 (dd, J=8.7 and 0.6 Hz, 1H), 3.97 (s, 3H), 3.61 (s, 3H).

EXAMPLE 8

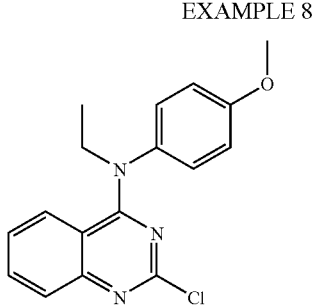

(2-Chloro-quinazolin-4-yl)-ethyl-(4-methoxy-phenyl)-amine

The title compound was prepared from (2-chloro-quinazolin-4-yl)-(4-methoxy-phenyl)-amine and ethyl iodide by a procedure similar to example 7 (58% yield). $^1$H NMR (CDCl$_3$): 7.69-7.72 (m, 1H), 7.53 (ddd, J=8.1, 6.9 and 1.5 Hz, 1H), 7.09-7.14 (m, 2H), 6.94-6.70 (m, 3H), 6.83-6.87 (m, 1H), 4.13 (q, J=7.2 Hz, 2H), 3.87 (s, 1H), 1.30 (t, J=6.9 Hz, 3H).

EXAMPLE 9

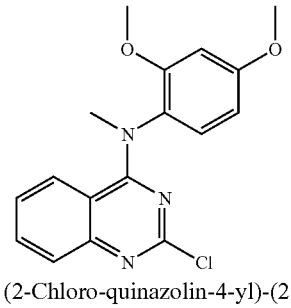

(2-Chloro-quinazolin-4-yl)-(2,4-dimethoxy-phenyl)-methyl-amine

The title compound was prepared from (2-chloro-quinazolin-4-yl)-(2,4-dimethoxy-phenyl)-amine and methyl iodide by a procedure similar to example 7 (91% yield). $^1$H NMR (CDCl$_3$): 7.70-7.73 (m, 1H), 7.54 (ddd, J=8.7, 6.3 and 2.1 Hz, 1H), 7.10 (d, J=8.7 Hz, 1H), 6.93-7.23 (m, 2H), 6.50-6.57 (m, 2H), 3.87 (s, 3H), 3.67 (s, 3H), 3.52 (s, 3H).

EXAMPLE 10

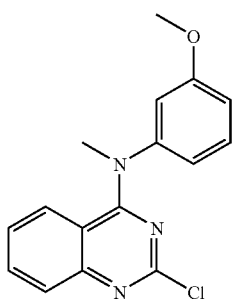

(2-Chloro-quinazolin-4-yl)-(3-methoxy-phenyl)-methyl-amine

The title compound was prepared from (2-chloro-quinazolin-4-yl)-(3-methoxy-phenyl)-amine and methyl iodide by a procedure similar to example 7 (60% yield). $^1$H NMR (CDCl$_3$): 7.74-7.76 (m, 1H), 7.57 (ddd, J=8.4, 6.0 and 1.8 Hz, 1H), 7.32 (t, J=7.8 Hz, 1H), 6.98-7.03 (m, 2H), 6.89 (dd, J=8.1 and 2.4 Hz, 1H), 6.75-6.81 (m, 2H), 3.65 (s, 3H), 3.37 (s, 3H).

EXAMPLE 11

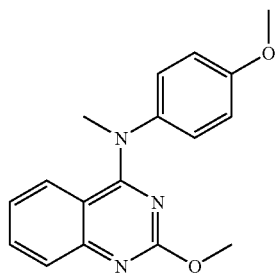

(2-methoxy-quinazolin-4-yl)-(4-methoxyphenyl)-methylamine

To a solution of (2-chloro-quinazolin-4-yl)-(4-methoxyphenyl)-methyl-amine (50 mg, 0.167 mmol) in 2 ml methanol was added sodium methoxide (500 µl, 25% by wt. in methanol). The solution was stirred at 80° C. for 1 h, and it was diluted with 50 ml ethylacetate. The solution was washed with water, dried and concentrated. The product was purified using small silica column and isolated as off white solid (22 mg, 54%). $^1$H NMR (CDCl$_3$): 7.89 (d, J=8.4 Hz, 1H), 7.53 (ddd, J=8.7, 5.4 and 2.4 Hz, 1H), 7.19-7.14 (m, 2H), 6.99-6.93 (m, 2H), 6.90-6.85 (m, 2H), 4.14 (s, 3H), 3.86 (s, 3H), 3.64 (s, 3H).

EXAMPLE 12

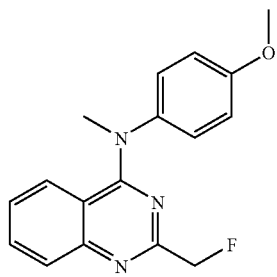

(2-Fluoromethyl-quinazolin-4-yl)-(4-methoxy-phenyl)-methyl-amine a) 2-Fluoromethyl-quinazolin-4(3H)-one: To a solution of 2-amino-benzoic acid methyl ester (151 mg, 1 mmol) and fluoro-acetonitrile (0.14 ml, 2.5 mmol) in dioxane (5 ml) at room temperature was added concentrated HCl (0.05 ml) dropwise. The mixture was heated at 80° C. for 24 h and then cooled to room temperature. The resulting solid was collected and dissolved in water (10 ml), and the solution was neutralized with saturated aqueous NaHCO₃ to pH 7. The solution was extracted by ethyl acetate. The extracts were evaporated, and the residue was purified by column chromatography on silica gel with ethyl acetate and hexane (1:1) as eluent, yielding 70 mg (39%) of the title compound.

b) (2-Fluoromethyl-quinazolin-4-yl)-(4-methoxy-phenyl)-methyl-amine: A suspension of 2-fluoromethyl-quinazolin-4(3H)-one (70 mg, 0.39 mmol) in phosphoryl chloride (2 ml) and N,N-dimethylaniline (0.035 ml, 0.27 mmol) was heated under reflux for 12 hours. The reaction mixture was poured onto ice and the precipitate was collected by filtration, then washed and dried to give 4-chloro-2-fluoromethyl-quinazoline, which was used directly for the next reaction. To a solution of 4-chloro-2-fluoromethyl-quinazoline with (4-methoxy-phenyl)-methylamine (160 mg, 1.2 mmol) in isopropyl alcohol (5 ml) was added concentrated HCl (0.05 ml) and the solution was stirred at room temperature overnight. The solution was neutralized with saturated aqueous NaHCO₃, and was extracted by ethyl acetate. The extracts were evaporated, and the residue was purified by column chromatography on silica gel with ethyl acetate and hexane (1:1) as eluent, yielding 11 mg (9.5%) of the title compound. ¹H NMR (CDCl₃): 7.87-7.84 (m, 1H), 7.60-7.54 (m, 1H), 7.14-7.10 (m, 2H), 7.04-7.01 (m, 2H), 6.95-6.91 (m, 2H), 5.60 (s, 1H), 5.44 (s, 1H), 3.85 (s, 3H), 3.60 (s, 3H).

EXAMPLE 13

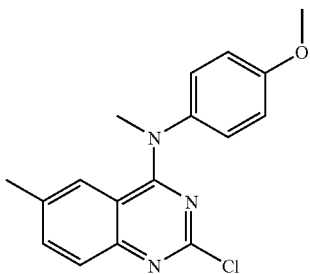

(2-Chloro-6-methyl-quinazolin-4-yl)-(4-methoxy-phenyl)-methyl-amine a) 6-Methyl-quinazoline-2,4-dione: To a suspension of 2-amino-5-methyl benzoic acid (0.758 g, 5 mmol) and potassium cyanate (0.673 g, 8.3 mmol) in water (20 mL) was added acetic acid (0.5 mL). The mixture was stirred at room temperature for 24 h. A white solid was collected by vacuum filtration, washed with water, and dried in vacuo (0.736 g, 84%): ¹H NMR (DMSO-d₆) 9.90 (br s, 1H), 8.27 (d, J=8.4 Hz, 1H), 7.70 (d, J=1.8 Hz, 1H), 7.29 (dd, J=2.4, 8.7 Hz, 1H), 6.50 (br s, 1H), 2.25 (s, 3H).

b) (2-Chloro-6-methyl-quinazolin-4-yl)-(4-methoxy-phenyl)-methyl-amine: The above 6-methyl-quinazoline-2,4-dione (201 mg, 1.14 mmol) and N,N-dimethylaniline (0.2 mL) were refluxed in phosphorus oxychloride (5 mL) under argon overnight. The solvent was removed by distillation under reduced pressure. The purple residue was dissolved in isopropanol (10 mL). N-methyl-p-anisidine (201 mg, 1.465 mmol) was added. The mixture was stirred at room temperature overnight. The solvent was evaporated and the residue was purified by column chromatography (SiO₂, EtOAc:hexanes 5-25%) to give the product as a light yellow solid (62 mg, 17%): ¹H NMR (CDCl₃) 7.62 (d, J=8.7 Hz, 1H), 7.38 (dd, J=1.8, 8.7 Hz, 1H), 7.16-7.10 (m, 2H), 6.89-6.86 (m, 2H), 6.63 (s, 1H), 3.86 (s, 3H), 3.60 (s, 3H), 2.09 (s, 3H).

Compounds of EXAMPLE 14-16 were prepared similar to Example 13.

EXAMPLE 14

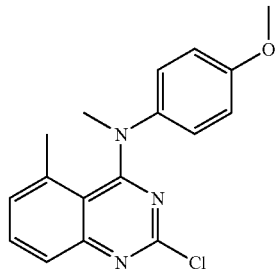

(2-Chloro-5-methyl-quinazolin-4-yl)-(4-methoxy-phenyl)-methyl-amine a) 5-Methyl-quinazoline-2,4-dione: Off-white solid: ¹H NMR (CDCl₃) 11.04 (s, 2H), 7.45 (t, J=7.8 Hz, 1H), 7.01 (d, J=7.8 Hz, 1H), 6.94 (d, J=7.5 Hz, 1H), 2.65 (s, 3H).

b) (2-Chloro-5-methyl-quinazolin-4-yl)-(4-methoxy-phenyl)-methyl-amine: Light yellow solid: ¹H NMR (CDCl₃) 7.64-7.61 (m, 1H), 7.54 (dd, J=7.2, 8.4 Hz, 1H), 6.99-6.96 (m, 1H), 6.75-6.68 (m, 4H), 3.75 (s, 3H), 3.63 (s, 3H), 2.11 (s, 3H).

EXAMPLE 15

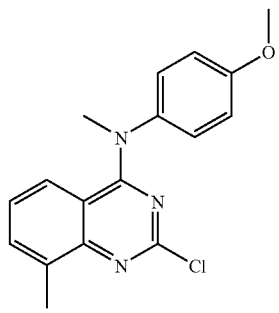

(2-Chloro-8-methyl-quinazolin-4-yl)-(4-methoxy-phenyl)-methyl-amine a) 8-Methyl-quinazoline-2,4-dione: Light brown solid: ¹H NMR (DMSO-d₆) 11.43 (s, 1H), 10.50 (s, 1H), 7.86 (d, J=8.1 Hz, 1H), 7.58 (d, J=7.2 Hz, 1H), 7.19 (t, J=7.8 Hz, 1H), 2.43 (s, 3H).

b) (2-Chloro-8-methyl-quinazolin-4-yl)-(4-methoxy-phenyl)-methyl-amine:

¹H NMR (CDCl₃) 7.42-7.39 (m, 1H), 7.14-7.04 (m, 2H), 6.94-6.87 (m, 3H), 6.84 (dd, J=1.5, 8.4 Hz, 1H), 3.84 (s, 3H), 3.60 (s, 3H), 2.63 (s, 3H).

EXAMPLE 16

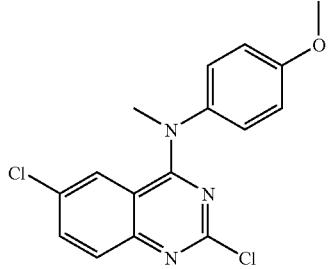

(2,6-Dichloro-quinazolin-4-yl)-(4-methoxy-phenyl)-methyl-amine a) 6-Chloro-quinazoline-2,4-dione: white solid: ¹H NMR (DMSO-d₆) 11.44 (s, 1H), 11.28 (s, 1H), 7.81 (d, J=2.1 Hz, 1H), 7.69 (dd, J=9.0, 2.1 Hz, 1H), 7.19 (d, J=9.0 Hz, 1H).

b) (2,6-Dichloro-quinazolin-4-yl)-(4-methoxy-phenyl)-methyl-amine:

Yellow solid: ¹H NMR (CDCl₃) 7.66 (d, J=8.7 Hz, 1H), 7.49 (dd, J=2.1, 8.7 Hz, 1H), 7.18-7.12 (m, 2H), 7.02-6.96 (m, 2H), 6.78 (dd, J=0.6, 2.1 Hz, 1H), 3.88 (s, 3H), 3.61 (s, 3H).

EXAMPLE 17

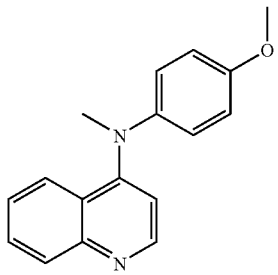

(4-Methoxy-phenyl)-methyl-(quinolin-4-yl)-amine

A mixture of 4-chloroquinoline (50 mg, 0.31 mmol) and (4-methoxy-phenyl)-methyl amine (300 mg, 2.2 mmol) was heated in a sealed tube at 140° C. overnight. The crude product was purified by chromatography (20-40% ethyl acetate/hexanes) on silica gel to give the title compound (60 mg, 0.23 mmol, 74%). ¹H NMR (CDCl₃): 8.77 (d, 1H, J=5.1), 8.00-8.04 (m, 1H), 7.61-7.64 (m, 1H), 7.55 (ddd, 1H, J=1.5, 6.9, 8.4), 7.22 (ddd, 1H, J=1.5, 6.9, 8.1), 6.99 (d, 1H, J=4.8), 6.92 (m, 2H), 6.89 (m, 2H), 3.77 (s, 3H), 3.43 (s, 3H).

EXAMPLE 18

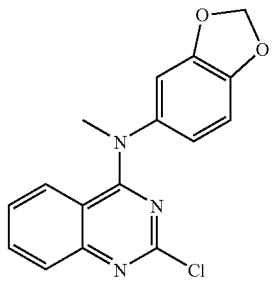

(2-Chloro-quinazolin-4-yl)-(3,4-methylenedioxyphenyl)-methyl-amine a) (2-Chloro-quinazolin-4-yl)-(3,4-methylenedioxyphenyl)-amine: The title compound was prepared from 3,4-methylenedioxyphenylamine and 2,4-dichloroquinazoline by a procedure similar to example 1b and was isolated as solids (45% yield). ¹H NMR (CDCl₃): 7.81-7.83 (m, 3H), 7.51-7.56 (m, 2H), 7.44 (d, 1H, J=2.1), 6.98 (dd, 1H, J=2.1, 8.1), 6.82 (d, 1H, J=8.1), 6.01 (s, 2H).

b). (2-Chloro-quinazolin-4-yl)-(3,4-methylenedioxyphenyl)-methyl-amine: The title compound was prepared from (2-chloro-quinazolin-4-yl)-(3,4-methylenedioxyphenyl)-amine by a procedure similar to example 36 and was isolated as solids (66% yield). ¹H NMR (CDCl₃): 7.73-7.76 (m, 1H), 7.58 (m, 1H), 7.07 (m, 2H), 6.82 (d, 1H, J=8.4), 6.72 (m, 1H), 6.68 (m, 1H), 6.06 (s, 2H), 3.59 (s, 3H).

Compounds of EXAMPLES 19 and 20 were prepared similar to Example 18.

EXAMPLE 19

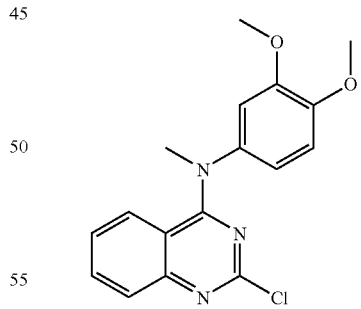

(2-Chloro-quinazolin-4-yl)-(3,4-dimethoxy-phenyl)-methyl-amine a) (2-Chloro-quinazolin-4-yl)-(3,4-dimethoxy-phenyl)-amine: ¹H NMR (CDCl₃): 7.77-7.86 (m, 3H), 7.51-7.60 (m, 3H), 7.12 (dd, 1H, J=2.4, 8.4), 6.90 (d, 1H, J=8.4), 3.94 (s, 3H), 3.91 (s, 3H).

b). (2-Chloro-quinazolin-4-yl)-(3,4-dimethoxy-phenyl)-methyl-amine: ¹H NMR (CDCl₃): 7.72-7.75 (m, 1H), 7.57

(ddd, 1H, J=1.5, 6.6, 8.4), 7.01 (ddd, 1H, J=1.2, 6.9, 8.7), 6.88-6.96 (m, 2H), 6.73-6.81 (m, 2H), 3.94 (s, 3H), 3.80 (s, 3H), 3.63 (s, 3H).

EXAMPLE 20

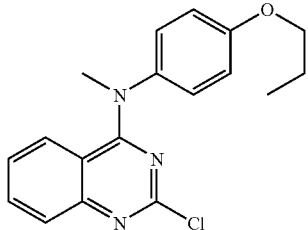

(2-Chloro-quinazolin-4-yl)-(4-propoxy-phenyl)-methyl-amine a) (2-Chloro-quinazolin-4-yl)-(4-propoxy-phenyl)-amine: $^1$H NMR (CDCl$_3$): 7.76-7.84 (m, 3H), 7.52-7.62 (m, 4H), 6.95 (m, 2H), 3.94 (t, 2H, J=6.6), 1.83 (hex, 2H, J=7.2), 1.05 (t, 3H, J=7.5)

b) (2-Chloro-quinazolin-4-yl)-(4-propoxy-phenyl)-methyl-amine: $^1$H NMR (CDCl$_3$): 7.71-7.74 (m, 1H), 7.55 (ddd, 1H, J=1.5, 6.9, 8.4), 7.10-7.16 (m, 2H), 7.00 (ddd, 1H, J=1.5, 6.9, 8.4), 6.91-6.96 (m, 3H), 3.96 (t, 2H, J=6.6), 1.84 (hex, 2H, J=7.5), 1.08 (t, 3H, J=7.5).

EXAMPLE 21

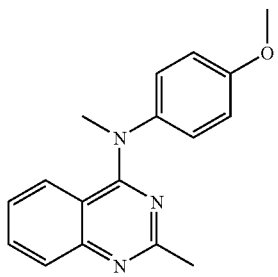

(4-Methoxy-phenyl)-methyl-(2-methyl-quinazolin-4-yl)-amine hydrochloride a) 4-Chloro-2-methyl-quinazoline: A stirred suspension of 2-methyl-4(3H)-quinazolinone (5 g, 31.2 mmol) in POCl$_3$ (100 mL) was heated at 120° C. for 3 h. The excess POCl$_3$ was removed under vacuum, then to the residue was added crushed ice and 200 mL of saturated NaHCO$_3$, and the mixture was extracted with ethyl acetate (200 mL×2). The combined extracts were washed with water, saturated NaCl, dried over anhydrous MgSO$_4$, filtered and concentrated. The crude product was purified by column chromatography (5-8% ethyl acetate/hexane) to give the title compound (2.5 g, 14.0 mmol, 45%). $^1$H NMR (CDCl$_3$): 8.21-8.25 (m, 1H), 7.89-7.99 (m, 2H), 7.66 (ddd, 1H, J=1.8, 6.6, 8.7), 2.87 (s, 3H).

b) (4-Methoxy-phenyl)-methyl-(2-methyl-quinazolin-4-yl)-amine hydrochloride: The title compound was prepared from 4-chloro-2-methyl-quinazoline (2.31 g, 12.9 mmol) and (4-methoxy phenyl)-methyl-amine (2.0 g, 14.6 mmol) by a procedure similar to example 1b and was isolated as solids (2.90 g, 9.18 mmol, 71%). $^1$H NMR (CDCl$_3$): 8.53 (dd, 1H, J=0.6, 8.1), 7.7 (ddd, 1H, J=1.2, 7.2, 8.4), 7.22 (m, 2H), 7.13 (ddd, 1H, J=1.2, 7.2, 8.7), 7.05 (m, 2H), 6.76 (d, 1H, J=8.7), 3.91 (s, 3H), 3.78 (s, 3H), 2.96 (s, 3H).

EXAMPLE 22

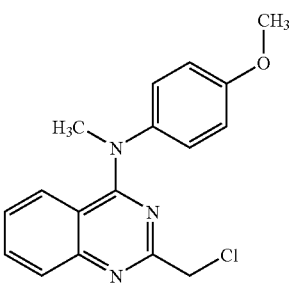

(2-Chloromethyl-quinazolin-4-yl)-(4-methoxy-phenyl)-methyl-amine a) 2-Chloromethyl-quinazolin-4(3H)-one: To a solution of 2-amino-benzoic acid methyl ester (0.26 ml, 2 mmol) and chloro-acetonitrile (0.16 ml, 4.0 mmol) in dioxane (8 ml) at room temperature was added concentrated HCl (1.0 ml) dropwise. The mixture was heated at 80° C. for 24 h and then cooled to room temperature. The resulting solid was collected and dissolved in water (10 ml), and the solution was neutralized with 2 N NaOH aqueous to pH 7. The precipitation was collected by filtration, then washed with water and dried to give 309 mg (79.6%) of the title compound.

b) (2-Chloromethyl-quinazolin-4-yl)-(4-methoxy-phenyl)-methyl-amine: A mixture of 2-chloromethyl-quinazolin-4(3H)-one (256 mg, 1.32 mmol), phosphoryl chloride (1.23 ml, 13.2 mmol) and N,N-dimethylaniline (0.34 ml, 2.64 mmol) in chloroform (10 ml) was heated under reflux for 4 h. The reaction mixture was poured onto ice and extracted by ethyl acetate. The solvent was evaporated, and the residue was purified by column chromatography on silica gel with acetate and hexane (1:1) as eluent, yielding 180 mg of 4-chloro-2-chloromethyl-quinazoline. The intermediate (170 mg, 0.80 mmol) and (4-methoxy-phenyl)-methylamine (131.7 mg, 0.96 mmol) in isopropyl alcohol (5 ml) with concentrated HCl (0.05 ml) was stirred at room temperature overnight. The precipitation was formed and collected by filtration, then washed and dried to give 231 mg (92%) of the title compound. $^1$H NMR (CDCl$_3$): 7.82 (d, J=8.7 Hz, 1H), 7.59-7.53 (m, 1H), 7.15-7.12 (m, 2H), 7.03-7.00 (m, 2H), 6.95-6.91 (m, 2H), 4.73 (s, 2H), 3.85 (s, 3H), 3.62 (s, 3H).

EXAMPLE 23

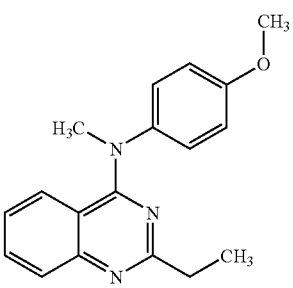

(2-Ethyl-quinazolin-4-yl)-(4-methoxy-phenyl)-methyl-amine

The title compound was prepared in three steps by a procedure similar to Example 22. $^1$H NMR (CDCl$_3$): 7.76 (d, J=8.4 Hz, 1H), 7.55-7.49 (m, 1H), 7.13-7.09 (m, 2H), 7.03-6.89 (m, 4H), 3.83 (s, 3H), 3.60 (s, 3H), 2.97 (q, J=7.5 Hz, 2H), 1.44 (t, J=7.8 Hz, 3H).

EXAMPLE 24

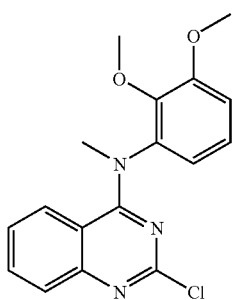

(2-Chloro-quinazolin-4-yl)-(2,3-dimethoxy-phenyl)-methyl-amine

The title compound was prepared from (2-chloro-quinazolin-4-yl)-(2,3-dimethoxy-phenyl)-amine and methyl iodide by a procedure similar to Example 7 (71% yield). $^1$H NMR (CDCl$_3$): 7.74 (d, J=8.4 Hz, 1H), 7.53-7.59 (m, 1H), 7.12 (t, J=8.4 Hz, 1H), 6.94-7.01 (m, 3H), 6.87 (dd, J=8.1 and 1.5 Hz, 1H), 3.89 (s, 3H), 3.56 (s, 3H).

EXAMPLE 25

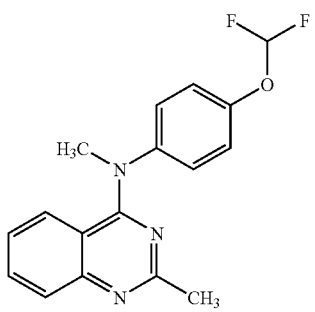

(4-Difluoromethoxy-phenyl)-(2-methyl-quinazolin-4-yl)-methyl-amine

The title compound was prepared from (4-difluoromethoxy-phenyl)-(2-methyl-quinazolin-4-yl)-amine (710 mg, 2.36 mmol) and methyl iodide (1.03 ml, 16.52 mmol), by a procedure similar to Example 7 (40.8% yield). $^1$H NMR (CDCl$_3$): 7.77 (dd, J=8.4 Hz, J=0.9 Hz, 1H), 7.59-7.53 (m, 1H), 7.17-7.10 (m, 4H), 7.06-6.99 (m, 2H), 6.78 (d, J=0.6 Hz, 0.25H), 6.54 (d, J=0.9 Hz, 0.5H), 6.29 (d, J=0.9 Hz, 0.25H), 3.62 (s, 3H), 2.75 (s, 3H).

EXAMPLE 26

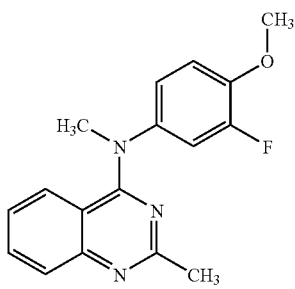

(3-Fluoro-4-methoxy-phenyl)-(2-methyl-quinazolin-4-yl)-methyl-amine

The title compound was prepared from (3-fluoro-4-methoxy-phenyl)-(2-methyl-quinazolin-4-yl)-amine (250 mg, 0.88 mmol) and methyl iodide (0.39 ml, 6.18 mmol) by a procedure similar to example 7. $^1$H NMR (CDCl$_3$): 7.76 (d, J=8.4 Hz, 1H), 7.59-7.53 (m, 1H), 7.09-6.82 (m, 5H), 3.91 (s, 3H), 3.58 (s, 3H), 2.73 (s, 3H).

EXAMPLE 27

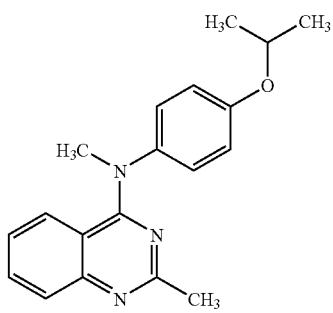

(4-Isopropoxy-phenyl)-(2-methyl-quinazolin-4-yl)-methyl-amine

The title compound was prepared from (4-isopropoxy-phenyl)-(2-methyl-quinazolin-4-yl)-amine (164.3 mg, 0.56 mmol) and methyl iodide (0.25 ml, 3.92 mmol) by a procedure similar to example 7. $^1$H NMR (CDCl$_3$): 7.73 (d, J=7.8 Hz, 1H), 7.54-7.49 (m, 1H), 7.10-6.86 (m, 6H), 4.57-4.52 (m, 1H), 3.58 (s, 3H), 2.72 (s, 3H), 1.36 (d, J=6 Hz, 6H).

EXAMPLE 28

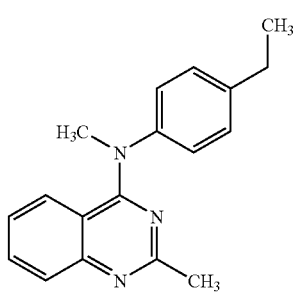

(4-Ethyl-phenyl)-(2-methyl-quinazolin-4-yl)-methyl-amine

The title compound was prepared from (4-ethyl-phenyl)-(2-methyl-quinazolin-4-yl)-amine (122 mg, 0.46 mmol) and methyl iodide (0.2 ml, 3.25 mmol) by a procedure similar to example 7. $^1$H NMR (CDCl$_3$): 7.74 (d, J=8.1 Hz, 1H), 7.54-7.49 (m, 1H), 7.19 (d, J=8.4 Hz, 2H), 7.09-6.92 (m, 4H), 3.61 (s, 3H), 2.73-2.63 (m, 5H), 1.26 (d, J=7.5 Hz, 3H).

Compounds of Example 29 and 30 were prepared by a procedure similar to Example 13.

EXAMPLE 29

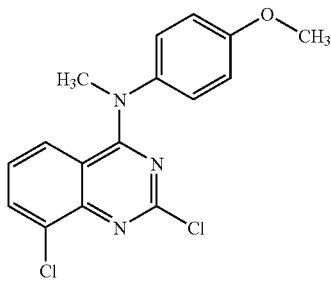

(2,8-Dichloro-quinazolin-4-yl)-(4-methoxy-phenyl)-methyl-amine a) 8-Chloro-1H-quinazoline-2,4-dione: White solid: $^1$H NMR (DMSO-$d_6$) 11.47 (s, 1H), 10.77 (s, 1H), 7.88 (m, 1H), 7.78 (m, 1H), 7.18 (m, 1H).

b) (2,8-Dichloro-quinazolin-4-yl)-(4-methoxy-phenyl)-methyl-amine: Off-white solid: $^1$H NMR (CDCl$_3$) 7.66 (dd, J=2.7, 6.3 Hz, 1H), 7.14-7.10 (m, 2H), 6.97-6.89 (m, 4H), 3.86 (s, 3H), 3.62 (s, 3H).

EXAMPLE 30

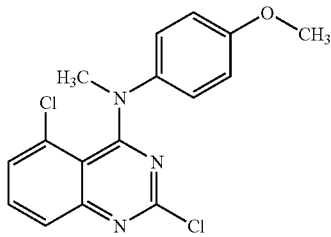

(2,5-Dichloro-quinazolin-4-yl)-(4-methoxy-phenyl)-methyl-amine a) 5-Chloro-1H,3H-quinazoline-2,4-dione: White solid: $^1$H NMR (DMSO-$d_6$) 11.28 (s, 2H), 7.55 (m, 1H), 7.19 (d, J=7.8 Hz, 1H), 7.12 (d, J=8.4 Hz, 1H).

b) (2,5-Dichloro-quinazolin-4-yl)-(4-methoxy-phenyl)-methyl-amine: Yellow solid: $^1$H NMR (CDCl$_3$) 7.67 (m, 1H), 7.52 (m, 1H), 7.16 (m, 1H), 6.80-6.69 (m, 4H), 3.76 (s, 3H), 3.65 (s, 3H).

EXAMPLE 31

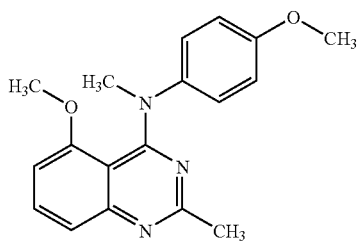

(5-Methoxy-2-methyl-quinazolin-4-yl)-(4-methoxy-phenyl)-methyl-amine a) 5-Methoxy-2-methyl-quinazolin-4-ol: To a suspension of 2-amino-6-methoxy-benzoic acid (305 mg, 1.82 mmol) and 4-N,N-dimethylaminopyridine (20 mg, 0.16 mmol) in DMF/toluene (2:6 mL) at 0° C. was added triethylamine (1.1 mL, 7.9 mmol) followed by slow addition of acetyl chloride (0.40 mL, 5.6 mmol) under argon. The suspension was stirred at rt for 19 h. Ammonium acetate (0.62 g, 8.0 mmol) was added and the reaction mixture was further stirred at 90° C. for 5 h. The solid was collected by filtration, washed with water, and dried to give an off-white solid (103 mg, 30%): $^1$H NMR (CDCl$_3$) 10.69 (s, 1H), 7.66 (t, J=8.4 Hz, 1H), 7.25 (d, J=8.4 Hz, 1H), 6.49 (d, J=8.4 Hz, 1H), 4.01 (s, 3H), 2.53 (s, 3H).

b) (5-Methoxy-2-methyl-quinazolin-4-yl)-(4-methoxy-phenyl)-methyl-amine: The title compound was prepared by a procedure similar to that of Example 13b as white solid: $^1$H NMR (CDCl$_3$) 7.51 (t, J=8.4 Hz, 1H), 7.35 (dd, J=0.9, 8.4 Hz, 1H), 6.85-6.80 (m, 2H), 6.85-6.72 (m, 2H), 6.56 (dd, J=0.9, 7.8 Hz, 1H), 3.75 (s, 3H), 3.60 (s, 3H), 3.25 (s, 3H), 2.68 (s, 3H).

EXAMPLE 32

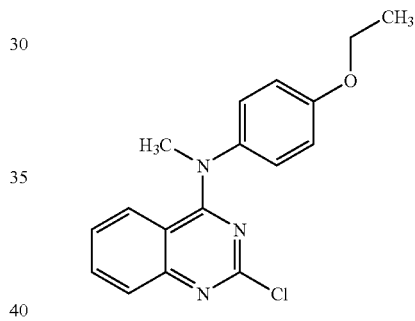

(2-Chloro-quinazolin-4-yl)-(4-ethoxy-phenyl)-methylamine

The title compound was prepared from (2-chloro-quinazolin-4-yl)-(4-ethoxy-phenyl)-amine by a procedure similar to example 7 (28%). $^1$H NMR (CDCl$_3$): 7.73 (m, 1H), 7.55 (m, 1H), 7.12 (m, 2H), 7.00 (m, 1H), 6.93 (m, 3H), 4.07 (q, J=7.2, 2H), 3.61 (s, 3H), 1.46 (t, J=7.2, 3H).

EXAMPLE 33

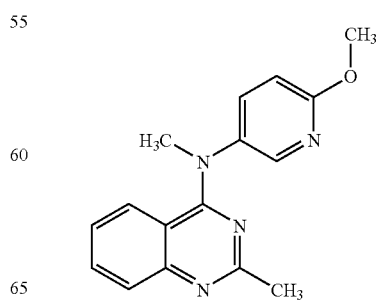

(2-Methyl-quinazolin-4-yl)-(6-methoxy-pyridin-3-yl)-methyl-amine

The title compound was prepared from (2-methyl-quinazolin-4-yl)-(6-methoxy-pyridin-3-yl)-amine by a procedure similar to example 7 (28%). $^1$H NMR (CDCl$_3$): 8.03 (d, J=2.7, 1H), 7.77 (m, 1H), 7.56 (ddd, J=8.1, 6.3, 1.8, 1H), 7.38 (dd, J=8.7, 3.0, 1H), 7.01 (m, 2H), 6.76 (d, J=9.0, 1H), 3.96 (s, 3H), 3.59 (s, 3H), 2.73 (s, 3H).

EXAMPLE 34

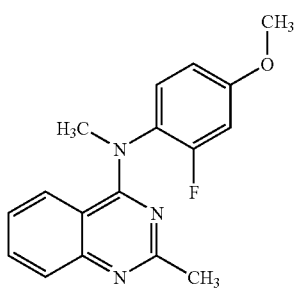

(2-Fluoro-4-methoxy-phenyl)-(2-methyl-quinazolin-4-yl)-methyl-amine

The title compound was prepared from (2-methyl-quinazolin-4-yl)-(2-fluoro-4-methoxy-phenyl)-amine by a procedure similar to example 7 (51%). $^1$H NMR (CDCl$_3$): 7.76 (d, J=8.1, 1H), 7.55 (ddd, J=8.1, 6.3, 1.8, 1H), 6.98-7.11 (m, 3H), 6.66-6.76 (m, 2H), 3.83 (s, 3H), 3.54 (s, 3H), 2.73 (s, 3H).

EXAMPLE 35

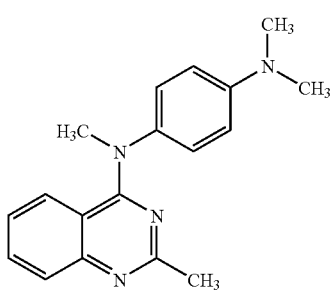

(4-Dimethylamino-phenyl)-(2-methyl-quinazolin-4-yl)-methyl-amine

To a solution of (2-methyl-quinazolin-4-yl)-(4-aminophenyl)-methylamine (14 mg, mmol) in 1.5 mL of 37% aqoues formaldehyde solution and 10 uL of glacial acetic was added Sodium cyanoborohydride (15 mg, 0.24 mmol) and the mixture was stirred at room temperature for 2 h. The reaction mixture was quenched by adding 50 uL of 1N HCl. It was diluted with 50 mL of ethyl acetate, washed with saturated sodium bicarbonate, and followed by saturated sodium chloride. The organic layer was dried over anhydrous Na$_2$SO$_4$, filtered and concentrated. The residue was purified by column chromatography (25% ethyl acetate/hexanes) on silica gel to give the title compound (12.4 mg, 0.042 mmol, 80%). $^1$H NMR (CDCl$_3$): 7.71 (m, 1H), 7.50 (ddd, J=8.4, 6.9, 1.5, 1H), 7.03-7.09 (m, 3H), 6.95 (ddd, J=8.1, 6.6, 0.9, 1H), 6.70 (m, 2H), 3.57 (s, 3H), 2.99 (s, 6H), 2.71 (s, 3H).

EXAMPLE 36

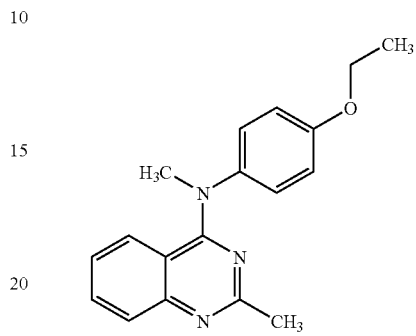

(4-Ethoxy-phenyl)-(2-methyl-quinazolin-4-yl)-methyl-amine

The title compound was prepared from (2-methyl-quinazolin-4-yl)-(4-ethoxy-phenyl)-amine by a procedure similar to example 7 (67%). $^1$H NMR (CDCl$_3$): 7.71-7.74 (m, 1H), 7.51 (ddd, J=8.1, 6.6, 1.5, 1H), 7.09 (m, 2H), 6.95-7.04 (m, 2H), 6.86-6.92 (m, 2H), 4.04 (q, J=6.9, 2H), 3.58 (s, 3H), 2.72 (s, 3H), 1.44 (t, J=6.9, 3H).

EXAMPLE 37

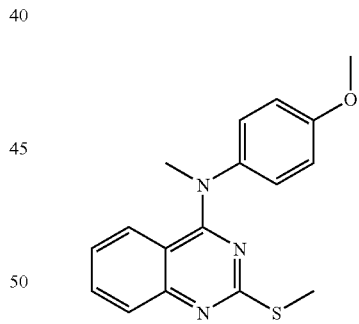

(2-Methylthio-quinazolin-4-yl)-(4-methoxy-phenyl)-methyl-amine

A mixture of (2-chloro-quinazolin-4-yl)-(4-methoxy-phenyl)-methyl-amine (150 mg, 0.5 mmol), sodium methanethiolate (105 mg, 1.5 mmol) in 5 mL of solvent (THF:MeOH:water=3:1:1) was stirred at 70° C. for 4 h. The reaction mixture was diluted with 30 mL of ethyl acetate and it was washed with brine, dried over anhydrous Na$_2$SO$_4$, filtered and concentrated. The crude product was purified by chromatography on silica gel with acetate and hexane (1:5) as eluent, yielding 11 mg of title compound (7%). $^1$H NMR (CDCl$_3$):

7.65 (d, J=8.4 Hz, 1H), 7.51-7.45 (m, 1H), 7.14-7.10 (m, 2H), 6.93-6.89 (m, 4H), 3.84 (s, 3H), 3.58 (s, 3H), 2.67 (s, 3H).

EXAMPLE 38

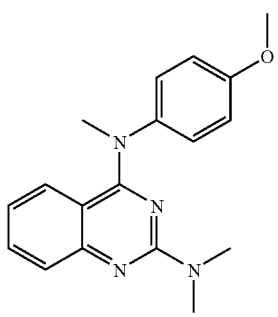

(2-Dimethylamino-quinazolin-4-yl)-(4-methoxy-phenyl)-methyl-amine

A mixture of (2-chloro-quinazolin-4-yl)-(4-methoxy-phenyl)-methyl-amine (150 mg, 0.5 mmol), 2.0 M dimethylamine in methanol (2.0 ml, 4 mmol) in a sealed tube was stirred at 70-80° C. overnight. The mixture was filled and the filtration was concentrated by vacuum. The residue was extracted with ethyl acetate and was washed with brine, dried over anhydrous $Na_2SO_4$, filtered and concentrated. The crude product was purified by chromatography on silica gel with acetate and hexane (1:9) as eluent, yielding 128 mg of title compound (83%). $^1$H NMR (CDCl$_3$): 7.44 (d, J=7.8 Hz, 1H), 7.36-7.30 (m, 1H), 7.11-7.08 (m, 2H), 6.90-6.85 (m, 3H), 6.65-6.59 (m, 1H), 3.82 (s, 3H), 3.51 (s, 3H), 3.30 (s, 6H).

EXAMPLE 39

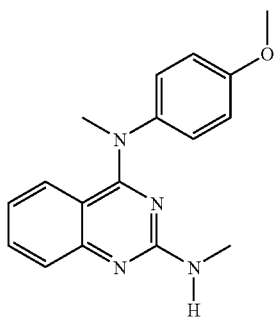

(2-Methylamino-quinazolin-4-yl)-(4-methoxy-phenyl)-methyl-amine

The title compound was prepared from (2-chloro-quinazolin-4-yl)-(4-methoxy-phenyl)-methyl-amine (150 mg, 0.5 mmol), 2.0 M methylamine in THF (2.0 ml, 4 mmol) by a procedure similar to that of example 38 (53.7%). $^1$H NMR (CDCl$_3$): 7.45 (d, J=7.8 Hz, 1H), 7.39-7.33 (m, 1H), 7.11-7.07 (m, 2H), 6.90-6.87 (m, 3H), 6.69-6.64 (m, 1H), 4.95 (brs, 1H), 3.82 (s, 3H), 3.50 (s, 3H), 3.11 (d, J=5.1 Hz, 3H).

EXAMPLE 40

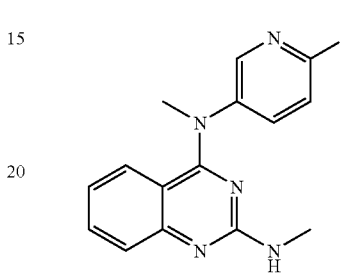

(2-Methylamino-quinazolin-4-yl)-(6-methoxy-pyridin-3-yl)-methyl-amine

The title compound was prepared from (2-chloro-quinazolin-4-yl)-(6-methoxy-pyridin-3-yl)-methyl-amine (69 mg, 0.23 mmol) and 2.0 M methylamine in THF (4 ml, 8 mmol) by a procedure similar to example 38 to give 20 mg (30%) of yellow solids. $^1$H NMR (CDCl$_3$): 8.02-8.01 (m, 1H), 7.48 (d, J=8.1 Hz, 1H), 7.42-7.34 (m, 2H), 6.97-6.94 (m, 1H), 6.76-6.70 (m, 2H), 5.01 (brs, 1H), 3.95 (s, 3H), 3.50 (s, 3H), 3.12 (d, J=5.1 Hz, 3H).

EXAMPLE 41

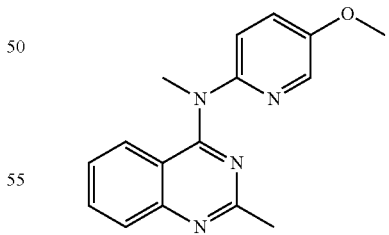

(5-Methoxy-pyridin-2-yl)-(2-methyl-quinazolin-4-yl)-methyl-amine

The title compound was prepared from (5-methoxy-pyridin-2-yl)-(2-methyl-quinazolin-4-yl)-amine by a procedure similar to example 7. $^1$H NMR (CDCl$_3$): 8.31 (d, 3.3, 1H), 7.80 (d, J=8.4, 1H), 7.58 (ddd, J=1.5, 6.6, 8.4, 1H), 7.13 (dd, J=3.3, 9.0, 1H), 6.99-7.10 (m, 2H), 6.82 (d, J=9.0, 1H), 3.87 (s, 3H), 3.70 (s, 3H), 2.76 (s, 3H).

EXAMPLE 42

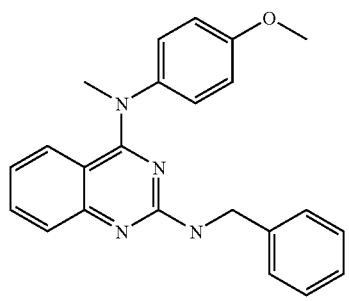

(2-Benzylamino-quinazolin-4-yl)-(4-methoxyphenyl)-methylamine

A solution of (2-chloro-quinazolin-4-yl)-(4-methoxyphenyl)-methylamine (150 mg, 0.5 mmol), benzyl amine (110 uL, 1.0 mmol) and triethyl amine (100 uL) in 5 mL of THF in a seal tube was heated overnight at 80° C. After cooling to room temperature the reaction mixture was diluted with 25 mL of ethyl acetate, washed with saturated NaHCO$_3$, dried over anhydrous Na$_2$SO$_4$, filtered and concentrated. The crude was purified by column chromatography (35% ethyl acetate/hexane) to give the title compound (25 mg, 0.067 mmol, 13%). $^1$H NMR (CDCl$_3$): 7.24-7.46 (m, 7H), 7.10 (m, 2H), 6.84-6.92 (m, 3H), 6.68 (ddd, J=8.1. 6.9, 1.5, 1H), 4.78 (d, J=6.5, 2H), 3.83 (s, 3H), 3.46 (s, 3H).

EXAMPLE 43

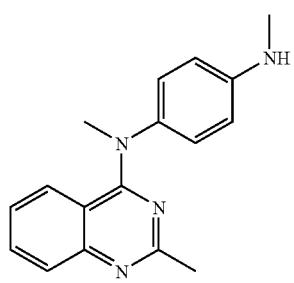

(2-Methyl-quinazolin-4-yl)-(4-methylamino-phenyl)-methylamine

A mixture of (2-methyl-quinazolin-4-yl)-(N-methyl-4-acetamido-phenyl)-methylamine (103 mg, 0.321 mmol) in 3 mL of methanol and 3 mL of 2N NaOH was heated at 90° C. for 4 h. The reaction mixture was cooled to room temperature and diluted 25 mL of ethyl acetate. It was washed with saturated NaHCO$_3$, and the organic layer was dried over anhydrous Na$_2$SO$_4$, filtered and concentrated. The crude was purified by column chromatography (40% ethyl acetate/hexane) to give the title compound (28 mg, 0.10 mmol, 31%). $^1$H NMR (CDCl$_3$): 7.71 (m, 1H), 7.50 (ddd, J=8.4, 6.9, 1.5, 1H), 6.93-7.11 (m, 4H), 6.60 (m, 2H), 3.84 (s, broad, 1H), 3.57 (s, 3H), 2.87 (s, 3H), 2.70 (s, 3H).

EXAMPLE 44

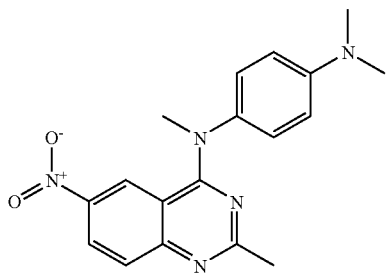

(2-Methyl-6-nitroquinazolin-4-yl)-(4-dimethylaminophenyl)-methylamine

A mixture of 4-chloro-2-methyl-6-nitro-quinazolinone (160 mg, 0.72 mmol), N$^1$,N$^1$,N$^4$-trimethylbenzene-1,4-diamine (0.84 mmol) and sodium acetate (70 mg, 0.90 mmol) in 5 mL of solvent (THF:water/1:1) was stirred at room temperature for 45 min. The reaction mixture was diluted with 50 mL of ethyl acetate and washed with saturated NaHCO$_3$. The organic layer was dried over anhydrous MgSO$_4$, filtered and concentrated. The crude product was purified by chromatography (40% ethyl acetate/hexanes) on silica gel to give the title compound (231 mg, 0.68 mmol, 96%). $^1$H NMR (CDCl$_3$): 8.24 (dd, J=9.6, 3.0, 1H), 7.82 (d, J=2.4, 1H), 7.72 (d, J=9.0, 1H), 7.08 (m, 2H), 6.78 (m, 2H), 3.64 (s, 3H), 3.01 (s, 6H), 2.71 (s, 3H).

EXAMPLE 45

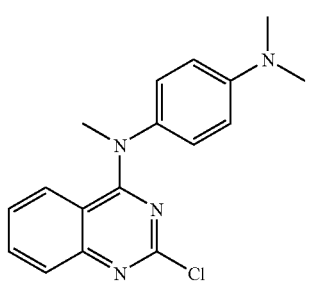

(2-Chloro-quinazolin-4-yl)-(4-dimethylaminophenyl)-methylamine

The title compound was prepared from 2,4-dichloro-6-nitro-quinazoline and N$^1$,N$^1$,N$^4$-trimethylbenzene-1,4-diamine by a procedure similar to example 44. $^1$H NMR (CDCl₃): 7.71 (m, 1H), 7.51-7.56 (m, 1H), 7.07 (m, 2H), 6.99 (m, 2H), 6.71 (m, 2H), 3.59 (s, 3H), 3.01 (s, 6H).

EXAMPLE 46

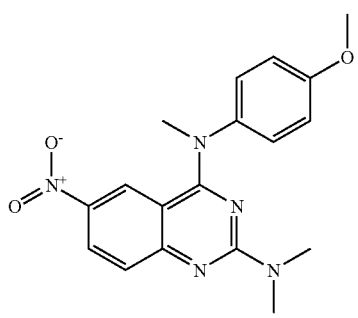

(2-Dimethylamino-6-nitroquinazolin-4-yl)-(4-methoxyphenyl)-methylamine

A solution of (2-chloro-6-nitroquinazolin-4-yl)-(4-methoxyphenyl)-methylamine (48 mg, 0.14 mmol) in 2 mL of dimethylamine in methanol (2M, 25 mmol) was heated overnight in a seal tube at 70° C. for 48 h. The reaction mixture was cooled to room temperature and concentrated under vacuum. The residue was purified by chromatography (15% ethyl acetate/hexane) to give the title compound (39 mg, 79%). ¹H NMR (CDCl₃): 8.08 (dd, J=9.3, 2.4, 1H), 7.71 (d, J=2.4, 1H), 7.35 (d, J=9.3, 1H), 7.14 (m, 2H), 6.97 (2H), 3.85 (s, 3H), 3.55 (s, 3H), 3.33 (s, 6H).

EXAMPLE 47

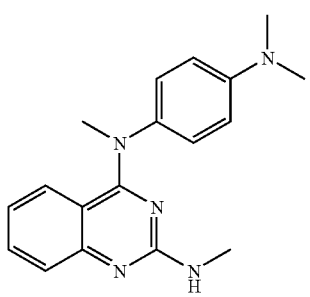

(2-Methylamino-quinazolin-4-yl)-(4-dimethylaminophenyl)-methylamine

The title compound was prepared from (2-chloro-quinazolin-4-yl)-(4-dimethylaminophenyl)-methylamine and methyl amine by a procedure similar to example 46. ¹H NMR (CDCl₃): 7.42-7.42 (m, 1H), 7.34 (ddd, J=8.1, 6.9, 4.0, 1H), 7.04 (m, 2H), 6.94 (m, 1H), 6.63-6.71 (m, 3H), 5.13 (s, broad, 1H), 3.49 (s, 3H), 3.10 (d, J=4.8, 3H), 2.97 (s, 6H).

EXAMPLE 48

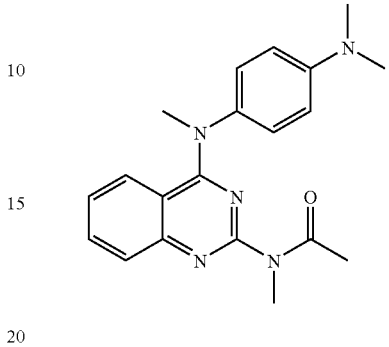

[2-(N-Methyl-acetamido)-quinazolin-4-yl]-(4-dimethylaminophenyl)-methylamine

To a solution of (2-methylamino-quinazolin-4-yl)-(4-dimethylaminophenyl)-methylamine (40 mg, 0.13 mmol) in 4 mL of methylenechloride cooled at 0° C. was added triethylamine (50 uL, 0.36 mmol), few crystals of dimethylaminopyridine and acetic anhydride (50 uL, 0.53 mmol). The reaction mixture was stirred for 1 h at 0° C., warmed to room temperature, and stirred overnight. The reaction mixture was diluted with 25 mL of ethyl acetate and washed with 25 mL of saturated sodium bicarbonate. The organic layer was dried over anhydrous NaSO₄, filtered and concentrated. The residue was purified by chromatography (40% ethyl acetate/hexane) to give the title compound (39 mg, 0.11 mmol, 85%). ¹H NMR (CDCl₃): 7.65-7.69 (m, 1H), 7.52 (ddd, J=8.4, 6.6, 1.8, 1H), 6.93-7.12 (m, 4H), 6.72 (m, 2H), 3.56 (s, 3H), 3.01 (s, 6H), 2.52 (s, 3H).

EXAMPLE 49

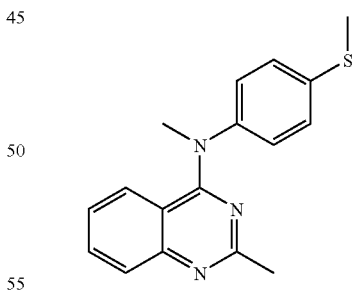

(4-Methylthio-phenyl)-(2-methyl-quinazolin-4-yl)-methylamine

To a solution of (4-methylthio-phenyl)-(2-methyl-quinazolin-4-yl)-amine (263 mg, 0.94 mmol) in DMF (4 ml) at 0° C. was added sodium hydride (56.4 mg, 1.40 mmol, 60% oil dispersion) and followed by methyl iodide (0.09 ml, 1.40 mmol). The mixture was stirred at 0° C. for 1 h, then allowed to warm to room temperature and stirred for another 2 h. The reaction mixture was diluted with EtOAc (15 ml), washed with saturated NaHCO$_3$ aq., brine, dried over Na$_2$SO$_4$, filtered and concentrated by vacuum. The residue was purified by chromatography on silica gel with acetate and hexane (1:2 to 1:1) as eluent, yielding 120 mg of title compound (40.7%). $^1$H NMR (CDCl$_3$): 7.76 (d, J=9.0 Hz, 1H), 7.54 (t, J=7.5 Hz, 1H), 7.24-7.19 (m, 2H), 7.10-6.97 (m, 4H), 3.59 (s, 3H), 2.74 (s, 3H), 2.48 (s, 3H)

EXAMPLE 50

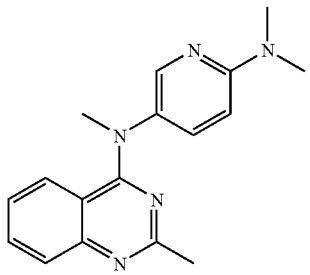

(2-Dimethylamino-pyridine-5-yl)-(2-methyl-quinazolin-4-yl)-methylamine

The title compound was prepared from (2-dimethylamino-pyridine-5-yl)-(2-methyl-quinazolin-4-yl)-amine (45 mg, 0.16 mmol), methyl iodide (0.016 ml, 0.24 mmol), sodium hydride (9.6 mg, 0.24 mmol, 60% oil dispersion) in DMF similar to example 49 to give 22 mg (47%) of paint yellow solids. $^1$H NMR (CDCl$_3$): 8.07 (d, J=2.4 Hz, 1H), 7.63 (dd, J=0.9 Hz, J=8.4 Hz, 1H), 7.56-7.51 (m, 1H), 7.27-7.18 (m, 2H), 7.05-7.00 (m, 1H), 6.50 (d, J=9.3 Hz, 1H), 3.55 (s, 3H), 3.12 (s, 6H), 2.72 (s, 3H).

EXAMPLE 51

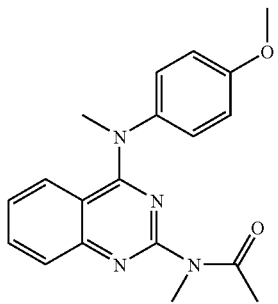

(4-Methoxy-phenyl)-(2-N-methylacetamido-quinazolin-4-yl)-methylamine

To a solution of (4-methoxy-phenyl)-(2-methylamine-quinazolin-4-yl)-methylamine (100 mg, 0.34 mmol) in 5 ml of dichloromethane was added triethylamine (0.071 ml, 0.51 mmol), acetyl chloride (0.036 ml, 0.51 mmol) followed by 2 mg of DMAP at 0° C. The reaction mixture was allowed to warm to room temperature and stirred for 2 h. The solvent was removed by vacuum. The residue was dissolved in EtOAc (20 ml), washed with water, brine, dried over Na$_2$SO$_4$, filtered and concentrated by vacuum. The crude product was purified by chromatography on silica gel with acetate, hexane and methanol (1:3 to 1:1:0.05) as eluent, yielding 36 mg of title compound (31.5%) as white solids. $^1$H NMR (CDCl$_3$): 7.70-7.67 (m, 1H), 7.56-7.52 (m, 1H), 7.17-7.14 (m, 2H), 6.97-6.93 (m, 4H), 3.86 (s, 3H), 3.57 (s, 6H), 2.52 (s, 3H).

EXAMPLE 52

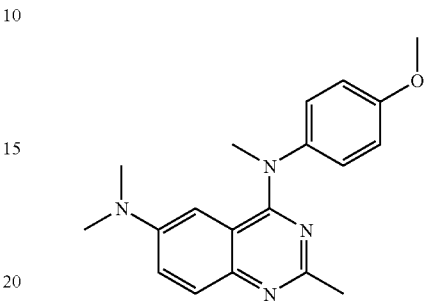

(6-Dimethylamino-2-methyl-quinazolin-4-yl)-(4-methoxy-phenyl)-methylamine

To a mixture of (6-amino-2-methyl-quinazolin-4-yl)-(4-methoxy-phenyl)-methylamine (16 mg, 0.05 mmol), 2 ml of 37% formaldehyde water solution and sodium cyanoborohydride (6.3 mg, 0.1 mmol) was added 2 N HCl (0.05 ml) at 0° C. The reaction mixture was stirred for 1 h at 0° C., then diluted by EtOAc (10 ml), washed with saturated NaHCO$_3$ aq., brine, dried over Na$_2$SO$_4$, filtered and concentrated by vacuum. The crude product was purified by chromatography on silica gel with acetate, hexane (1:3 to 1:1) as eluent, yielding 11 mg of title compound (68.8%) as yellow solids. $^1$H NMR (CDCl$_3$): 7.63 (d, J=9.0 Hz, 1H), 7.20-7.12 (m, 3H), 6.91-6.88 (m, 2H), 6.23 (d, J=2.7 Hz, 1H), 3.80 (s, 3H), 3.57 (s, 3H), 2.69 (s, 3H), 2.62 (s, 6H).

EXAMPLE 53

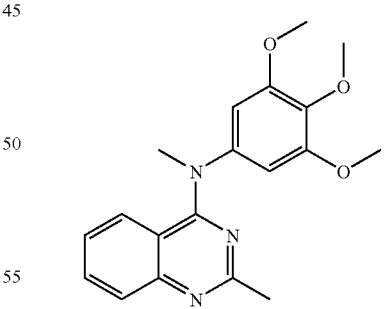

(3,4,5-trimethoxy-phenyl)-(2-methyl-quinazolin-4-yl)-methylamine

The title compound was prepared from (3,4,5-trimethoxy-phenyl)-(2-methyl-quinazolin-4-yl)-amine (232 mg, 0.71 mmol), methyl iodide (0.07 ml, 1.08 mmol), sodium hydride (43 mg, 1.08 mmol, 60% oil dispersion) in DMF similar to example 49 to give 65 mg (27%) of white solids. $^1$H NMR (CDCl₃): 7.75 (d, J=8.4 Hz, 1H), 7.58-7.53 (m, 1H), 7.11-7.00 (m, 2H), 6.39 (s, 2H), 3.88 (s, 3H), 3.73 (s, 6H), 3.62 (s, 3H), 2.74 (s, 3H).

EXAMPLE 54

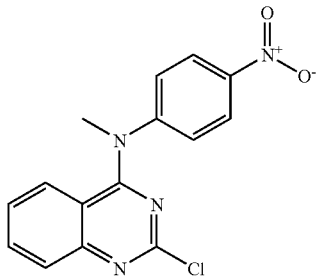

(2-Chloro-quinazolin-4-yl)-(4-nitro-phenyl)-methyl-amine

The title compound was prepared from 2,4-dichloro-quinazoline (50 mg, 0.251 mmol) and 4-nitro-N-methylaniline (46 mg, 0.302 mmol) by a procedure similar to example 1b and was isolated as yellow powder (6 mg, 12%). ¹H NMR (CDCl₃): 8.24 (d, J=8.7 Hz, 2H), 7.81 (dd, J=8.1, and 2.4 Hz, 1H), 7.68 (ddd, J=8.1, 7.5 and 2.4 Hz, 1H), 7.28 (d, J=8.7 Hz, 2H), 7.18 (ddd, J=8.1, 7.5 and 2.4 Hz, 1H), 7.07 (d, J=7.8 Hz, 1H), 3.75 (s, 3H).

EXAMPLE 55

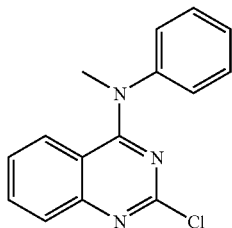

(2-Chloro-quinazolin-4-yl)-phenyl-methyl-amine

The title compound was prepared from 2,4-dichloro-quinazoline (50 mg, 0.251 mmol) and N-methylaniline (20 µL, 0.301 mmol) by a procedure similar to example 1b and was isolated as white powder (40 mg, 80%). ¹H NMR (CDCl₃): 7.76 (dd, J=8.7, and 1.5 Hz, 1H), 7.56 (ddd, J=8.1, 6.6 and 1.5 Hz, 1H), 7.46-7.35 (m, 3H), 7.24-7.20 (m, 2H), 6.98 (ddd, J=8.7, 6.6 and 1.5 Hz, 1H), 6.90 (dd, J=8.7 and 1.5 Hz, 1H), 3.65 (s, 3H).

EXAMPLE 56

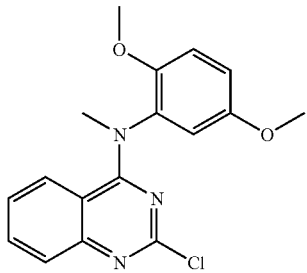

(2-Chloro-quinazolin-4-yl)-(2,5-dimethoxy-phenyl)-methyl-amine

The title compound was prepared from (2-chloro-quinazolin-4-yl)-(2,5-dimethoxy-phenyl)-amine and methyl iodide by a procedure similar to example 7 (78% yield). ¹H NMR (CDCl₃): 7.72-7.75 (m, 1H), 7.56 (ddd, J=8.4, 5.7 and 2.1 Hz, 1H), 6.98-7.00 (m, 2H), 6.92-6.92 (m, 2H), 6.78-6.79 (m, 1H), 3.75 (s, 3H), 3.58 (s, 3H), 3.56 (s, 3H).

EXAMPLE 57

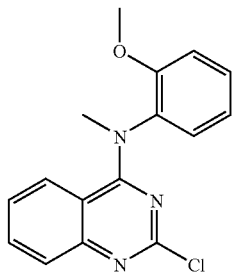

(2-Chloro-quinazolin-4-yl)-(2-methoxy-phenyl)-methyl-amine

The title compound was prepared from (2-chloro-quinazolin-4-yl)-(2-methoxy-phenyl)-amine and methyl iodide by a procedure similar to example 7 (72% yield). ¹H NMR (CDCl₃): 7.72 (d, J=8.1 Hz, 1H), 7.54 (ddd, J=8.4, 6.6 and 1.5 Hz, 1H), 7.20 (dd, J=8.4 and 1.8 Hz, 1H), 6.87-7.04 (m, 4H), 3.67 (s, 3H), 3.56 (s, 3H).

EXAMPLE 58

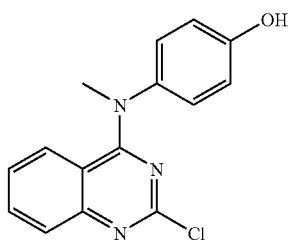

(2-Chloro-quinazolin-4-yl)-(4-hydroxyphenyl)-methylamine

To a solution of (2-chloro-quinazolin-4-yl)-(4-methoxy-phenyl)-methyl-amine (100 mg, 0.334 mmol) in 30 ml dichloromethane cooled at −20° C. was added slowly 60 µl of BBr₃ (0.668 mmol). The reaction mixture was stirred at −20° C. for 2 h then it was warmed to room temperature. It was stirred another 2 h at this temperature. The reaction mixture was diluted with ethyl acetate (50 ml) and washed with cold 5% sodium bicarbonate. The organic phase was dried and concentrated. The residue was purified by a small silica column using ethyl acetate and hexane (1:3) as eluents to give the product (57 mg, 57%). ¹H NMR (CDCl₃): 7.65-7.56 (m, 2H), 7.04-6.87 (m, 5H), 3.59 (s, 3H).

The compounds of Examples 59 and 60 were prepared similar to Example 13.

EXAMPLE 59

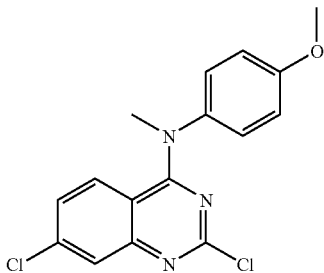

(2,7-Dichloro-quinazolin-4-yl)-(4-methoxy-phenyl)-methyl-amine a) 7-Chloro-quinazoline-2,4-dione: White solid: $^1$H NMR (DMSO-$d_6$) 11.42 (s, 1H), 11.26 (s, 1H), 7.88 (d, J=8.7 Hz, 1H), 7.22 (dd, J=1.2, 8.1 Hz, 1H), 7.18 (d, J=2.1 Hz, 1H).
b) (2,7-Dichloro-quinazolin-4-yl)-(4-methoxy-phenyl)-methyl-amine: Light yellow solid: $^1$H NMR (CDCl$_3$) 7.70 (d, J=2.4 Hz, 1H), 7.16-7.11 (m, 2H), 6.98-6.92 (m, 3H), 6.80 (d, J=9.3 Hz, 1H), 3.86 (s, 3H), 3.60 (s, 3H).

EXAMPLE 60

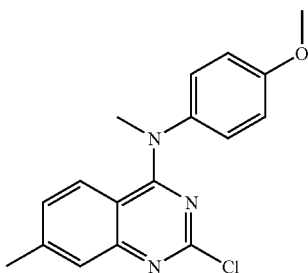

(2-Chloro-7-methyl-quinazolin-4-yl)-(4-methoxy-phenyl)-methyl-amine a) 7-Methyl-quinazoline-2,4-dione: White solid: $^1$H NMR (DMSO-$d_6$) 10.07 (br s, 1H), 8.24 (s, 1H), 7.79 (d, J=8.1 Hz, 1H), 6.78 (dd, J=0.6, 9.0 Hz, 1H), 6.54 (br s, 1H), 2.30 (s, 3H).
b) (2-Chloro-7-methyl-quinazolin-4-yl)-(4-methoxy-phenyl)-methyl-amine: Light yellow solid: $^1$H NMR (CDCl$_3$) 7.51 (m, 1H), 7.16-7.10 (m, 2H), 6.96-6.91 (m, 2H), 6.83 (dd, J=1.8, 8.7 Hz, 1H), 6.78 (d, J=8.7 Hz, 1H), 3.85 (s, 3H), 3.59 (s, 3H), 2.38 (s, 3H).

EXAMPLE 61

Identification of (2-Chloro-quinazolin-4-yl)-(4-methoxy-phenyl)-methyl-amine and Analogs as Caspase Cascade Activators and Inducers of Apoptosis in Solid Tumor Cells Human breast cancer cell lines T-47D and DLD-1 were grown according to media component mixtures designated by American Type Culture Collection+10% FCS (Invitrogen Corporation), in a 5% $CO_2$–95% humidity incubator at 37° C. T-47D and DLD-1 cells were maintained at a cell density between 50 and 80% confluency at a cell density of 0.1 to 0.6×10$^6$ cells/mL. Cells were harvested at 600×g and resuspended at 0.65×10$^6$ cells/mL into appropriate media+10% FCS. An aliquot of 22.5 µL of cells was added to a well of a 384-well microtiter plate containing 2.5 µL of a 10% DMSO in RPMI-1640 media solution containing 0.16 to 100 µM of (2-chloro-quinazolin-4-yl)-(4-methoxy-phenyl)-methyl-amine or other test compound (0.016 to 10 µM final). An aliquot of 22.5 µL of cells was added to a well of a 384-well microtiter plate containing 2.5 µL of a 10% DMSO in RPMI-1640 media solution without test compound as the control sample. The samples were mixed by agitation and then incubated at 37° C. for 48 h in a 5% $CO_2$–95% humidity incubator. After incubation, the samples were removed from the incubator and 25 µL of a solution containing 14 µM of N-(Ac-DEVD)-N'-ethoxycarbonyl-R110 fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 µg/mL lysolecithin (Calbiochem) was added. The samples were mixed by agitation and incubated at room temperature. Using a fluorescent plate reader (Model SPECTRAfluor Plus, Tecan), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}$$

The activity of caspase cascade activation was determined by the ratio of the net RFU value for (2-chloro-quinazolin-4-yl)-(4-methoxy-phenyl)-methyl-amine or other test compounds to that of control samples. The $EC_{50}$ (nM) was determined by a sigmoidal dose-response calculation (Prism 3.0, GraphPad Software Inc.).

The caspase activity (Ratio) and potency ($EC_{50}$) are summarized in Table I:

TABLE I

| | Caspase Activity and Potency | | | |
| --- | --- | --- | --- | --- |
| | T-47D (24 hr) | | T-47D (48 hr) | |
| Exa. Cmpd. | Ratio | $EC_{50}$ (nM) | Ratio | $EC_{50}$ (nM) |
| 1 | 8.7 | 2 | NA | NA |
| 2 | 6.7 | 31 | NA | NA |
| 3 | 8.1 | 79 | NA | NA |
| 4 | 10.3 | 24 | NA | NA |
| 5 | NA | NA | 12.8 | 48 |
| 6 | 5.7 | 56 | 11.5 | 89 |
| 7 | 6.7 | 6 | NA | NA |
| 8 | NA | NA | 6.1 | 47 |
| 9 | NA | NA | 12.4 | 20 |
| 10 | NA | NA | 14.7 | 34 |
| 11 | 8.3 | 5 | 11.4 | 11 |
| 12 | NA | NA | 9.0 | 1 |
| 13 | NA | NA | 4.9 | 5 |
| 14 | NA | NA | 10.8 | 1 |
| 15 | NA | NA | 7.1 | 11 |
| 16 | NA | NA | 6.5 | 13 |
| 17 | 7.2 | 18 | 12.5 | 22 |
| 18 | NA | NA | 12.5 | 38 |
| 19 | NA | NA | 13.1 | 4 |

TABLE I-continued

Caspase Activity and Potency

| | T-47D (24 hr) | | T-47D (48 hr) | |
|---|---|---|---|---|
| Exa. Cmpd. | Ratio | EC$_{50}$ (nM) | Ratio | EC$_{50}$ (nM) |
| 20 | NA | NA | 11.3 | 42 |
| 21 | 9.0 | 2 | 7.4 | 2 |
| 22 | 6.2 | 679 | 5.7 | 543 |
| 23 | 6.6 | 15 | 5.3 | 36 |
| 24 | 4.5 | 693 | NA | NA |
| 25 | 6.7 | 8 | NA | NA |
| 26 | 7.6 | 2 | NA | NA |
| 27 | 6.2 | 41 | NA | NA |
| 28 | 6.3 | 25 | NA | NA |
| 29 | NA | NA | 7.8 | 24 |
| 30 | 10.6 | 2 | NA | NA |
| 31 | 8.3 | 4 | NA | NA |
| 32 | NA | NA | 9.0 | 5 |
| 33 | 5.4 | 14 | 12.9 | 8 |
| 34 | 6.9 | 4 | NA | NA |
| 35 | 8.5 | 2 | NA | NA |
| 36 | 5.2 | 5 | NA | NA |
| 37 | 5.2 | 8 | NA | NA |
| 38 | 8.2 | 16 | NA | NA |
| 39 | 8.2 | 8 | NA | NA |
| 40 | 10 | 27 | NA | NA |
| 41 | 5.0 | 15 | NA | NA |
| 42 | 8.2 | 75 | NA | NA |
| 43 | 3.4 | 18 | NA | NA |
| 44 | 2.6 | 979 | NA | NA |
| 45 | 4.2 | 4 | NA | NA |
| 46 | 4.2 | 2360 | NA | NA |
| 47 | 3.9 | 29 | NA | NA |
| 48 | 2.4 | 14 | NA | NA |
| 49 | 7.5 | 4 | NA | NA |
| 50 | 9.0 | 14 | NA | NA |
| 51 | 4.0 | 7 | NA | NA |
| 52 | 6.4 | 382 | NA | NA |
| 53 | NA | NA | NA | NA |
| 54 | 7.1 | 872 | NA | NA |
| 55 | 6.7 | 219 | NA | NA |
| 56 | 8.6 | 282 | 14.6 | 265 |
| 57 | NA | NA | 14.3 | 501 |
| 58 | NA | NA | 12.5 | 46 |
| 59 | NA | NA | 12.7 | 316 |
| 60 | NA | NA | 6.2 | 432 |

NA = Not available

EXAMPLE 62

Determination of Brain/Plasma AUC Ratio of (2-Chloro-quinazolin-4-yl)-(4-methoxy-phenyl)-methyl-amine and Analogs For each test compound, forty five mice were injected via the tail vein with 0.10 mL of a 0.875 mg/mL solution of test compound dissolved in a formulation of 5% Cremophor, 5% Ethanol, and 90% D5W, or a formulation variation thereof. Five mice at each collection time point of approximately 0.05, 0.25, 0.50, 1.00, 2.00, 4.00, 8.00, 12.0 and 24.0 hours post dose were euthanized by halothane inhalation. Approximately 0.30 to 1.00 mL of blood from each animal was collected via cardiac puncture into tubes containing EDTA. Immediately after exsanguination, the whole brain from each animal was removed. The plasma and whole brain samples were frozen (~20° C.) separately until analysis. Plasma and brain samples were allowed to thaw at room temperature on the day of sample analysis. Prior to homogenization, the brains were weighed and three volumes of sterile water were added. Plasma and homogenized brain samples were extracted using a protein precipitation and filtration method. Briefly, 0.20 mL acetonitrile was added to 0.10 mL of sample in a Varian Captiva 20 μm filtration plate. A vacuum was applied to the plate and filtrates were collected. Filtrates were injected onto LC-MS/MS ABI2000 QTrap LC-MS/MS equipped with a reverse phase liquid chromatography inlet. Peak areas of the m/z product ions of the test compounds were measured against the peak are of the m/z internal standard production. The range of quantitation for the assay was between 1.00 and 1000 ng/mL for both analytes.

Pharmacokinetic parameters (PK) for the test compounds were estimated on median plasma and brain concentrations using non-compartmental analysis in WinNonlin (Pharsight Corp., Mountain View, Calif.). The validation of this software program is reported in MPI-REP-PA-03.00. All values below the quantitation limit (BQL) of 1.00 ng/mL were excluded from PK analysis. The areas under the concentration-time curve (AUC$_{0-\infty}$) were calculated using a linear/log trapezoidal method. The brain/plasma AUC ratios of tested Example Compounds are summarized in Table II:

TABLE II

| Brain/Plasma AUC Ratio | |
|---|---|
| Example Compound | Brain/Plasma AUC Ratio |
| 1 | 29.99 |
| 11 | 6.14 |
| 17 | 9.16 |
| 21 | 19.70 |
| 33 | 5.82 |
| 35 | 16.11 |
| 39 | 6.44 |
| 40 | 10.01 |
| 43 | 14.12 |
| 51 | 23.31 |

EXAMPLE 63

| Injection Formulation | |
|---|---|
| Excipients | Amount |
| Active Compound | 5 mg |
| PEG-400 | 5 grams |
| TPGS | 10 grams |
| Benzyl alcohol | 0.5 gram |
| Ethanol | 2 grams |
| D5W | Add to make 50 mL |

An injection formulation of a compound selected from Formula I (the "Active Compound") can be prepared according to the following method. Five mg of the Active Compound is dissolved into a mixture of the d-α-tocopheryl polyethylene glycol 1000 succinate (TPGS), PEG-400, ethanol, and benzyl alcohol. D5W is added to make a total volume of 50 mL and the solution is mixed. The resulting solution is filtered through a 0.2 μm disposable filter unit and is stored at 25° C. Solutions of varying strengths and volumes are prepared by altering the ratio of Active Compound in the mixture or changing the total amount of the solution.

EXAMPLE 64

| Tablet Formulation | |
|---|---|
| Active Compound | 100.0 mg |
| Lactose | 100.0 mg |
| Corn Starch | 50.0 mg |
| Hydrogenated Vegetable Oil | 10.0 mg |
| Polyvinylpyrrolidone | 10.0 mg |
| | 270.0 mg |

A formulation of tablets of a compound selected from Formulae I (the "Active Compound") can be prepared according to the following method. One hundred mg of Active Compound) is mixed with 100 mg lactose. A suitable amount of water for drying is added and the mixture is dried. The mixture is then blended with 50 mg of corn starch, 10 mg hydrogenated vegetable oil, and 10 mg polyvinylpyrrolidinone. The resulting granules are compressed into tablets. Tablets of varying strengths are prepared by altering the ratio of Active Compound in the mixture or changing the total weight of the tablet.

EXAMPLE 65

| Capsule Formulation | |
|---|---|
| Active Compound | 100.0 mg |
| Microcrystalline Cellulose | 200.0 mg |
| Corn Starch | 100.0 mg |
| Magnesium Stearate | 400.0 mg |
| | 800.0 mg |

A formulation of capsules containing 100.0 mg of a compound selected from Formulae I (the "Active Compound") can be prepared according to the following method. One hundred mg of Active Compound is mixed with 200 mg of microcrystalline cellulose and 100 mg of corn starch. Four hundred mg of magnesium stearate is then blended into the mixture and the resulting blend is encapsulated into a gelatin capsule. Doses of varying strengths can be prepared by altering the ratio of the Active Compound to pharmaceutically acceptable carriers or changing the size of the capsule.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of treating anaplastic astrocytoma, glioblastoma, meningioma, or mesenchymal tumor in a mammal in need of such treatment, comprising intravenously administering to the mammal an effective amount of a compound according to Formula I:

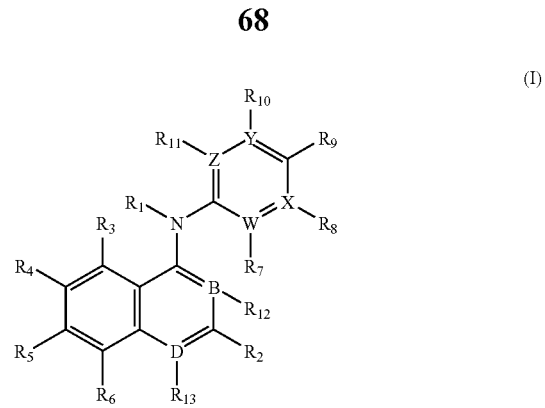

or a pharmaceutically acceptable salt or solvate thereof, wherein:
$R_1$ is $C_{1-3}$ alkyl;
$R_2$ is halo, $R_{14}$, $OR_{14}$, $SR_{14}$, $NR_{15}R_{14}$, or $NR_{14}(C=O)C_{1-6}$ alkyl wherein $R_{15}$ is $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl and $R_{14}$ is H, $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl;
$R_3$, $R_4$, $R_6$-$R_8$, $R_{10}$-$R_{13}$ are independently halo, $R_{16}$, $NR_{16}R_{17}$, $OR_{16}$, or $SR_{16}$ wherein $R_{16}$ and $R_{17}$ are independently H, $C_{1-6}$ alkyl, $C_{2-6}$ alkenyl, $C_{2-6}$ alkynyl, or $C_{1-6}$ haloalkyl provided that $R_{16}$ and $R_{17}$ are not both H;
$R_5$ is H or $C_{1-3}$ alkyl;
$R_9$ is H, halo, $R_{18}$, $OR_{18}$, $SR_{18}$, $NR_{18}R_{19}$, or optionally $R_9$ and one of $R_8$ and $R_{10}$ together form a heterocycle, wherein $R_{18}$ and $R_{19}$ are independently H, $C_{1-6}$ alkyl, $C_{2-6}$ alkenyl, $C_{2-6}$ alkynyl, or $C_{1-6}$ haloalkyl provided that $R_{18}$ and $R_{19}$ are not both H; and
B, D, W, X, Y and Z are independently C or N, provided that at least one of B and D is N, no more than one of W, X, Y and Z are N, and when B, D, W, X, Y or Z is N then there is no substituent at the N.

2. The method of claim 1 wherein B is C and D is N.
3. The method of claim 2 wherein X or Y is N.
4. The method of claim 2 wherein W or Z is N.
5. The method of claim 1 wherein $R_2$ is $C_{1-3}$ alkyl, halo, $C_{1-3}$ haloalkyl, $-OC_{1-3}$ alkyl, $-SC_{1-3}$ alkyl, $C_{3-8}$ heterocycle, $NR_{2a}C_{1-3}$ alkyl, $NR_{2a}(C=O)C_{1-3}$ alkyl, or $NR_{2a}$(arylalkyl) wherein $R_{2a}$ is H or $C_{1-3}$ alkyl.
6. The method of claim 5 wherein $R_1$ is $CH_3$.
7. The method of claim 6 wherein $R_5$ is H.
8. The method of claim 7 wherein $R_3$, $R_4$, $R_6$—$R_8$, $R_{10}$, $R_{11}$, and $R_{12}$ and $R_{13}$ if present, are independently H, $C_{1-3}$ alkyl, halo, $NH(C_{1-3}$ alkyl), $N(C_{1-3}$ alkyl)$_2$, or $-OC_{1-3}$ alkyl.
9. The method of claim 8 wherein $R_9$ is H, OH, $C_{1-3}$ alkyl, halo, $C_{1-3}$ haloalkyl, $-OC_{1-3}$ alkyl, $-SC_{1-3}$ alkyl, $-OC_{1-3}$ haloalkyl, $NR_{9a}R_{9b}$ wherein $R_{9a}$ and $R_{9b}$ are independently H or $C_{1-3}$ alkyl provided that $R_{9a}$ and $R_{9b}$ are not both H, or optionally $R_9$ and one of $R_8$ and $R_{10}$ together form a $C_{3-8}$ heterocycle.
10. The method of claim 1 wherein:
$R_1$ is $CH_2CH_3$, or $CH_3$;
$R_2$ is $CH_2CH_3$, $CH_3$, Cl, $CH_2F$, $OCH_3$, $SCH_3$, morpholino, $NHCH_3$, $NCH_3(C=O)CH_3$, or $NHCH_2C_6H_5$;
$R_3$, $R_4$, $R_6$, $R_{12}$, and $R_{13}$ are independently H, $CH_3$, Cl, $NHCH_3$, $N(CH_3)_2$, or $OCH_3$;
$R_5$ is H;
$R_7$, $R_8$, $R_{10}$ and $R_{11}$ are independently H, F, or $OCH_3$; and
$R_9$ is H, OH, Cl, $CH_3$, $CH_2CH_3$, $OCH_3$, $OCH_2CH_3$, $OCH_2CH_2CH_3$, $SCH_3$, $OCF_3$, $OCHF_2$, $OCH(CH_3)_2$, N(CH$_3$)$_2$, NHCH$_3$; or optionally R$_9$ and one of R$_8$ and R$_{10}$ together form 1,3-dioxolane.

11. The method of claim 1 wherein the compound has the structure according to Formula II:

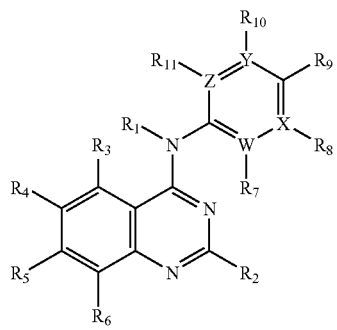

(II)

or a pharmaceutically acceptable salt or solvate thereof, wherein:

R$_1$ is C$_{1-3}$ alkyl;

R$_2$ is halo, R$_{14}$, OR$_{14}$, SR$_{14}$, NR$_{15}$R$_{14}$, or NR$_{14}$(C=O)C$_{1-6}$ alkyl wherein R$_{15}$ is C$_{1-6}$ alkyl, C$_{2-6}$ alkenyl, C$_{2-6}$ alkynyl, C$_{1-6}$ haloalkyl, C$_{3-8}$ carbocycle, C$_{3-8}$ heterocycle, C$_{6-10}$ aryl, or arylalkyl and R$_{14}$ is H, C$_{1-6}$ alkyl, C$_{2-6}$ alkenyl, C$_{2-6}$ alkynyl, C$_{1-6}$ haloalkyl, C$_{3-8}$ carbocycle, C$_{3-8}$ heterocycle, C$_{6-10}$ aryl, or arylalkyl;

R$_3$, R$_4$, R$_6$-R$_8$, R$_{10}$ and R$_{11}$ are independently halo, R$_{16}$, NR$_{16}$R$_{17}$, OR$_{16}$, or SR$_{16}$ wherein R$_{16}$ and R$_{17}$ are independently H, C$_{1-6}$ alkyl, C$_{2-6}$ alkenyl, C$_{2-6}$ alkynyl, or C$_{1-6}$ haloalkyl provided that R$_{16}$ and R$_{17}$ are not both H;

R$_5$ is H or C$_{1-3}$ alkyl;

R$_9$ is H, halo, R$_{18}$, OR$_{18}$, SR$_{18}$, NR$_{18}$R$_{19}$, or optionally R$_9$ and one of R$_8$ and R$_{10}$ together form a heterocycle, wherein R$_{18}$ and R$_{19}$ are independently H, C$_{1-6}$ alkyl, C$_{2-6}$ alkenyl, C$_{2-6}$ alkynyl, or C$_{1-6}$ haloalkyl provided that R$_{18}$ and R$_{19}$ are not both H; and W, X, Y and Z are independently C or N, provided that no more than one of W, X, Y and Z are N, and when W, X, Y or Z is N, then there is no substituent at the N.

12. The method of claim 11 wherein X or Y is N.

13. The method of claim 11 wherein W or Z is N.

14. The method of claim 11 wherein R$_2$ is C$_{1-3}$ alkyl, halo, C$_{1-3}$ haloalkyl, —OC$_{1-3}$ alkyl, —SC$_{1-3}$ alkyl, C$_{3-8}$ heterocycle, NR$_{2a}$C$_{1-3}$ alkyl, NR$_{2a}$(C=O)C$_{1-3}$ alkyl, or NR$_{2a}$(arylalkyl) wherein R$_{2a}$ is H or C$_{1-3}$ alkyl.

15. The method of claim 14 wherein R$_1$ is CH$_3$.

16. The method of claim 15 wherein R$_5$ is H.

17. The method of claim 16 wherein R$_3$, R$_4$, R$_6$—R$_8$, R$_{10}$ and R$_{11}$ are independently H, C$_{1-3}$ alkyl, halo, NH(C$_{1-3}$ alkyl), N(C$_{1-3}$ alkyl)$_2$, or —OC$_{1-3}$ alkyl.

18. The method of claim 17 wherein R$_9$ is H, OH, C$_{1-3}$ alkyl, halo, C$_{1-3}$ haloalkyl, —OC$_{1-3}$ alkyl, —SC$_{1-3}$ alkyl, —OC$_{1-3}$ haloalkyl, NR$_{9a}$R$_{9b}$ wherein R$_{9a}$ and R$_{9b}$ are independently H or C$_{1-3}$ alkyl provided that R$_{9a}$ and R$_{9b}$ are not both H, or optionally R$_9$ and one of R$_8$ and R$_{10}$ together form a C$_{3-8}$ heterocycle.

19. The method of claim 11 wherein:

R$_1$ is CH$_2$CH$_3$, or CH$_3$;

R$_2$ is CH$_2$CH$_3$, CH$_3$, Cl, CH$_2$F, OCH$_3$, SCH$_3$, morpholino, NHCH$_3$, NCH$_3$(C=O)CH$_3$, or NHCH$_2$C$_6$H$_5$;

R$_3$, R$_4$, and R$_6$, are independently H, CH$_3$, Cl, NHCH$_3$, N(CH$_3$)$_2$, or OCH$_3$;

R$_5$ is H;

R$_7$, R$_8$, R$_{10}$ and R$_{11}$ are independently H, F, or OCH$_3$; and

R$_9$ is H, OH, Cl, CH$_3$, CH$_2$CH$_3$, OCH$_3$, OCH$_2$CH$_3$, OCH$_2$CH$_2$CH$_3$, SCH$_3$, OCF$_3$, OCHF$_2$, OCH(CH$_3$)$_2$, N(CH$_3$)$_2$, NHCH$_3$; or optionally R$_9$ and one of R$_8$ and R$_{10}$ together form 1,3-dioxolane.

20. The method of claim 1 wherein the compound has the structure according to Formula III:

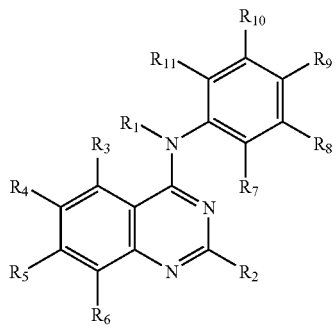

(III)

or a pharmaceutically acceptable salt or solvate thereof, wherein:

R$_1$ is C$_{1-3}$ alkyl;

R$_2$ is halo, R$_{15}$, OR$_{14}$, SR$_{14}$, NR$_{15}$R$_{14}$, or NR$_{14}$(C=O)C$_{1-6}$ alkyl wherein R$_{15}$ is C$_{1-6}$ alkyl, C$_{2-6}$ alkenyl, C$_{2-6}$ alkynyl, C$_{1-6}$ haloalkyl, C$_{3-8}$ carbocycle, C$_{3-8}$ heterocycle, C$_{6-10}$ aryl, or arylalkyl and R$_{14}$ is H, C$_{1-6}$ alkyl, C$_{2-6}$ alkenyl, C$_{2-6}$ alkynyl, C$_{1-6}$ haloalkyl, C$_{3-8}$ carbocycle, C$_{3-8}$ heterocycle, C$_{6-10}$ aryl, or arylalkyl;

R$_3$, R$_4$, R$_6$-R$_8$, R$_{10}$ and R$_{11}$ are independently halo, R$_{16}$, NR$_{16}$R$_{17}$, OR$_{16}$, or SR$_{16}$ wherein R$_{16}$ and R$_{17}$ are independently H, C$_{1-6}$ alkyl, C$_{2-6}$ alkenyl, C$_{2-6}$ alkynyl, or C$_{1-6}$ haloalkyl provided that R$_{16}$ and R$_{17}$ are not both H;

R$_5$ is H or C$_{1-3}$ alkyl; and

R$_9$ is H, halo, R$_{18}$, OR$_{18}$, SR$_{18}$, NR$_{18}$R$_{19}$, or optionally R$_9$ and one of R$_8$ and R$_{10}$ together form a heterocycle, wherein R$_{18}$ and R$_{19}$ are independently H, C$_{1-6}$ alkyl, C$_{2-6}$ alkenyl, C$_{2-6}$ alkynyl, or C$_{1-6}$ haloalkyl provided that R$_{18}$ and R$_{19}$ are not both H.

21. The method of claim 20 wherein R$_2$ is C$_{1-3}$ alkyl, halo, C$_{1-3}$ haloalkyl, —OC$_{1-3}$ alkyl, —SC$_{1-3}$ alkyl, C$_{3-8}$ heterocycle, NR$_{2a}$C$_{1-3}$ alkyl, NR$_{2a}$(C=O)C$_{1-3}$ alkyl, or NR$_{2a}$(arylalkyl) wherein R$_{2a}$ is H or C$_{1-3}$ alkyl.

22. The method of claim 21 wherein R$_1$ is CH$_3$.

23. The method of claim 22 wherein R$_5$ is H.

24. The method of claim 23 wherein R$_3$, R$_4$, R$_6$—R$_8$, R$_{10}$ and R$_{11}$ are independently H, C$_{1-3}$ alkyl, halo, NH(C$_{1-3}$ alkyl), N(C$_{1-3}$ alkyl)$_2$, or —OC$_{1-3}$ alkyl.

25. The method of claim 24 wherein R$_9$ is H, OH, C$_{1-3}$ alkyl, halo, C$_{1-3}$ haloalkyl, —OC$_{1-3}$ alkyl, —SC$_{1-3}$ alkyl, —OC$_{1-3}$ haloalkyl, NR$_{9a}$R$_{9b}$ wherein R$_{9a}$ and R$_{9b}$ are independently H or C$_{1-3}$ alkyl provided that R$_{9a}$ and R$_{9b}$ are not both H, or optionally R$_9$ and one of R$_8$ and R$_{10}$ together form a C$_{3-8}$ heterocycle.

26. The method of claim 20 wherein:

R$_1$ is CH$_2$CH$_3$ or CH$_3$;

R$_2$ is CH$_2$CH$_3$, CH$_3$, Cl, CH$_2$F, OCH$_3$, SCH$_3$, morpholino, NHCH$_3$, NCH$_3$(C=O)CH$_3$, or NHCH$_2$C$_6$H$_5$;

R$_3$, R$_4$, and R$_6$ are independently H, CH$_3$, Cl, NHCH$_3$, N(CH$_3$)$_2$, or OCH$_3$;

R$_5$ is H;

R$_7$, R$_8$, R$_{10}$ and R$_{11}$ are independently H, F, or OCH$_3$; and $R_9$ is H, OH, Cl, $CH_3$, $CH_2CH_3$, $OCH_3$, $OCH_2CH_3$, $OCH_2CH_2CH_3$, $SCH_3$, $OCF_3$, $OCHF_2$, $OCH(CH_3)_2$, $N(CH_3)_2$, $NHCH_3$; or optionally $R_9$ and one of $R_8$ and $R_{10}$ together form 1,3-dioxolane.

27. The method of claim 20 wherein:
$R_1$ is $CH_3$;
$R_2$ is $CH_3$, Cl, $OCH_3$, $NHCH_3$, or $NCH_3(C{=}O)CH_3$;
$R_3$-$R_6$, $R_7$, $R_8$, $R_{10}$ and $R_{11}$ are H; and
$R_9$ is $OCH_3$, $N(CH_3)_2$, or $NHCH_3$.

28. The method of claim 20, wherein when $R_9$ is H then $R_8$ and $R_{10}$ are not both H or one H and the other halo.

29. The method of claim 20, wherein when $R_9$ is H then $R_8$ and $R_{10}$ are not both H or one H and the other halo or alkyl or haloalkyl.

30. The method of claim 1, wherein when $R_9$ is $C_{1-6}$ alkyl, halo, or $C_{1-6}$ haloalkyl, $R_2$ is not H.

31. The method of claim 1, wherein when $R_9$ is H then $R_8$ and $R_{10}$ are not both H or one H and the other halo, and $R_2$ is not H.

32. The method of claim 1, wherein the compound is chosen from:
(2-Chloro-quinazolin-4-yl)-(4-methoxy-phenyl)-methyl-amine;
(2-Methoxy-quinazolin-4-yl)-(4-methoxyphenyl)-methylamine;
(4-Methoxy-phenyl)-methyl-(quinolin-4-yl)-amine;
(4-Methoxy-phenyl)-methyl-(2-methyl-quinazolin-4-yl)-amine hydrochloride;
(2-Methyl-quinazolin-4-yl)-(6-methoxy-pyridin-3-yl)-methyl-amine;
(4-Dimethylamino-phenyl)-(2-methyl-quinazolin-4-yl)-methyl-amine;
(2-Methylamino-quinazolin-4-yl)-(4-methoxy-phenyl)-methyl-amine;
(2-Methylamino-quinazolin-4-yl)-(6-methoxy-pyridin-3-yl)-methyl-amine;
(2-Methyl-quinazolin-4-yl)-(4-methylamino-phenyl)-methylamine;
(4-Methoxy-phenyl)-(2-N-methylacetamido-quinazolin-4-yl)-methylamine;
and pharmaceutically acceptable salts or solvates thereof.

33. The method of claim 1, wherein the compound is chosen from:
(2-Chloro-quinazolin-4-yl)-(4-methoxy-phenyl)-methyl-amine;
(2-Chloro-quinazolin-4-yl)-(4-methyl-phenyl)-methyl-amine;
(2-Chloro-quinazolin-4-yl)-(4-chloro-phenyl)-methyl-amine;
(2-Chloro-quinazolin-4-yl)-(4-trifluoromethoxy-phenyl)-methyl-amine;
(2-Chloro-quinazolin-4-yl)-(6-methoxy-pyridin-3-yl)-methyl-amine;
(2-Chloro-quinazolin-4-yl)-ethyl-(4-methoxy-phenyl)-amine;
(2-Chloro-quinazolin-4-yl)-(2,4-dimethoxy-phenyl)-methyl-amine;
(2-Chloro-quinazolin-4-yl)-(3-methoxy-phenyl)-methyl-amine;
(2-Chloro-6-methyl-quinazolin-4-yl)-(4-methoxy-phenyl)-methyl-amine;
(2-Chloro-5-methyl-quinazolin-4-yl)-(4-methoxy-phenyl)-methyl-amine;
(2-Chloro-8-methyl-quinazolin-4-yl)-(4-methoxy-phenyl)-methyl-amine;
(2,6-Dichloro-quinazolin-4-yl)-(4-methoxy-phenyl)-methyl-amine;
(2-Chloro-quinazolin-4-yl)-(3,4-methylenedioxyphenyl)-methyl-amine;
(2-Chloro-quinazolin-4-yl)-(3,4-dimethoxy-phenyl)-methyl-amine;
(2-Chloro-quinazolin-4-yl)-(4-propoxy-phenyl)-methyl-amine;
(2-Chloro-quinazolin-4-yl)-(2,3-dimethoxy-phenyl)-methyl-amine;
(2,8-Dichloro-quinazolin-4-yl)-(4-methoxy-phenyl)-methyl-amine;
(2,5-Dichloro-quinazolin-4-yl)-(4-methoxy-phenyl)-methyl-amine;
(2-Chloro-quinazolin-4-yl)-(4-ethoxy-phenyl)-methylamine;
(2-Chloro-quinazolin-4-yl)-(4-dimethylaminophenyl)-methylamine;
(2-Chloro-quinazolin-4-yl)-(4-nitro-phenyl)-methyl-amine;
(2-Chloro-quinazolin-4-yl)-phenyl-methyl-amine;
(2-Chloro-quinazolin-4-yl)-(2,5-dimethoxy-phenyl)-methyl-amine;
(2-Chloro-quinazolin-4-yl)-(2-methoxy-phenyl)-methyl-amine;
(2-Chloro-quinazolin-4-yl)-(4-hydroxyphenyl)-methylamine;
(2,7-Dichloro-quinazolin-4-yl)-(4-methoxy-phenyl)-methyl-amine;
(2-Chloro-7-methyl-quinazolin-4-yl)-(4-methoxy-phenyl)-methyl-amine;
and pharmaceutically acceptable salts or solvates thereof.

34. The method of claim 1, wherein the compound is chosen from:
(2-Fluoromethyl-quinazolin-4-yl)-(4-methoxy-phenyl)-methyl-amine;
(4-Methoxy-phenyl)-methyl-(2-methyl-quinazolin-4-yl)-amine hydrochloride;
(2-Chloromethyl-quinazolin-4-yl)-(4-methoxy-phenyl)-methyl-amine;
(2-Ethyl-quinazolin-4-yl)-(4-methoxy-phenyl)-methyl-amine;
(4-Difluoromethoxy-phenyl)-(2-methyl-quinazolin-4-yl)-methyl-amine;
(3-Fluoro-4-methoxy-phenyl)-(2-methyl-quinazolin-4-yl)-methyl-amine;
(4-Isopropoxy-phenyl)-(2-methyl-quinazolin-4-yl)-methyl-amine;
(4-Ethyl-phenyl)-(2-methyl-quinazolin-4-yl)-methyl-amine;
(5-Methoxy-2-methyl-quinazolin-4-yl)-(4-methoxy-phenyl)-methyl-amine;
(2-Methyl-quinazolin-4-yl)-(6-methoxy-pyridin-3-yl)-methyl-amine;
(2-Fluoro-4-methoxy-phenyl)-(2-methyl-quinazolin-4-yl)-methyl-amine;
(4-Dimethylamino-phenyl)-(2-methyl-quinazolin-4-yl)-methyl-amine;
(4-Ethoxy-phenyl)-(2-methyl-quinazolin-4-yl)-methyl-amine;
(5-Methoxy-pyridin-2-yl)-(2-methyl-quinazolin-4-yl)-methyl-amine;
(2-Methyl-quinazolin-4-yl)-(4-methylamino-phenyl)-methylamine;
(2-Methyl-6-nitroquinazolin-4-yl)-(4-dimethylaminophenyl)-methylamine;
(4-Methylthio-phenyl)-(2-methyl-quinazolin-4-yl)-methylamine;

(2-Dimethylamino-pyridine-5-yl)-(2-methyl-quinazolin-4-yl)-methylamine;
(6-Dimethylamino-2-methyl-quinazolin-4-yl)-(4-methoxy-phenyl)-methylamine;
(3,4,5-Trimethoxy-phenyl)-(2-methyl-quinazolin-4-yl)-methylamine;
and pharmaceutically acceptable salts or solvates thereof.

35. The method of claim 1, wherein the compound is chosen from:
$N^2$-Hydroxyl-$N^4$-(4-methoxy-phenyl)-$N^4$-methyl-quinazoline-2,4-diamine;
(4-Methoxy-phenyl)-methyl-(2-morpholin-4-yl-quinazolin-4-yl)-amine;
(2-Methoxy-quinazolin-4-yl)-(4-methoxyphenyl)-methylamine;
(4-Methoxy-phenyl)-methyl-(quinolin-4-yl)-amine;
(2-Methylthio-quinazolin-4-yl)-(4-methoxy-phenyl)-methyl-amine;
(2-Dimethylamino-quinazolin-4-yl)-(4-methoxy-phenyl)-methyl-amine;
(2-Methylamino-quinazolin-4-yl)-(4-methoxy-phenyl)-methyl-amine;
(2-Methylamino-quinazolin-4-yl)-(6-methoxy-pyridin-3-yl)-methyl-amine;
(2-Benzylamino-quinazolin-4-yl)-(4-methoxyphenyl)-methylamine;
(2-Dimethylamino-6-nitroquinazolin-4-yl)-(4-methoxyphenyl)-methylamine;
(2-Methylamino-quinazolin-4-yl)-(4-dimethylaminophenyl)-methylamine;
[2-(N-Methyl-acetamido)-quinazolin-4-yl]-(4-dimethylaminophenyl)-methylamine;
(4-Methoxy-phenyl)-(2-N-methylacetamido-quinazolin-4-yl)-methylamine;
and pharmaceutically acceptable salts or solvates thereof.

36. The method of claim 1, wherein a brain/plasma AUC ratio of said compound after administration is greater than about 5.

37. The method of claim 1, wherein a brain/plasma AUC ratio of said compound after administration is greater than about 10.

38. The method of claim 1, wherein a brain/plasma AUC ratio of said compound after administration is greater than about 15.

39. The method of claim 1, wherein the compound has a calculated polar surface area of less than about 100 square Angstroms.

40. The method of claim 1, wherein the compound has a calculated polar surface area of less than about 80 square Angstroms.

41. A method of treating a metastatic brain cancer in a mammal in need of such treatment, comprising intravenously administering to the mammal an effective amount of a compound according to Formula I:

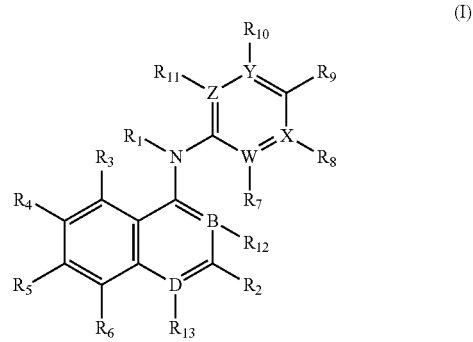

(I)

or a pharmaceutically acceptable salt or solvate thereof, wherein:
$R_1$ is $C_{1-3}$ alkyl;
$R_2$ is halo, $R_{14}$, $OR_{14}$, $SR_{14}$, $NR_{15}R_{14}$ or $NR_{14}(C\!=\!O)C_{1-6}$ alkyl wherein $R_{15}$ is $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl and $R_{14}$ is H, $C_{1-6}$ alkyl, $C_{2-6}$ alkenyl, $C_{2-6}$ alkynyl, $C_{1-6}$ haloalkyl, $C_{3-8}$ carbocycle, $C_{3-8}$ heterocycle, $C_{6-10}$ aryl, or arylalkyl;
$R_3$, $R_4$, $R_6$-$R_8$, $R_{10}$-$R_{13}$ are independently halo, $R_{16}$, $NR_{16}R_{17}$, $OR_{16}$, or $SR_{16}$ wherein $R_{16}$ and $R_{17}$ are independently H, $C_{1-6}$ alkyl, $C_{2-6}$ alkenyl, $C_{2-6}$ alkynyl, or $C_{1-6}$ haloalkyl provided that $R_{16}$ and $R_{17}$ are not both H;
$R_5$ is H or $C_{1-3}$ alkyl;
$R_9$ is H, halo, $R_{18}$, $OR_{18}$, $SR_{18}$, $NR_{18}R_{19}$, or optionally $R_9$ and one of $R_8$ and $R_{10}$ together form a heterocycle, wherein $R_{18}$ and $R_{19}$ are independently H, $C_{1-6}$ alkyl, $C_{2-6}$ alkenyl, $C_{2-6}$alkenyl, or $C_{1-6}$ haloalkyl provided that $R_{18}$ and $R_{19}$ are not both H; and
B, D, W, X, Y and Z are independently C or N, provided that at least one of B and D is N, no more than one of W, X, Y and Z are N, and when B, D, W, X, Y or Z is N then there is no substituent at the N.

* * * * *